US009277925B2

(12) United States Patent
Scianamblo

(10) Patent No.: US 9,277,925 B2
(45) Date of Patent: Mar. 8, 2016

(54) PRECESSIONAL DRILLING AND REAMING

(71) Applicant: Michael J. Scianamblo, Tiburon, CA (US)

(72) Inventor: Michael J. Scianamblo, Tiburon, CA (US)

(*) Notice: Subject to any disclaimer, the term of this patent is extended or adjusted under 35 U.S.C. 154(b) by 0 days.

(21) Appl. No.: 14/464,596

(22) Filed: Aug. 20, 2014

(65) Prior Publication Data

US 2015/0056032 A1 Feb. 26, 2015

Related U.S. Application Data

(60) Provisional application No. 61/868,276, filed on Aug. 21, 2013, provisional application No. 61/899,705, filed on Nov. 4, 2013.

(51) Int. Cl.
*B23B 51/02* (2006.01)
*A61B 17/16* (2006.01)
(Continued)

(52) U.S. Cl.
CPC ............ *A61B 17/1615* (2013.01); *A61B 17/164* (2013.01); *A61C 3/02* (2013.01); *B23B 51/00* (2013.01); *B23B 51/0081* (2013.01); *B23B 51/02* (2013.01); *B28D 1/14* (2013.01); *B28D 1/146* (2013.01); *B23B 2250/16* (2013.01); *B23B 2251/204* (2013.01); *B23B 2251/244* (2013.01); *B23B 2251/245* (2013.01);
(Continued)

(58) Field of Classification Search
CPC B23B 51/02; B23B 225/241; B23B 225/245; B23B 225/406; B23B 225/4061; Y10T 408/9097; Y10T 408/909; Y10T 408/78; Y10T 408/81; Y10T 408/854

USPC .................. 408/230, 227, 144, 145, 150, 1 R
See application file for complete search history.

(56) References Cited

U.S. PATENT DOCUMENTS 2,930,264 A * 3/1960 Lovret ........................... 408/229
3,400,617 A * 9/1968 Sanborn ........................ 408/223
(Continued)

FOREIGN PATENT DOCUMENTS

EP        0 120 542      10/1984
EP        987076 A2 * 3/2000 .............. B23B 51/02
(Continued)

OTHER PUBLICATIONS

Partial European Search Report, European Application Serial No. EP 06 00 7527, Jun. 26, 2006, 6 pages.
(Continued)

*Primary Examiner* — Sunil K Singh
*Assistant Examiner* — Ryan Rufo
(74) *Attorney, Agent, or Firm* — Fish & Richardson P.C.

(57) ABSTRACT

This document provides novel drills and/or reamers that are well-suited for making holes in a variety of materials including, but not limited to, metals, ceramics, glass, wood, plasterboard, plastics, stone, composites, synthetics, silicon or multi-layered or hybridized substrates. In some embodiments, these drilling devices have some centers of mass that are offset from the axis of rotation. Accordingly, such drills and/or reamers may rotate and cut using a precessional pattern of motion. Precessional cutting devices may display a mechanical wave pattern in relationship to the longitudinal axis of the device. If the cutting device is fabricated from a flexible material, for example Nickel-Titanium, bodily deflection of the device may result during rotation.

35 Claims, 58 Drawing Sheets

(51) Int. Cl.
*B23B 51/00* (2006.01)
*A61C 3/02* (2006.01)
*B28D 1/14* (2006.01)

(52) U.S. Cl.
CPC ........... *Y10T 408/03* (2015.01); *Y10T 408/455* (2015.01); *Y10T 408/89* (2015.01); *Y10T 408/905* (2015.01); *Y10T 408/909* (2015.01); *Y10T 408/9097* (2015.01); *Y10T 409/303808* (2015.01)

(56) References Cited

U.S. PATENT DOCUMENTS

| | | | |
|---|---|---|---|
| 3,824,026 A * | 7/1974 | Gaskins | 408/210 |
| 4,044,468 A | 8/1977 | Kahn | |
| 4,190,386 A * | 2/1980 | Brabetz et al. | 408/1 R |
| 4,231,692 A * | 11/1980 | Brabetz et al. | 408/230 |
| 4,332,561 A | 6/1982 | McSpadden | |
| 4,353,698 A | 10/1982 | McSpadden | |
| 4,456,411 A * | 6/1984 | Clement | 408/223 |
| 4,457,710 A | 7/1984 | McSpadden | |
| 4,536,159 A | 8/1985 | Roane | |
| 4,538,989 A | 9/1985 | Apairo, Jr. et al. | |
| 4,762,445 A * | 8/1988 | Bunting et al. | 408/144 |
| 4,842,451 A | 6/1989 | Dugger | |
| 4,889,487 A | 12/1989 | Lovaas | |
| 4,934,934 A | 6/1990 | Arpaio, Jr. et al. | |
| 4,992,048 A | 2/1991 | Goof | |
| 5,106,298 A | 4/1992 | Heath et al. | |
| 5,464,362 A | 11/1995 | Heath et al. | |
| 5,498,158 A | 3/1996 | Wong | |
| 5,503,554 A | 4/1996 | Schoeffel | |
| 5,584,617 A * | 12/1996 | Houser | 408/1 R |
| 5,605,460 A | 2/1997 | Heath et al. | |
| 5,658,145 A | 8/1997 | Maillefer et al. | |
| 5,676,541 A | 10/1997 | Maillefer et al. | |
| 5,713,736 A * | 2/1998 | Heath et al. | 433/102 |
| 5,752,825 A | 5/1998 | Buchanan | |
| 5,775,904 A | 7/1998 | Riitano | |
| 5,836,764 A | 11/1998 | Buchanan | |
| 5,842,862 A | 12/1998 | Nissan | |
| 5,882,198 A | 3/1999 | Taylor et al. | |
| 5,897,274 A * | 4/1999 | Ogura et al. | 408/230 |
| 5,897,316 A | 4/1999 | Buchanan | |
| 5,902,106 A | 5/1999 | McSpadden | |
| 5,921,775 A | 7/1999 | Buchanan | |
| 5,938,440 A | 8/1999 | McSpadden | |
| 5,980,166 A * | 11/1999 | Ogura | 408/57 |
| 5,984,679 A | 11/1999 | Farzin-Nia et al. | |
| 6,106,296 A | 8/2000 | Johnson | |
| 6,299,445 B1 | 10/2001 | Garman | |
| 6,315,558 B1 | 11/2001 | Farzin-Nia et al. | |
| 6,419,488 B1 | 7/2002 | McSpadden et al. | |
| 6,575,748 B1 | 6/2003 | Filhol | |
| 6,702,579 B1 | 3/2004 | Hoppe et al. | |
| 6,890,134 B1 | 5/2005 | Wagner et al. | |
| 6,929,078 B1 | 8/2005 | Randall | |
| 6,942,484 B2 | 9/2005 | Scianamblo | |
| 7,094,056 B2 | 8/2006 | Scianamblo | |
| 7,125,252 B2 | 10/2006 | Rouiller et al. | |
| 7,717,710 B2 * | 5/2010 | Danger et al. | 433/165 |
| 7,955,078 B2 | 6/2011 | Scianamblo | |
| 8,454,361 B2 | 6/2013 | Scianamblo | |
| 8,496,476 B2 | 7/2013 | Scianamblo | |
| 8,727,680 B2 * | 5/2014 | Wada et al. | 408/226 |
| 8,882,504 B2 | 11/2014 | Scianamblo | |
| 2002/0031745 A1 | 3/2002 | Kumar et al. | |
| 2004/0023186 A1 | 2/2004 | McSpadden | |
| 2004/0042865 A1 * | 3/2004 | Oettle | 409/234 |
| 2004/0131993 A1 | 7/2004 | Rouiller et al. | |
| 2004/0185414 A1 | 9/2004 | Badoz | |
| 2004/0219485 A1 | 11/2004 | Scianamblo | |
| 2004/0253379 A1 * | 12/2004 | Sugita et al. | 427/355 |
| 2004/0265775 A1 | 12/2004 | Maillefer et al. | |
| 2005/0026109 A1 | 2/2005 | Buchanan | |
| 2005/0117984 A1 * | 6/2005 | Eason et al. | 408/144 |
| 2005/0266375 A1 | 12/2005 | Brock et al. | |
| 2005/0282117 A1 | 12/2005 | Aravena et al. | |
| 2006/0068362 A1 | 3/2006 | Desrosiers et al. | |
| 2006/0111724 A1 | 5/2006 | Ping | |
| 2006/0115650 A1 * | 6/2006 | Hanyu et al. | 428/408 |
| 2006/0228668 A1 | 10/2006 | McSpadden | |
| 2007/0015107 A1 | 1/2007 | Mannschedel et al. | |
| 2007/0059663 A1 | 3/2007 | Scianamblo | |
| 2007/0082318 A1 | 4/2007 | Breguet | |
| 2007/0184406 A1 | 8/2007 | Mason | |
| 2009/0047080 A1 * | 2/2009 | Schweighofer et al. | 408/59 |
| 2010/0221078 A1 * | 9/2010 | Borschert | 408/1 R |
| 2011/0236853 A1 | 9/2011 | Shimoo | |
| 2012/0039680 A1 * | 2/2012 | Koike et al. | 408/1 R |
| 2012/0282571 A1 | 11/2012 | Ammon et al. | |
| 2013/0170920 A1 * | 7/2013 | Ogawa | 408/1 R |
| 2013/0189644 A1 | 7/2013 | Johnson | |
| 2013/0273497 A1 | 10/2013 | Scianamblo | |
| 2013/0302749 A1 | 11/2013 | Scianamblo | |

FOREIGN PATENT DOCUMENTS

| | | | | |
|---|---|---|---|---|
| EP | 1 184 004 | | 3/2002 | |
| EP | 1 213 074 | | 6/2002 | |
| FR | 2 798 277 | | 3/2001 | |
| FR | 2854054 A1 * | 10/2004 | ............. B23B 51/02 |
| JP | 52-156494 A * | 12/1977 | ............. B23B 51/02 |
| JP | 57-127608 A * | 8/1982 | ............. B23B 51/02 |
| JP | 62-241606 A * | 10/1987 | ............. B23B 51/02 |
| JP | 06-320323 A * | 11/1994 | ............. B23B 51/00 |
| JP | 11-019812 A * | 1/1999 | ............. B23B 51/00 |
| JP | 2002-144122 A * | 5/2002 | ............. B23B 51/00 |
| JP | 2002-205213 A * | 7/2002 | ............. B23B 51/00 |
| JP | 2007-283473 A * | 11/2007 | ............. B23B 51/00 |
| SU | 637207 A * | 12/1978 | ............. B23B 51/02 |
| WO | WO 02/065938 | | 8/2002 | |
| WO | WO 2004/098438 | | 11/2004 | |
| WO | WO 2009/001681 A1 * | 12/2008 | ............. B23B 51/02 |
| WO | WO2014/118591 | | 8/2014 | |

OTHER PUBLICATIONS

EP 04 75 1290 Supplementary European Search Report, Jun. 5, 2007, 5 pages.
EP 04 75 0878 Supplementary European Search Report, Jun. 5, 2007, 3 pages.
Communication pursuant to Article 94(3) EPC for Application No. EP 06 00 7527.2-1265, dated Jun. 17, 2009, 5 pages.
Linear definition from Merriam-Webster on-line. Retrieved on Feb. 20, 2009, from http://www.merriam-webster.com/dictionary/linear, 3 pages.
Straight. (n.d.). Dictionary.com Unabridged. Retrieved Feb. 11, 2010, from Dictionary.com website: http://dictionary.reference.com/browse/straight, 12 pages.
USPTO Non-Final Office Action in U.S. Appl. No. 11/402,207, mailed Feb. 26, 2009, 16 pages.
USPTO Final Office Action in U.S. Appl. No. 11/402,207, mailed Oct. 6, 2009, 9 pages.
USPTO Non-Final Office Action in U.S. Appl. No. 11/402,207, mailed Feb. 19, 2010, 10 pages.
USPTO Non-Final Office Action in U.S. Appl. No. 11/226,059, mailed Mar. 31, 2008, 5 pages.
USPTO Final Office Action in U.S. Appl. No. 11/226,059, mailed May 13, 2009, 8 pages.
USPTO Non-Final Office Action in U.S. Appl. No. 11/226,059, mailed Oct. 21, 2009, 9 pages.
USPTO Final Office Action in U.S. Appl. No. 11/226,059, mailed May 17, 2010, 9 pages.
Office Action in U.S. Appl. No. 11/402,207, mailed Aug. 25, 2010, 13 pages.
USPTO Non-Final Office Action in U.S. Appl. No. 11/402,207, mailed Aug. 28, 2012, 7 pages.

(56) References Cited

OTHER PUBLICATIONS

International Search Report and Written Opinion of International Patent Application No. PCT/US2014/051909, filed Aug. 20, 2014. Received Dec. 22, 2014. 18 pages.

Ultimate Handyman. *Drilling Through Walls*. YouTube. Published Sep. 23, 2011. Retrieved on Nov. 11, 2014. Retrieved from the internet: URL<https://www.youtube.com/watch?v=fpFUxlcH2Lg>.

"Protaper Next". Dentsply Tulsa Dental Specialties. Last updated Dec. 5, 2014. Retrieved on Dec. 5, 2014. Retrieved from the internet: URC:<http://www.tulsadentalspecialties.com/default/endodontics_brands/PROTAPERNEXT.aspx>. 1 page.

International Search Report and Written Opinion of International Patent Application No. PCT/US2014/051916, filed Aug. 20, 2014. Received Feb. 4, 2015. 18 pages.

* cited by examiner

Cross-section A-A

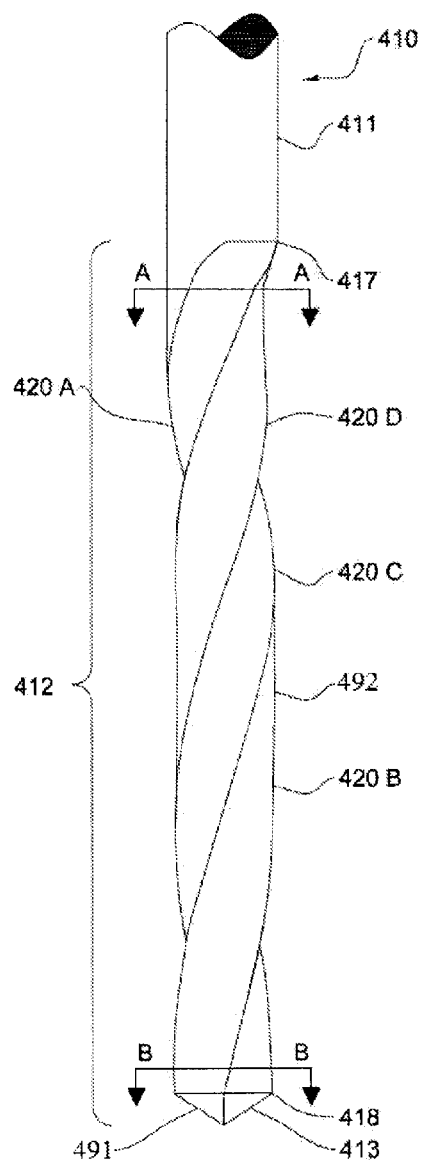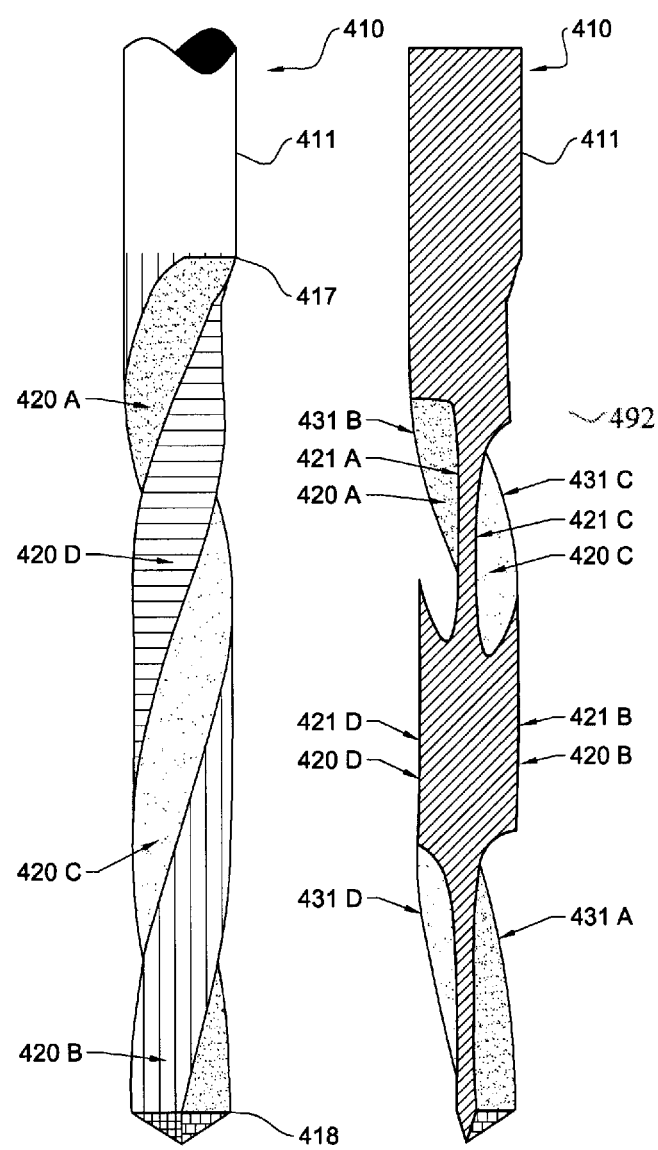
*FIG. 14*     *FIG. 15*  *FIG. 16*

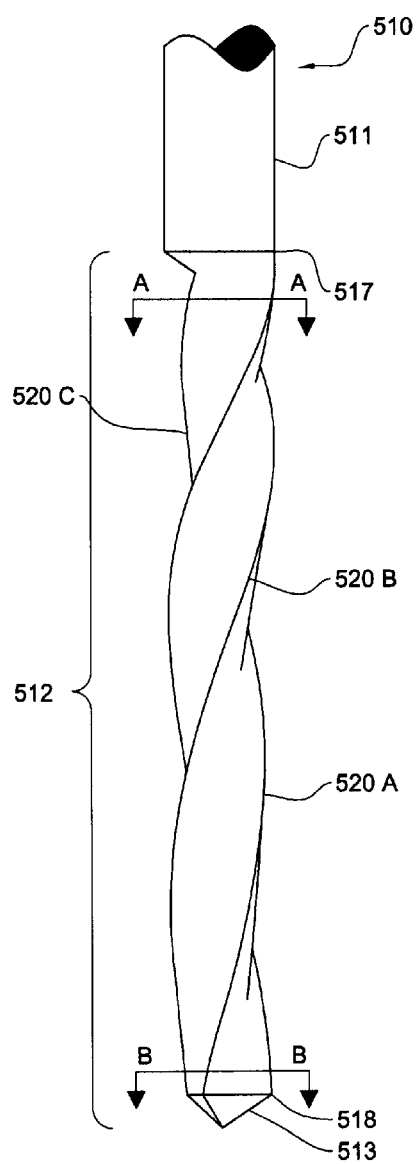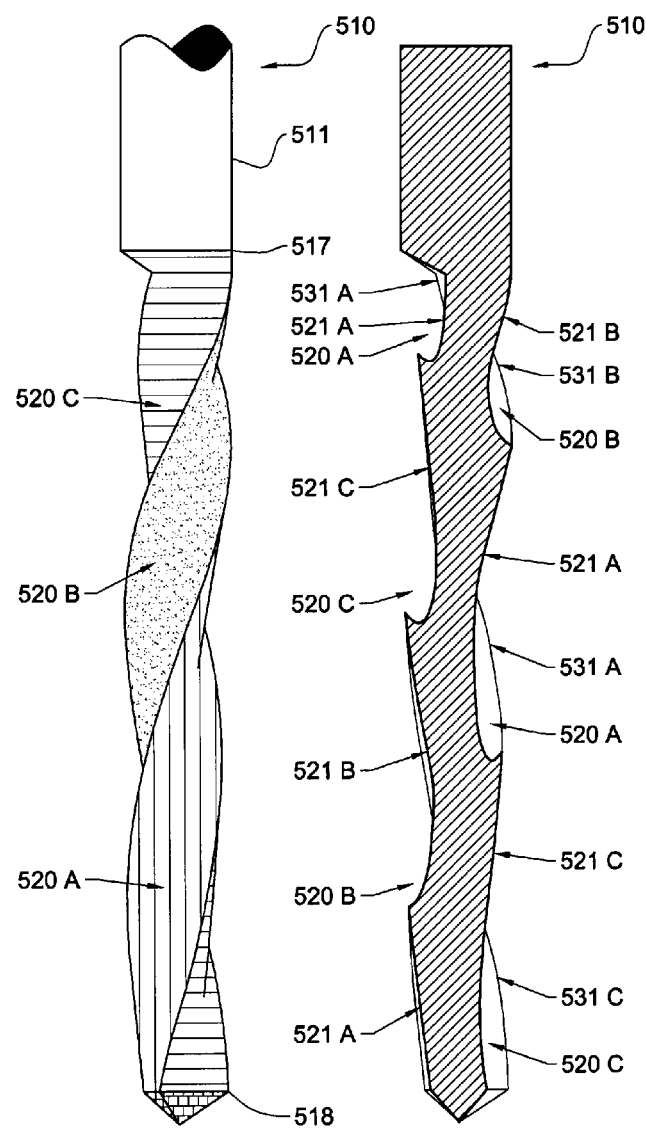
FIG. 22  FIG. 23  FIG. 24

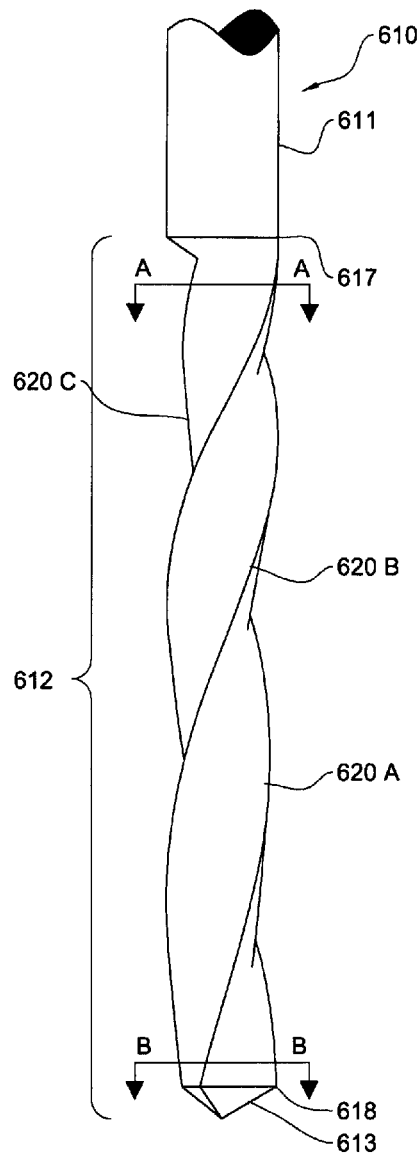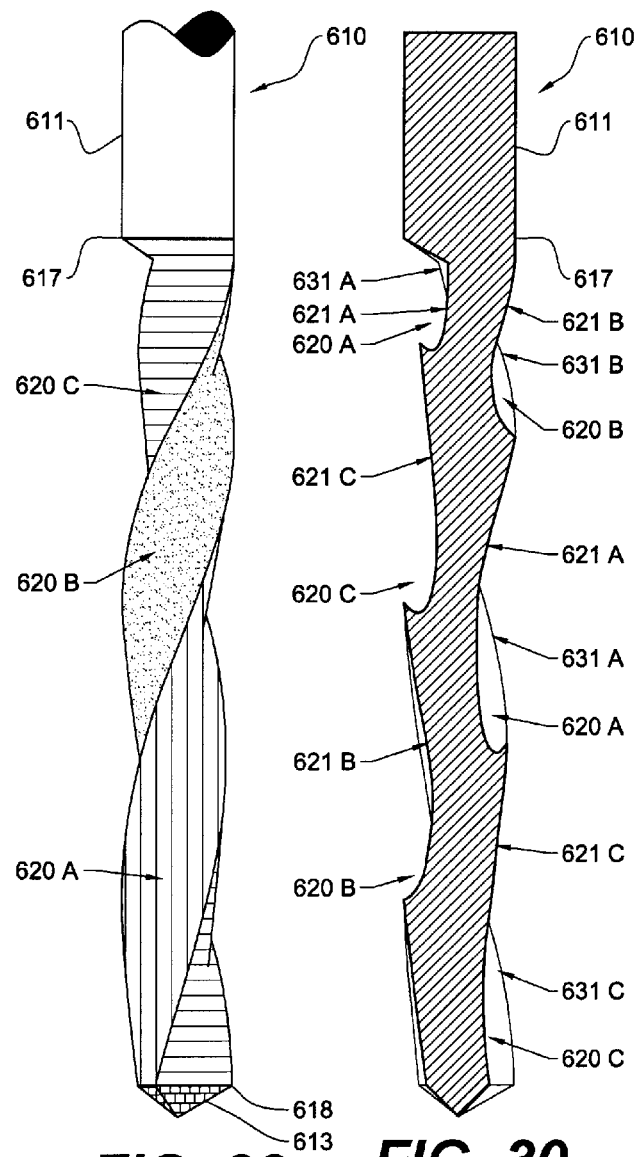
FIG. 28    FIG. 29    FIG. 30

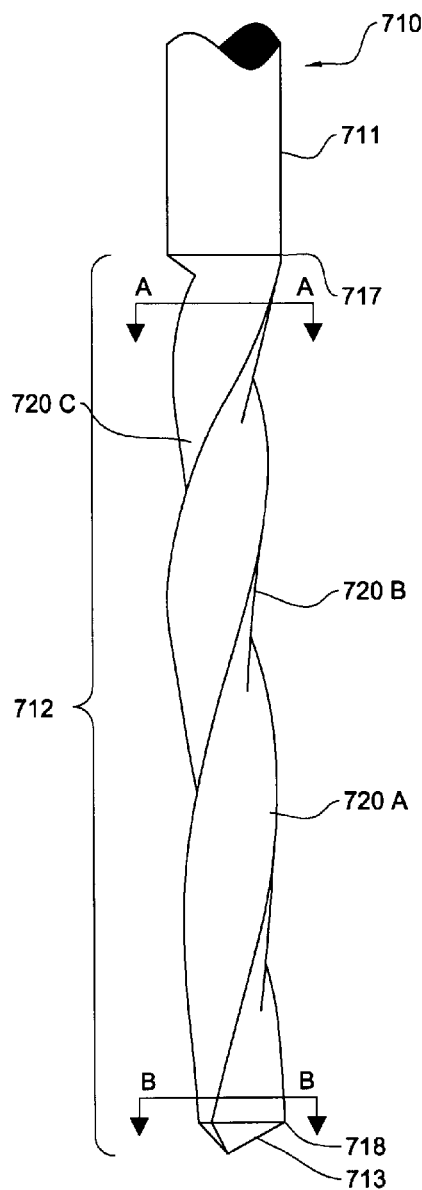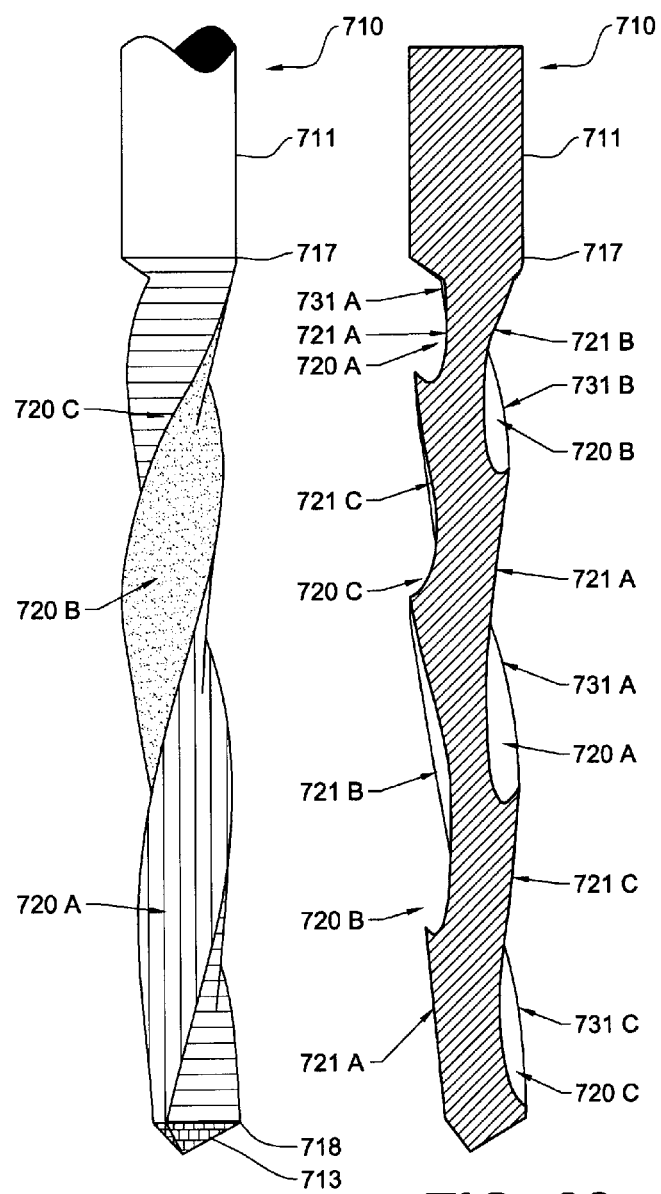
FIG. 37   FIG. 38   FIG. 39

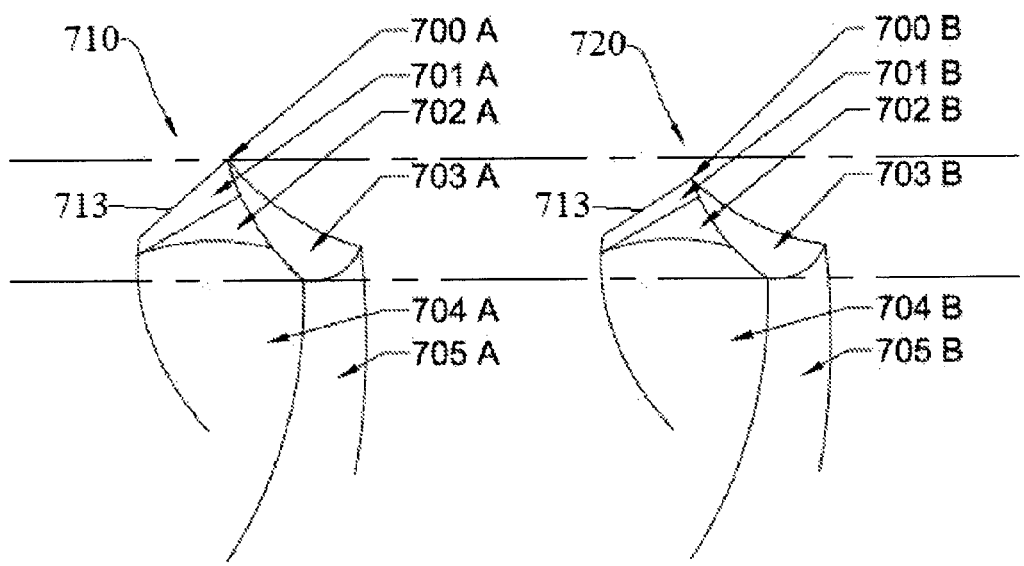
FIG. 43  FIG. 44

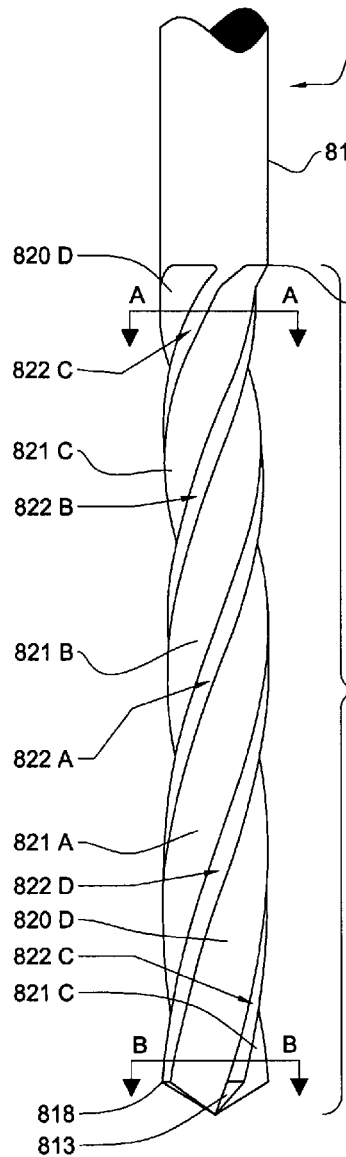
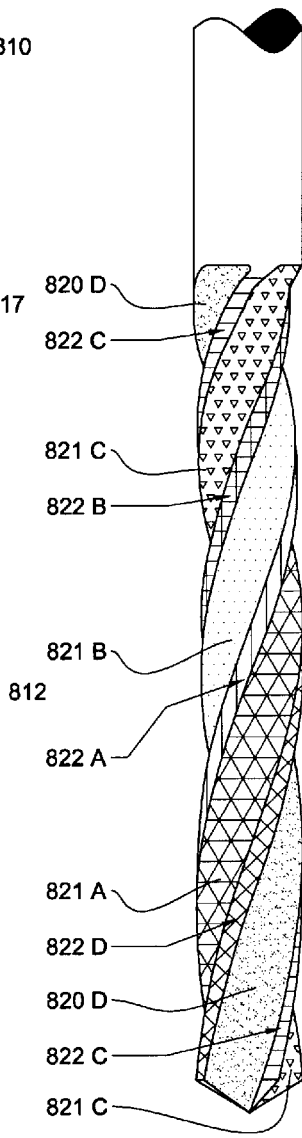
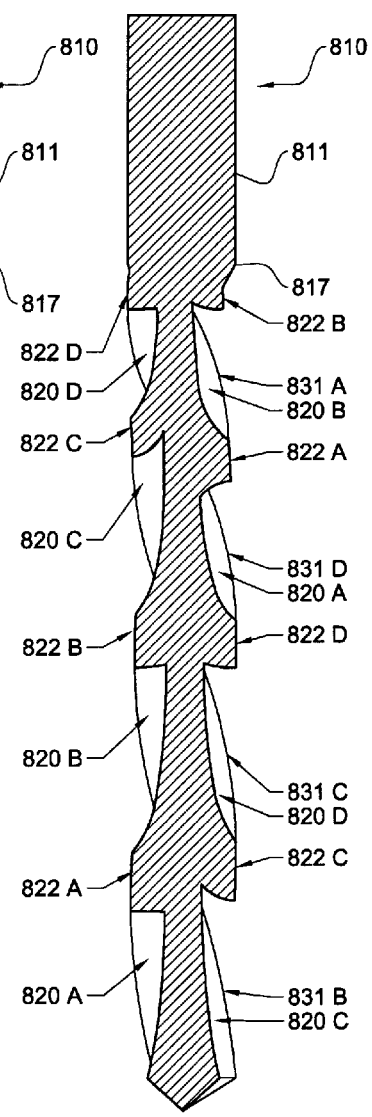
*FIG. 45*  *FIG. 46*  *FIG. 47*

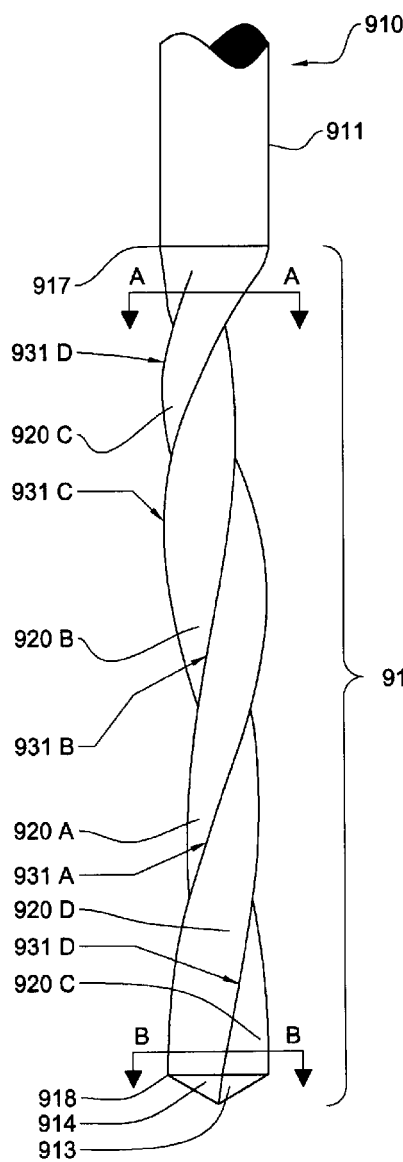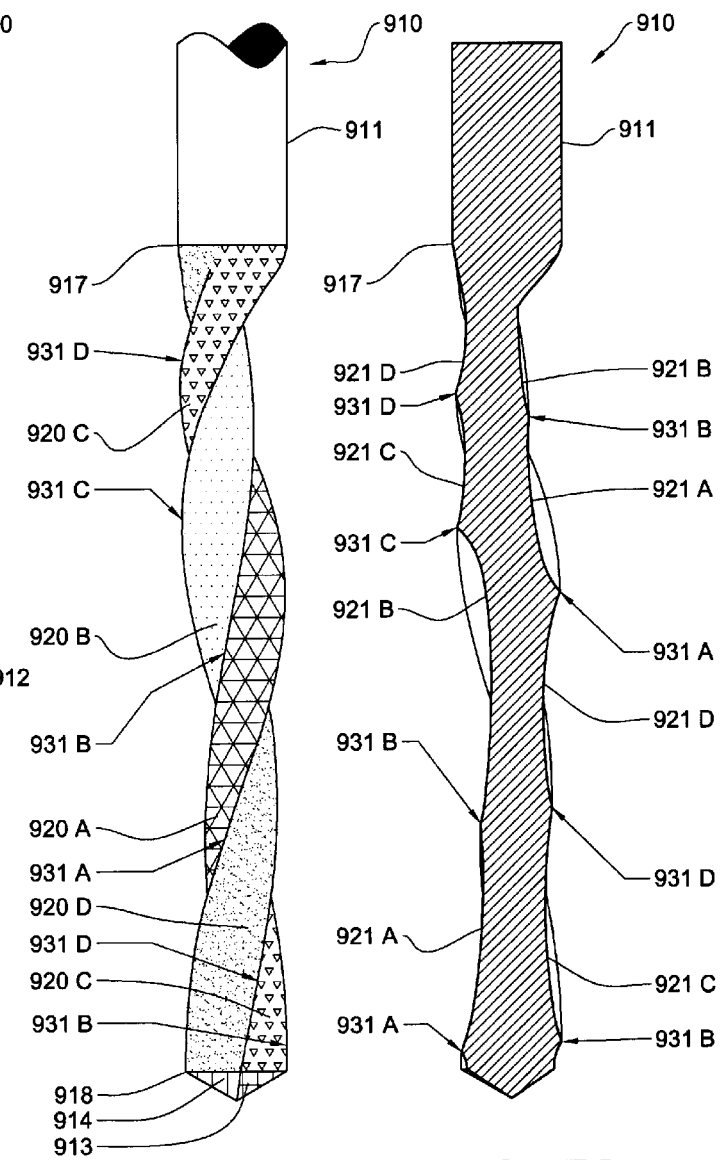
FIG. 51  FIG. 52  FIG. 53

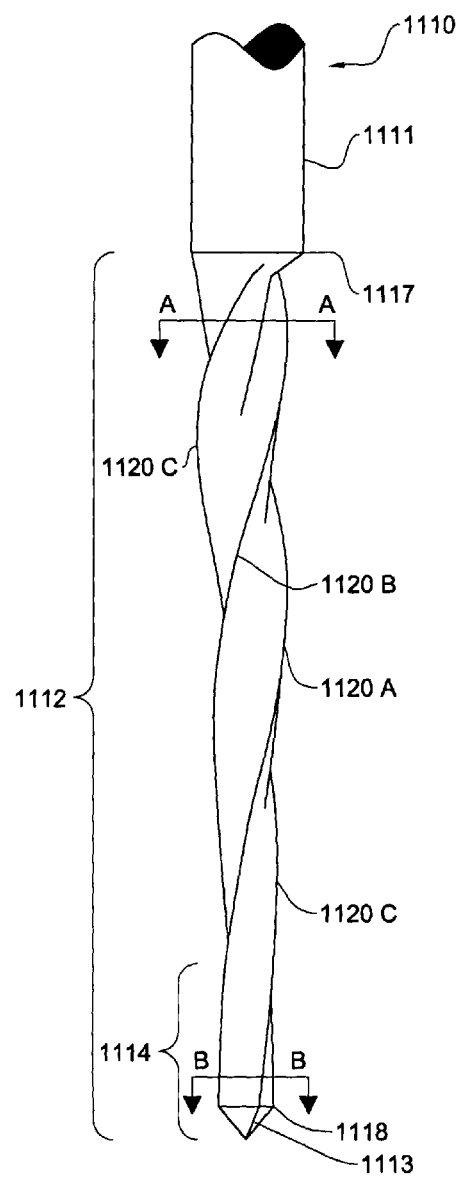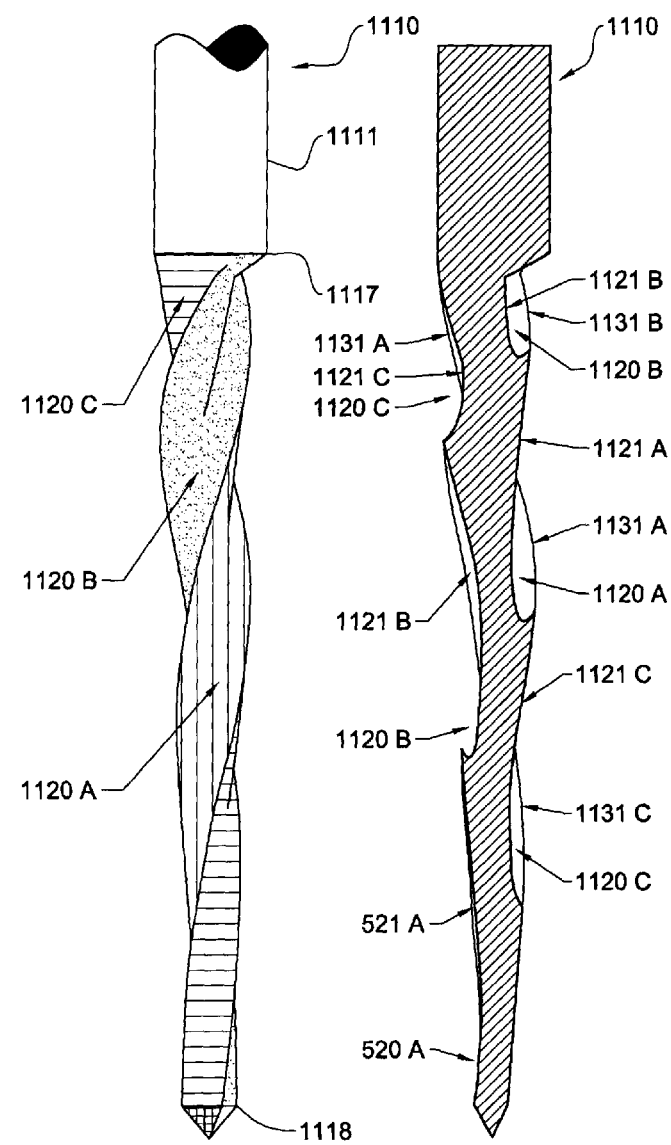
FIG. 76 FIG. 77 FIG. 78

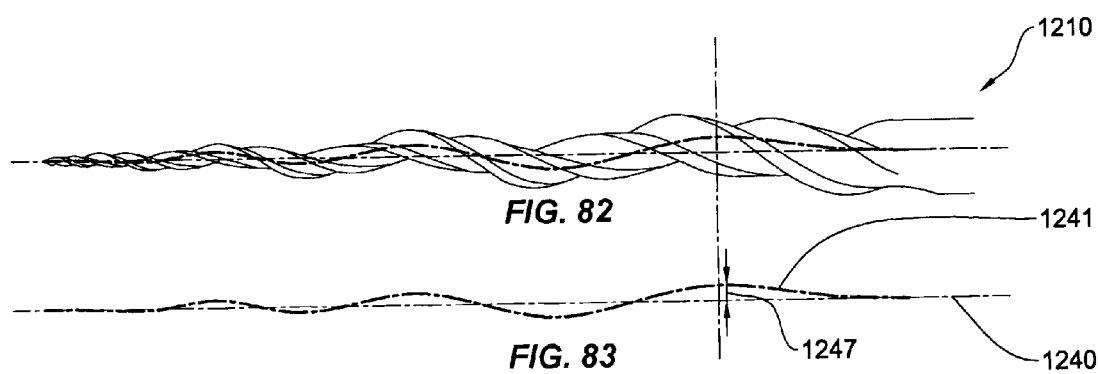
FIG. 82
FIG. 83
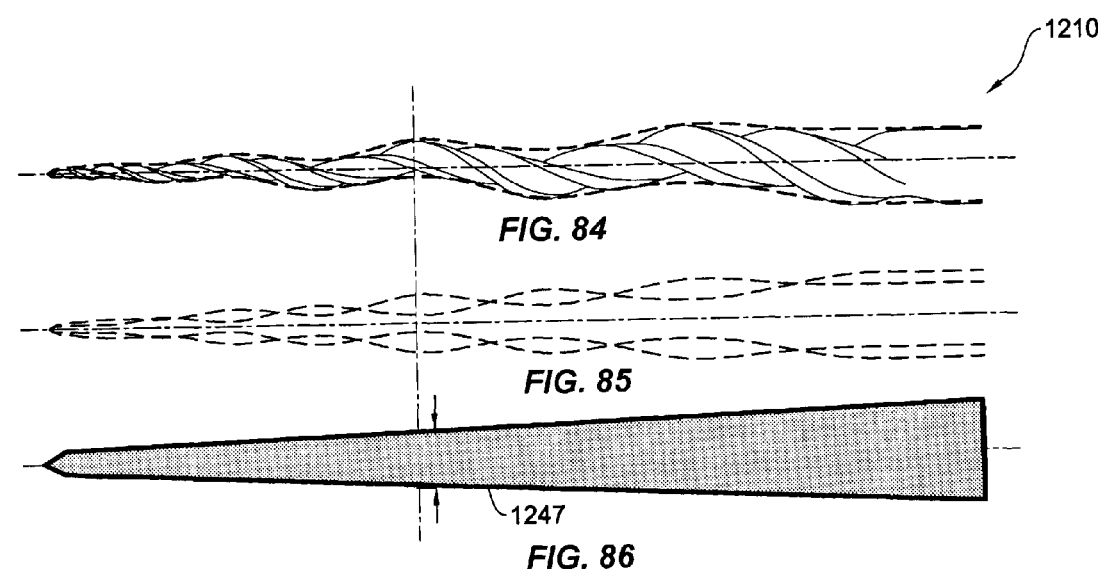
FIG. 84
FIG. 85
FIG. 86

PRECESSIONAL DRILLING AND REAMING

CROSS-REFERENCE TO RELATED APPLICATIONS

This application claims priority to U.S. Provisional Application No. 61/868,276, filed Aug. 21, 2013, and U.S. Provisional Application No. 61/899,705, filed Nov. 4, 2013. The disclosures of the prior applications are considered part of (and are incorporated by reference in) the disclosure of this application.

BACKGROUND

1. Technical Field

This document relates to drills and/or reamers and methods for their use. For example, this document relates to novel drills and/or reamers that are well-suited for making holes in a variety of materials including, but not limited to, metals, ceramics, glass, wood, plasterboard, plastics, stone, composites, synthetics, silicon or multi-layered or hybridized substrates. In some embodiments, these drilling devices have some centers of mass that are offset from the axis of rotation. Accordingly, these drills and/or reamers may rotate and cut using a precessional pattern of motion. Precessional cutting devices will display a mechanical wave pattern in relationship to the longitudinal axis of the device. If the cutting device is fabricated from a flexible material, for example Nickel-Titanium, bodily deflection of the device may result during rotation.

2. Background Information

Industrial drills and/or reamers are cutting tools used to create cylindrical or tapered holes. Referring to FIGS. 7 and 8, a typical conventional drill or bit 204 is provided. Such a conventional drill 204 usually cuts with a circular cross-sectional profile defined by rotation of cutting edges 220 and 240. Conventional drill 204 includes a shank 203, a working body 201, and a sharp cutting tip with lips 202 that is usually conical in shape. The tip engages the work surface via sufficient axial torque to create a hole. The tip is confluent with the working body 201 of the drill 204. The working body 201 includes one or more helical flutes 230 and 250 that revolve around the central axis of the drill 204. The flutes 230 and 250 also define the leading or cutting edges 220 and 240 respectively, which are followed by margins 221 and 241 and/or the radial lands 223 and 243. In some examples, the radial lands 223 and 243 include body diameter clearance areas 225 and 245 and heels 224 and 244 respectively. The clearance areas or angles and flutes accommodate the cut chips and hauls the debris via the Archimedes principle or screw action. The flutes 230 and 250 are bridged by a metal core called the web 211.

The most common drill used in industry is known as a twist drill. Twist drill designs were described as early as Hartshorn (1882), and modified by Hanson (1904), Kallio (1960), Kim (1980) and others, and are substantially, but not exclusively, end cutting drills.

Still referring to FIGS. 7 and 8, the degree of twist of the helical flutes 230 and 250 affects the drill's 204 cutting and chip-removal properties, and is referred to as the helical angle 206, which is a measurement of the number of degrees from a perpendicular to the central axis of the drill 204. The radial lands 223 and 243, which are portions of the drill body that are not cut away by the flutes 230 and 250, create friction as the lands 223 and 243 rub against the sides of the hole. A completely cylindrical twist drill encounters greater and greater friction and axial resistance as the device advances, which can cause premature wear and often damages the drill and/or work piece. One objective of a drill design may be to improve penetration rates, which improves drill productivity. Thus, to mitigate this friction and resistance, many modern designs feature a small degree of back taper 205. Although back taper 205 is useful and a standard feature is many drill designs, back taper 205 does not completely solve the aforementioned problems of friction and axial resistance.

An additional set of problems arise from "self-excited" or "regenerative" vibrations in hole making. One form of these vibrations is known as chatter, which results from torsional-axial coupling, and is an inherent feature of many twist drills. As the drill turns or cuts, a torsional load is placed on the cutting edges causing the drill to unwind or unravel. As the drill unwinds, its axial length is increasing. This extension, however, is resisted by the downward thrust of the drill and by the drill's own torsional inertia or stiffness. Thus, a back and forth axially flexure occurs, and often manifests an irregular or wavy surface at the base of the cut (e.g., see FIG. 2). As the drill continues to rotate, it collides with these waves, and the waviness and oscillation both grow more severe. Each drill and spindle can produce a resonance or frequency that is characteristic of that system. The operator often describes this resonance as a pecking or jack-hammer effect, which creates premature tool wear, and can fracture the tool and/or damage the work piece and the machine components.

Some of the suggestions to mitigate the effects of high frequency chatter that have been offered include: 1) increased web thicknesses; 2) decreased lip relief at the tip; 3) increased feed rates; and 4) decreased helix angles. If the web is thicker, the tool will be stiffer and should chatter less. A drill with a wider lip may rub more against the bottom of the hole creating more friction, further reducing chatter. Increasing the penetration rate relative to the rpms may necessarily induce more rubbing and more friction, which may further stabilize the device. A narrower or flatter helical angle may create a greater mass axis and the drill may be stiffer and less likely to unwind. While all of these suggestions may mitigate chatter to some extent, they may simultaneously serve to reduce the cutting efficiency of the drill and/or reamer and the cutting system itself.

Another form of regenerative vibration in hole making is a lower frequency vibration that produces holes that are asymmetrical or out-of-round. While high frequency vibrations are producing chatter, this low frequency vibration is encountered as the drill sways back and forth much like a pendulum and begins to trace out a cone-shaped volume. As the cut continues, this low-frequency vibration also creates waves which amplify the severity of the vibration and a lobulated form in the hole making process emerges. A two fluted twist drill will often produce a hole that has three lobes (e.g., see FIG. 3), but larger numbers of lobes are possible. Interestingly, the positions of the lobes rotate as the depth increases. Although the center of any one lobe may correspond to the drill size, the resultant lobulated space does not, making assembly using fasteners corresponding to the size of the drill less effective.

Some of the suggestions to mitigate the effects of low frequency vibration that have been offered include: 1) increased stiffness of the drill by increasing the thickness of the web or lowering the helical angle of the flutes; 2) increased numbers of flutes; and 3) increased contact of the margin of the radial land. Adding additional cutting points may improve the orientation of the body of the drill and provide better opportunity for roundness. In some cases, increasing the width of the margin or increasing the number of margins on the tool itself or both may be helpful. There are twists drill available, with two and three lands per flute, all of which serve to dampen the effect of the vibration in the same way that reducing lip relief dampens chatter. Again, while all of these suggestions may serve to mitigate low frequency vibrations, they may simultaneously serve to reduce the cutting efficiency of the drill and/or reamer and the cutting system itself.

The web of a standard twist drill approaches 20% of the diameter of the drill itself. An increase in the web thickness of up to 40% of the drill diameter has been recommended to eliminate high frequency vibrations (chatter) and low frequency vibrations (sway). Unfortunately, an increase in web thickness from 20% to 40% will require four times more axial force to operate the drill. A precessional cutting device such as the one described herein, will require less web thickness (inherent to the design and manifest in the performance) and thereby reducing the axial force required for drill penetration improving overall efficiency and productivity of the system.

A further consideration is the configuration of the chisel tip in wide web drills. The chisel tip is the edge of the drill's end across the web that connects the cutting lips. The formation of a chip at the chisels edge is dependent on the rake angle. The smaller the rake angle the more efficient the cutting tip can be. Chip formation can still occur with a rake angle up to 40 degrees. Unfortunately, drills with wide webs (between 20-40% of the diameter of the drill) have the highest rake angle and are the least efficient. Attempts to thin the webs at the tip can only lead to premature drill wear and safety risks, and can create asymmetry in hole roundness. Another advantage of better chip formation is heat dissipation. A larger chip will absorb more heat, carrying it away from the drill and the substrate itself. Thus, within practical limits, maintaining the narrowest web possible should be the focus of any innovative drill design.

Fredrick Taylor described machine tool vibrations in 1907. However, most of the suggestions offered for mitigating machine tool vibrations have only come in the last few decades.

In attempt to resolve the problems relating to regenerative vibrations or chatter and hole asymmetry Freidli, Petigant, and Salomon (U.S. Pat. No. 4,913,603 issued Apr. 3, 1990) proposed a modification to the traditional twist design by spacing the flutes unequally around a dual web. Krieg, Gey, and George (U.S. Pat. No. 8,734,068 issued May 27, 2014) proposed a similar concept whereby the flutes were spaced unequally and whereby the web was asymmetrical.

In an effort to improve the roundness and quality of holes drilled in fiber-reinforced composites (e.g., stacked substrates), a number of inventors have described a system of cutting, collectively referred to as orbital drilling or cutting. For example, Eriksson (U.S. Pat. No. 5,641,252 issued Jun. 24, 1997) proposed a system whereby the body of the drill, which is rotating axially, is directed eccentrically circumscribing or outlining a round space. Although he does not specify the mechanism used in directing the drill eccentrically, it is accomplished with a drill that is substantially smaller than the hole itself. Tangquist, Lennart, and Backman (U.S. Pat. No. 5,685,674 issued Nov. 11, 1997) and Zackrisson, Eriksson, Jonsson, Wolf, and Roswall (U.S. Pat. No. 6,773,211 issued Aug. 10, 2004) proposed similar systems. These inventors disclosed a machine that purportedly accomplishes these objectives, and that is useful for cutting fiber-reinforced composites and metal. Again, such systems relied on a rotary drill whereby the body of the drill is displaced at a significant distance from the central axis of the hole in the work piece cutting orthogonally.

In another effort to improve roundness, Shiga, Matsushita, Fukui, Yamashita, Shimizu (U.S. Pat. No. 5,312,208 issued May 17, 1994) proposed a device called a burnishing drill or reamer, which displayed more than one diameter. A first pair of cutting edges about the first diameter extend radially outward from the foremost end of the drill, inclining axially in the rearward direction with a first cutting angle and a second pair of cutting edges about the second diameter. Its maximum external diameter is larger than the external diameter of the first cutting edges, also extending radially outward from the foremost end of the drill and inclines axially in the rearward direction with a second cutting angle. This would best be described as a combination drill and reamer.

Halley, Luner, Young, and Bayly (U.S. Pat. No. 6,379,090 issued Apr. 30, 2002) described a force balanced irregular pitch reamer that is purportedly well-suited for precision operations requiring small tolerances and wherein precision in roundness of the drilled space is required. More specifically, a reamer is described having a plurality of cutting teeth that extend outwardly at non-uniform intervals around the body portion of the drill or reamer. Each tooth generates a distinct cutting force vector. The summation of these vectors purportedly produces a balanced reamer and provides a finished hole with improved roundness. Reamers, however, are usually used in conjunction with a pilot hole and would, and therefore require a second step.

Davancens and Whinnem (U.S. Pat. No. 8,714,890 issued May 6, 2014) proposed a drill with at least two cutting flutes. The first radial distance is different from the second radial distance as measured within a first plane normal to the central axis. The length of the first cutting edge is longer than the length of the second cutting edge such that during orbital drilling the first cutting edge removes a majority of the material being machined. The first cutting edge is made of polycrystalline diamond, and the second cutting edge is made of cubic boron nitride. This method was also devised to facilitate drilling hybridized or stacked material (i.e., layers of discontinuous materials, for example, carbon fiber composite, and titanium and/or aluminum, and/or steel).

Further examples of the prior art are provided by the following patents: U.S. Pat. No. 4,149,821; U.S. Pat. No. 4,190,386; U.S. Pat. No. 4,338,050; U.S. Pat. No. 4,659,264; U.S. Pat. No. 4,740,121; U.S. Pat. No. 4,757,645; U.S. Pat. No. 4,889,456; U.S. Pat. No. 5,049,011; U.S. Pat. No. 5,312,208; and U.S. Pat. No. 5,685,674.

SUMMARY

This document provides rotary cutting instruments that may be used for industrial drilling and/or reaming. The terms "cutting instrument" and "cutting device" as used herein refers to multiple types of devices including drills, reamers, devices that function as both a drill and a reamer, and the like. In particular, this document provides cutting instrument designs and methods to mitigate or eliminate chatter and provide symmetric round holes. In some embodiments, these cutting instruments cut precessionally. One characteristic of precessional motion cutting is that not all portions of the cutting edges are in simultaneous contact with the substrate material being cut. As a result, these cutting instruments are lighter and require less axial pressure or down force and less energy to operate than other cutting devices. An example use for the cutting devices provided herein is drilling and/or reaming of round holes in materials such as wood, plastics, plaster, fiberglass, silicon, or carbon fiber. Other example uses include harder and/or more brittle materials such as glass or ceramics, which are challenging due to the material's poor edge strength and the substantial load that is required to create the perforation. Other example uses for the cutting devices provided herein include materials that are extremely hard and highly predisposed to high frequency and lower frequency vibrations such as various types of metals. Still further uses are envisioned within the scope of this disclosure.

In one implementation, a cutting instrument includes a shank configured to be releasably attachable to a motor to rotate the cutting instrument about an axis of rotation; and a drill body extending from the shank. The drill body includes a shank end where the drill body extends from the shank and a free end at an end of the drill body that is opposite of the shank end. The drill body includes a cutting portion between the shank end and the free end. The drill body comprises a plurality of transverse cross-sections. Each transverse cross-section of the drill body has a center of mass, and the drill body has a center of mass path that is defined by the centers of mass of all transverse cross-sections of the body. A center of mass of a transverse cross-section at the shank end is offset from the axis of rotation, and a center of mass of a transverse cross-section at the free end lies on or near the axis of rotation.

Such a cutting instrument may optionally include one or more of the following features. A distance of the center of mass from the axis of rotation may decrease linearly from the shank end to the free end. The center of mass of the transverse cross-section at the free end may lie on the axis of rotation. The center of mass path may comprise a three dimensional spiral around the axis of rotation. The drill body may have a substantially constant diameter from the shank end to the free end. The drill body may be tapered from the shank end to the free end such that the shank end has a larger cutting diameter than the free end. The drill body may be tapered from the free end to the shank end such that the free end has a larger cutting diameter than the shank end. The drill body may include a transverse cross-section that is asymmetrical, bisymmetrical, symmetrical, triangular, biangular, or quadrilateral. The tapered body may include a first transverse cross-section and a second transverse cross-section, wherein the first transverse cross-section has a first geometry, and wherein the second transverse cross-section has a second geometry different from the first geometry. The tapered body may cut along a dual axis; the dual axis comprising a first axis corresponding the central axis of rotation and a second axis corresponding to an offset mass path which rotates around the central axis. The cutting instrument may comprise a chisel tip at the free end of the drill body. The chisel tip may subtend an angle of greater than 40 degrees. An end of the chisel tip may be on the axis of rotation. A pointed end of the chisel tip may be offset from the axis of rotation. The chisel tip may include a plurality of inclined planes at substantially equal inclination. The chisel tip may include a first inclined plane and a second included plane with a different inclination than the first inclined plane. A portion of the drill body near the free end may have blunted cutting edges. The cutting instrument may be comprised of a nickel-titanium alloy. The flutes of the cutting instrument may have differing degrees of diametrical taper when viewed in longitudinal cross-section. The cutting instrument may have at least two regions of differing diametrical taper. The cutting portion may be coated with one of the group consisting of diamond, amorphous diamond, diamond compact bits, and diamond-like carbon. The cutting portion may include radial lands without margins. The cutting portion may be coated with one of the group consisting of titanium nitride, titanium aluminum nitride, titanium carbon nitride, zirconium nitride, and black oxide. The cutting instrument may have at least one longitudinal irrigation passage which passes through a shank portion of the cutting instrument and transverses a core or web of the drill exiting laterally and distally, wherein the passage is configured to allow flow of irrigation fluid to a lateral perimeter or tip of the cutting instrument. The cutting portion may include radial lands with one or more margins. The cutting instrument may consist of one type of material. A portion of the cutting body at the free end may comprise a first type of material, and other portions of the cutting body comprise a second type of material that is different than the first type of material.

In another implementation, a method of cutting a space in a material includes: driving, using a motor, a cutting instrument; contacting, while driving the cutting instrument, the free end of the cutting instrument against the material; and extending, while driving the cutting instrument, at least a portion of the cutting instrument into the material to remove portions of the material to thereby create the space in the material. The cutting instrument may include a drill body extending from the shank. The drill body may include a shank end where the drill body extends from the shank and a free end at an end of the drill body that is opposite of the shank end. The drill body may include a cutting portion between the shank end and the free end. The drill body may comprise a plurality of transverse cross-sections. Each transverse cross-section of the drill body has a center of mass, and the drill body has a center of mass path that is defined by the centers of mass of all transverse cross-sections of the body. A center of mass of a transverse cross-section at the shank end may be offset from the axis of rotation, and a center of mass of a transverse cross-section at the free end may lie on or near the axis of rotation.

Such a method of cutting a space in a material may optionally include one or more of the following features. The extending the cutting instrument may comprise precessional motion of the cutting instrument. The rotating the cutting instrument includes may cause the cutting instrument to form sinusoidal waves within the space. The rotating the cutting instrument may include causing the cutting instrument to form helical waves within the space. The cutting instrument may be comprised of a super-elastic material. The driving the cutting instrument may comprise reciprocating the cutting instrument rotationally about the axis of rotation. The driving the cutting instrument may comprise reciprocating the cutting instrument longitudinally along the axis of rotation. The driving the cutting instrument may comprise reciprocating the cutting instrument rotationally about the axis of rotation and longitudinally along the axis of rotation.

In another implementation, a cutting instrument includes: a shank configured to be releasably attachable to a motor to rotate the cutting instrument about an axis of rotation; and a drill body extending from the shank. The drill body includes a shank end where the drill body extends from the shank and a free end at an end of the drill body that is opposite of the shank end. The drill body includes a cutting portion between the shank end and the free end. The drill body comprises a plurality of transverse cross-sections. Each transverse cross-section of the drill body has a center of mass. The drill body has a center of mass path that is defined by the centers of mass of all transverse cross-sections of the body. A center of mass of a transverse cross-section at the shank end is offset from the axis of rotation and a center of mass of a transverse cross-section at the free end is offset from the axis of rotation. A distance from a center of mass of each transverse cross-ssection between the shank end and the free end is offset from the axis of rotation by a substantially consistent distance.

Such a cutting instrument may optionally include one or more of the following features. The center of mass path between the shank end and the free end may comprise a helix.

At least a portion of the center of mass path may be linear. A distance of the center of mass from the axis of rotation may decrease linearly from the shank end to the free end. The center of mass path may comprise a three dimensional spiral around the axis of rotation. The drill body may have a substantially constant diameter from the shank end to the free end. The drill body may be tapered from the shank end to the free end such that the shank end has a larger cutting diameter than the free end. The drill body may be tapered from the free end to the shank end such that the free end has a larger cutting diameter than the shank end. The drill body may include a transverse cross-section that is asymmetrical, bisymmetrical, symmetrical, triangular, biangular, or quadrilateral. The tapered body may include a first transverse cross-section and a second transverse cross-section, wherein the first transverse cross-section has a first geometry, and wherein the second transverse cross-section has a second geometry different from the first geometry. The tapered body may cut along a dual axis; the dual axis comprising a first axis corresponding the central axis of rotation and a second axis corresponding to an offset mass path which rotates around the central axis. The cutting instrument may comprise a chisel tip at the free end of the drill body. The chisel tip may subtend an angle of greater than 40 degrees. An end of the chisel tip may be on the axis of rotation. A pointed end of the chisel tip may be offset from the axis of rotation. The chisel tip may include a plurality of inclined planes at substantially equal inclination. The chisel tip may include a first inclined plane and a second included plane with a different inclination than the first inclined plane. A portion of the drill body near the free end may have blunted cutting edges. The cutting instrument may be comprised of a nickel-titanium alloy. The flutes of the cutting instrument may have differing degrees of diametrical taper when viewed in longitudinal cross-section. The cutting instrument may have at least two regions of differing diametrical taper. The cutting portion may be coated with one of the group consisting of diamond, amorphous diamond, diamond compact bits, and diamond-like carbon. The cutting portion may include radial lands without margins. The cutting portion may be coated with one of the group consisting of titanium nitride, titanium aluminum nitride, titanium carbon nitride, zirconium nitride, and black oxide. The cutting instrument may have at least one longitudinal irrigation passage which passes through a shank portion of the cutting instrument and transverses a core or web of the drill exiting laterally and distally, wherein the passage is configured to allow flow of irrigation fluid to a lateral perimeter or tip of the cutting instrument. The cutting portion may include radial lands with one or more margins. The cutting instrument may consist of one type of material. A portion of the cutting body at the free end may comprise a first type of material, and other portions of the cutting body comprise a second type of material that is different than the first type of material.

In another implementation, a cutting instrument includes: a shank configured to be releasably attachable to a motor to rotate the cutting instrument about an axis of rotation; and a drill body extending from the shank. The drill body includes a shank end where the drill body extends from the shank and a free end at an end of the drill body that is opposite of the shank end. The drill body includes a cutting portion between the shank end and the free end. The drill body comprises a plurality of transverse cross-sections. Each transverse cross-section of the drill body has a center of mass, and the drill body has a center of mass path that is defined by the centers of mass of all transverse cross-sections of the body. A center of mass of a transverse cross-section at the shank end is offset from the axis of rotation, and a center of mass of a transverse cross-section at the free end is offset from the axis of rotation.

Such a cutting instrument may optionally include one or more of the following features. The center of mass path comprises a three dimensional spiral that revolves around the axis of rotation. At least a portion of the center of mass path may be substantially linear. At least a portion of the center of mass path may be curved. All centers of mass of each transverse cross-section may be in a common plane. A first portion of the center of mass path may be offset from the axis of rotation by a substantially constant distance, and a second portion of the center of mass path may be offset from the axis of rotation by a distance that decreases monotonically. The drill body may include a transverse cross-section that is asymmetrical, bisymmetrical, symmetrical, triangular, or quadrilateral shaped. The cutting portion may include radial lands with one or more margins. The cutting instrument may consist of one type of material. A portion of the cutting body at the free end may comprise a first type of material, and other portions of the cutting body comprise a second type of material that is different than the first type of material. Flutes of the cutting instrument may have differing degrees of diametrical taper when viewed in longitudinal cross-section. The cutting instrument may have at least two regions of differing diametrical taper. The cutting portion may include radial lands without margins. The cutting instrument may comprise a chisel tip at the free end of the drill body. A pointed end of the chisel tip may be offset from the axis of rotation. The chisel tip may include a first inclined plane and a second included plane with a different inclination than the first inclined plane.

Particular embodiments of the subject matter described in this document can be implemented to realize one or more of the following advantages. The cutting devices provided herein can create precision round, burr-less, and chip-free holes, without requiring the two-step process of drilling and reaming as with other techniques. The precessional cutting devices are also well-suited to drilling combinations of materials (e.g., stacked or hybridized materials). A precessional cutting instrument that is somewhat flexible and that has a center of mass offset from an axis of rotation may swing out from the axis of rotation as the instrument is rotated at high speeds. If the instrument is configured to bend an equal amount at each angle of rotation, the inner diameter of a space can be contacted by the instrument and uniformly machined. The instrument can be made to have a smaller diameter than the space that requires machining. Other advantages offered by the precessional drill designs include the intermittent contact of the lands and cutting edges of the drill with the material itself. In such a manner, the hole space can be enlarged more efficiently, and the material is kept cooler to avoid or reduce thermal expansion or deformation of the material. Intermittent contact can also facilitate irrigation, which can also improve the cutting efficiency of the instrument.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIGS. 14-16 depict another example two-sided rotary offset drill and/or reamer. This two-sided rotary offset drill and/or reamer embodiment is slightly wider at the shank end than at the tip end, thereby having a tapered cutting envelope. This two-sided rotary offset drill can be used advantageously as a pilot drill, drill and/or reamer, and may be useful in a variety of applications.

FIGS. 22-24 show an example three-sided rotary offset drill and/or reamer. In some embodiments, this style of instrument cuts within a tapered cutting envelope.

FIGS. 28-30 show views of an example three-sided rotary offset drill and/or reamer that is slightly wider at the tip than at the shank end. In some embodiments, this style of instrument defines a cylindrical cutting envelope.

FIGS. 37-39 show views of another example three-sided rotary offset drill and/or reamer that is slightly wider at the tip than at the shank end. In this embodiment, the centers of mass of all transverse cross-sections along the working length are offset from the axis of rotation, while the point of the tip coincides with the axis of rotation. This device may have a number of applications, and may be particularly useful as a reamer. In some embodiments, this style of instrument defines a cylindrical cutting envelope.

FIGS. 43 and 44 show the active tip of example drills that will remain substantially centered when in use.

FIGS. 45-47 show views of an example offset four-sided offset drill and/or reamer. The splines are angular and emanate from the core radially.

FIGS. 51-53 and 54-56 show views of an example four-sided rotary offset drill and/or reamer that is slightly wider at the tip than at the shank end, and that has a transverse cross-section in the form of a parallelogram. In this embodiment, the center of mass at the shank is offset from the axis of rotation, and the center of mass at the tip coincides with the axis of rotation. This instrument can be used is a variety of applications. In some embodiments, this style of instrument defines a cylindrical cutting envelope.

FIGS. 76-78 show views of another example three-sided rotary offset drill and/or reamer. The tip end is well-suited to creating a pilot hole, while the upper portion of the device will cut a cylindrical or tapered hole precessionally.

FIG. 82 shows an elongate view of an example cutting instrument that has a working portion with centers of mass that are offset from the axis of rotation along the working portion to the tip that is centered on the axis of rotation.

FIG. 83 represents the center of mass path (or mass axis) of the drill and/or reamer of FIG. 12A.

FIGS. 84-86 depict the cutting envelope of the cutting instrument of FIG. 82 that cuts with a precessional motion.

Like reference numbers represent corresponding parts throughout.

DETAILED DESCRIPTION

Figure 1:
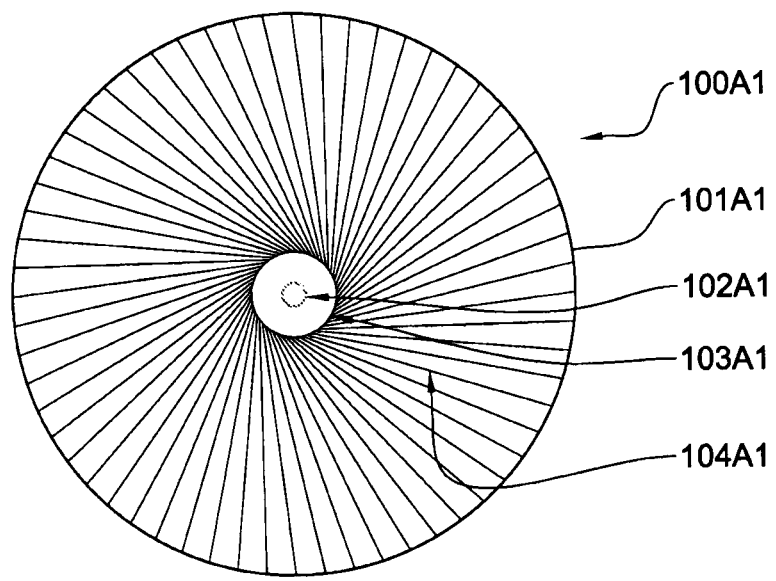
FIG. 1 depicts the irregular wave-like surface produced at the base of a drilling cavity resulting from chatter.

This document provides rotary precessional-motion cutting devices that may be used for industrial drilling and/or reaming. The drilling instruments provided herein have at least some transverse cross-sections (perpendicular to the axis of rotation) with centers of mass that are offset from the drill's axis of rotation. The offset center of mass may allow the drills to generate precessional motion (also referred to herein as mechanical waves) when in use, whereby not all portions of the cutting edges are in simultaneous contact with the substrate material being cut. In some embodiments, the cutting tool designs and methods provided herein may mitigate or eliminate chatter and provide symmetrically round holes. The cutting devices provided herein may be lighter and require less axial pressure or down force and less energy to operate than other cutting devices. An example use for the cutting devices provided herein is drilling and/or reaming of round holes in materials such as wood, plastics, plaster, fiberglass, silicon, or carbon fiber. Other example uses include harder and/or more brittle materials such as glass or ceramics, which are challenging due to the material's poor edge strength and the substantial load that is required to create the perforation. Other example uses for the cutting devices provided herein include materials that are extremely hard and highly predisposed to high frequency and lower frequency vibrations such as various types of metals. Still further uses are envisioned within the scope of this disclosure.

A great deal of mathematics and engineering has been dedicated to modeling, studying and solving the problems associated with high frequency and low frequency vibrations during drilling in attempt to improve drilling efficiency. These include the work of Yang and Jaganathan (2002), Stone and Askari (2002), Hsieh (2005) and Gupta, Ozdoganlar, Kapoor, and DeVor (2003). Using the simplest model practical, Kessentini et al. used a two-degrees of freedom model to simulate the vibration of twist drills in an x and y direction. The z-axis was the longitudinal axis of rotation. The model was used to describe the relative tool position in time (t). The algorithm:

$$r(t) = \sqrt{x^2(t) + y^2(t)}$$

was used to calculate the radial vibration of the drill deduced directly about x(t) and y(t). This equation is related to the Perpendicular-Axis Theorem, which correlates the inertia of a thin lamina of an object (e.g., cylindrical drill body) with coordinates x and y. If inertia (I) is defined as $I = mr^2$, then the total inertia of the lamina rotating around the z-axis can be described as $I_z = I_x + I_y$.

When working in Cartesian coordinates the moment of inertia (Iz) for a planar body is:

$$I_z = \int (x^2 + y^2) dm = \int x^2 dm + \int y^2 dm = I_y + I_x$$

Although mathematical algorithms are useful in modeling, a more simplistic approach in understanding the value of precessional cutting and offset designs is the evaluation of the moment of inertia of a cylinder of radius r and its associated radius of gyration $R_g$ making the explanation of changes in inertia become more understandable.

Figure 4:
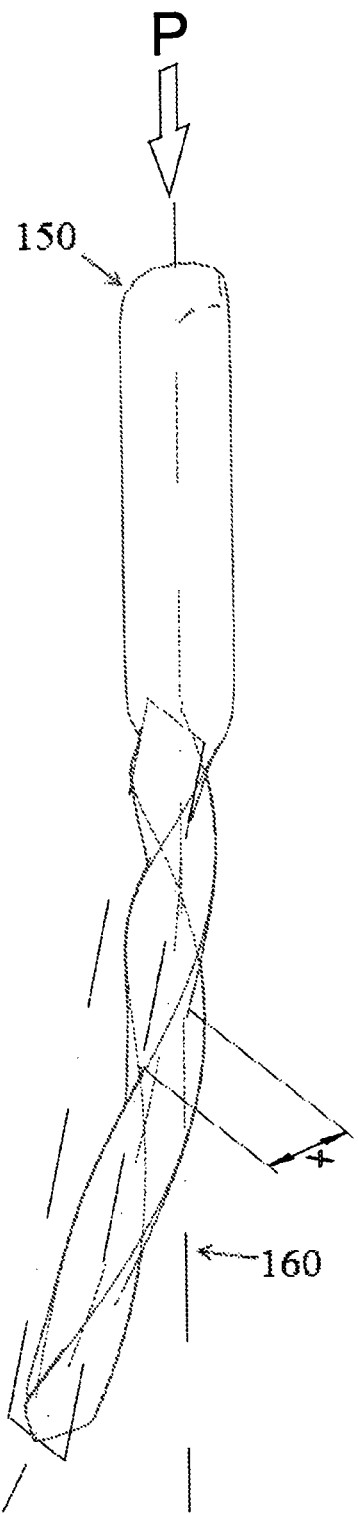
FIG. 4 depicts a drill body which is bending or buckling via axial (compressive) force.

The radius of gyration $R_g$ is a convenient parameter, providing a measure of the resistance of a cross-section to lateral buckling as shown by the displacement x in FIG. 4, or an indication of the stiffness of a section based on the shape of the cross-section when used under pressure or compression P (for example a cylindrical drill body).

In general, the member will bend in the thinnest plane and in an area of least support and is expressed by the formula:

$$R_g = \sqrt{\frac{I}{A}}$$

Where I=moment of area, and A=area of material in the cross-section.

Thus, the radius or gyration, and thereby the resistance to buckling and/or distortion, increases as the moment of inertia from a given mass in a given coordinate system increases. The moment of inertia can be calculated for any rigid body that is undergoing a physical rotation around a fixed axis. It is based not only on the physical shape of the object and its distribution of mass, but also the specific configuration of how the object is rotating. So the same object rotating in different ways would have a different moment of inertia in each situation. The general formula:

$$I_P = \sum_{i=1}^{N} m_i r_i^2$$

represents the most basic concept for the moment of inertia. Basically, for any rotating object, the moment of inertia can be calculated by taking distance of each particle from the axis of rotation (r in the equation), squaring that value (the $r^2$ term), and multiplying it times the mass of that particle. That is done for all of the particles that make up the rotating object, and combining the results gives the moment of inertia.

The consequence of this formula is that the same object gets a different moment of inertia value, depending on how it is rotating and where it is located in space. A new axis of rotation and/or a new centroid ends up with a different formula, even if the physical shape of the object remains the same. Thus, the further the x and y coordinates for r move away from the axis of rotation and/or the centroid the larger the value of rotational inertia I.

In the case of a solid cylinder, the expression for the moment of inertia can be extrapolated by viewing thin lamina and is expressed as:

$$I = \int_0^M r^2 \, dm$$

where M is the mass and dm is the mass differential. Again, from the equations above it becomes clear that the moment of inertia increases as the radius of the centroid increases.

Figure 5:
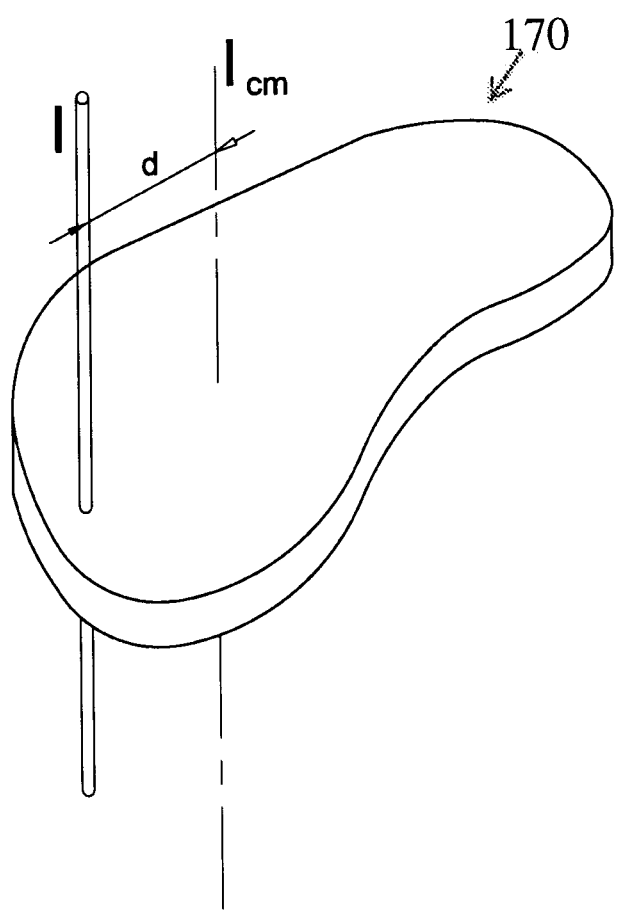
FIG. 5 depicts a thin lamina of an offset drill body that is rotating around the axis of rotation.

The Parallel-Axis theorem, also known as the Huygens-Steiner theorem, which was employed in the 17th century to describe planetary motion, is especially useful for evaluating the improvement in inertia using offset centers of mass. A lamina of an offset cylindrical drill body is shown in FIG. 5. One can write the formula for the parallel-axis theorem in its simplest form as $I=Icm+md^2$. Here Icm is the moment of inertia of a body of mass m with respect to a line through its centroid cm, I is the total moment of inertia with respect to a line parallel to the central axis or axis of rotation, and d is the distance between the two lines. Thus, for a givien lamina, total inertia I (and the resistance to bending and distortion) can be improved by improvements in both the mass of a cross-section and an exponential increase in the distance from the central axis to the centroid.

Thus, improvements in torsional inertia (and resistance to bending) can be accomplished by a modest offset of the cross-section area away from the central axis without substantially increasing the mass or (in the case of a twist drill) the thickness of the core or web.

In some embodiments, the drills and/or reamers described herein have one or more cross-sections with a centroid (center of mass) that is offset from the drill's axis of rotation. The offset center of mass allows these drills and/or reamers to generate precessional motion, and/or to form mechanical waves during rotation. The hallmark of precessional cutting devices is the intermittent contact of the cutting edges of the flutes with the walls of the substrate as it is being cut or perforated, which has the potential of reducing or eliminating chatter both in an axial and torsional direction. Unlike previous drill designs the drills and/or reamers provided herein accomplish the same functions as orbital drills, but can be used in a standard rotary drill or spindle.

Precessional drills and/or reamers can create cutting envelopes with cross-sectional areas that are larger than at least some of the cross-sectional areas of the drill or reamer itself, and are therefore lighter and require less energy to operate. They also possess wider clearance angles with improved hauling capacity, which further improves cutting efficiency.

Other advantages offered by precessional drills and/or reamers are the intermittent contact of the flutes of the device with the substrate rendering the work piece cooler and less susceptible to distortion. Intermittent contact can also facilitate higher volumes of irrigant or coolant when temperature control is mandatory, for example during perforation of ceramics, glass and silicon, also improving the cutting efficiency. Further, the drills and/or reamers described herein, when fabricated from a flexible or super-flexible alloy, can engender bodily movement or deflection, which can be particularly useful in drilling and/or reaming irregular spaces or spaces with some degree of curvature.

FIG. 1 depicts an irregular or wavy surface 104A at the base of the cut or drill cavity 100A resulting from instrument chatter as previously described.

Figure 2:
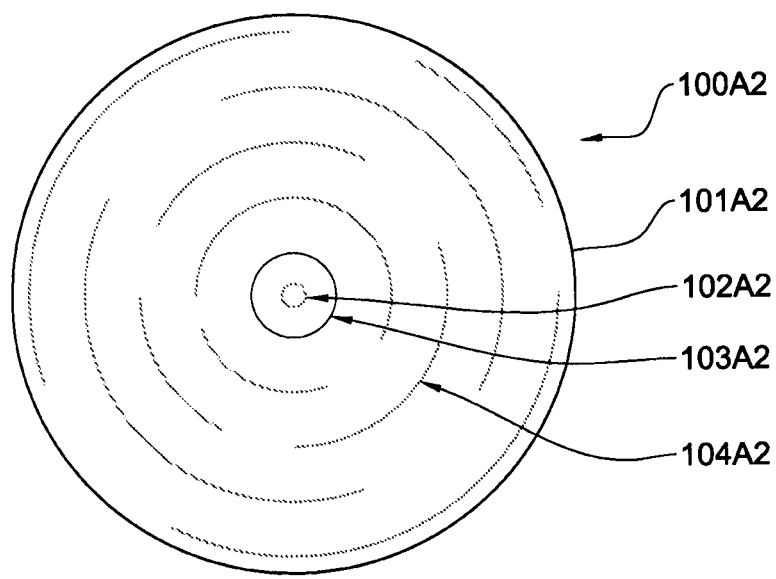
FIG. 2 depicts a regular surface produced at the base of a drilling cavity resulting from a drill that is stable and does not produce chatter.

FIG. 2 depicts a regular surface produced at the base of a drilling cavity resulting from a drill that is stable and does not produce chatter.

Figure 3:
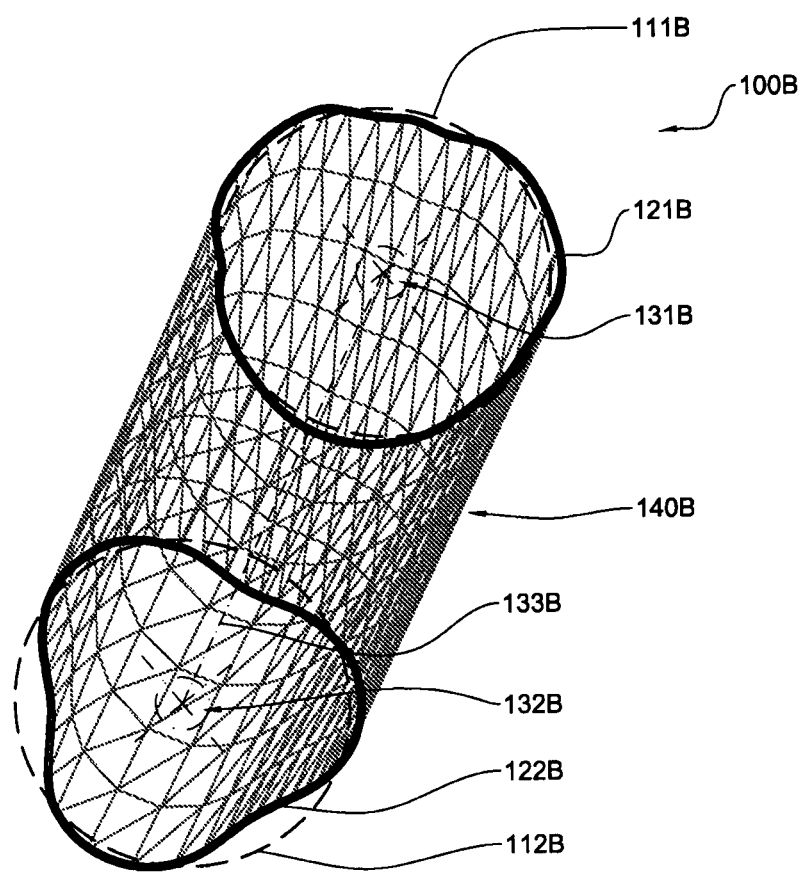
FIG. 3 depicts the irregular or lobulated contour of a drilled cavity resulting from low frequency vibrations during drilling.

FIG. 3 depicts an example of a lobulated configuration of drill cavity space 100B created as the result of lower frequency vibrations associated with sway or a pendulum like action of a cutting instrument (as previously described). The lobulated drill cavity space 100B includes, in this example, the irregular hole peripheries 121 (top of the cavity) and 122B (base of the cavity) that stand in contrast to a cylindrical hole periphery as indicated by circular hole peripheries 111B and 112B (which are centered around longitudinal axis 132B). Note that the lobulated configuration is more exaggerated at the base 122B of the cavity 100B.

FIG. 4 depicts a drill body 150 that is buckling via axial (downward or compressive) force P. The drill 150 is buckling due in part to inadequate stiffness and torsional inertia, which can be improved upon by offsetting the centroids of cross-sections from the axis of rotation 160.

FIG. 5 schematically represents a thin lamina 170 (also referred to herein as a transverse cross-section) of an offset drill body that is rotating around the axis of rotation I. It depicts the improvement in torsional inertia as the center of mass $I_{cm}$ moves further from the axis of rotation by a distance d.

Figure 6:
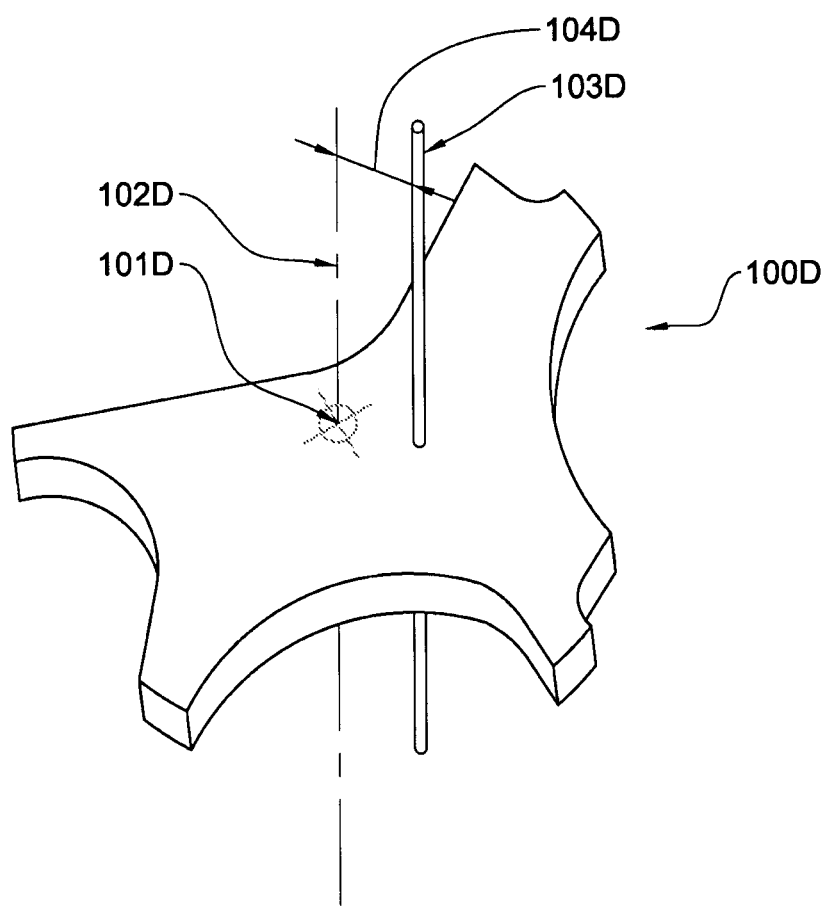
FIG. 6 depicts a lamina of a transverse cross-section of a drill body that is offset and asymmetrical.

Further considering the parallel-axis theorem, if we are viewing a lamina of a transverse cross-section of a drill body such as the offset asymmetric cross-section 100D of FIG. 6, the improvement of the inertia or this lamina at the central axis 103D is a the inertia of the center of mass 102D plus the mass of the cross-section times the square of the distance between the two axis 104D. This can be better conceptualized if we consider an example of a hammer rotating about an axis perpendicular to the handle. The further the axis of rotation extends away from the head of the hammer and toward the end of the handle the greater the cumulative or total inertia at the end of the hammers striking surface.

In this document, the term "offset" refers to a configuration of a cutting instrument (e.g., a drill, reamer, and the like) wherein the centroid of one or more transverse cross-sections of the cutting instrument are spaced apart from the axis of rotation of the cutting instrument. The combination of multiple centroids of consecutive transverse cross-sections of a cutting instrument define a "center of mass path" of the cutting instrument. As will be described further below, the center of mass path of the cutting instruments provided herein can be partially or fully offset from the axis of rotation of the cutting instruments. Additionally, offset center of mass paths, or portions thereof, can have various configurations. For example, some offset center of mass paths, or portions thereof, are linear. Some offset center of mass paths, or portions thereof, are curved (e.g., a single curve, or multiple curves such as an S-shape or sine wave). Some offset center of mass paths, or portions thereof, are helical or a cork-screw shape. It should be understood that combinations of such center of mass paths can be combined in a single cutting instrument. For example, a single cutting instrument can have one or more portions that have a center of mass path that are coincident with the axis of rotation, and one or more other portions that have a center of mass paths that are offset. Further, such one or more other portions that have a center of mass paths that are offset can have similar or dissimilar configurations. For example, a first offset center of mass path portion can be linear, while a second offset center of mass path can be curved, helical, cork-screw shaped, and the like. It should be understood that any such combinations and permutations of center-off-mass-paths are envisioned and within the scope of this disclosure.

In addition, it should be understood that the cutting instruments provided herein may be fully or may have portions that have a cylindrical profile, a tapered profile, a multi-tapered profile, and the like, and any combination and subcombination thereof. For example, some embodiments provided herein have a multi-tapered profile which means that a first portion of the cutting instrument has a diametrical taper at a first taper rate, and the cutting instrument has one or more other portions that have a diametrical taper at a rate that is different than the first taper rate. It should be understood that cutting instruments having any combination and permutation of portions with a tapered profile, a multi-tapered profile, and the like are envisioned and within the scope of this disclosure. For example, a single cutting instrument may have a first portion that has a cylindrical profile, a second portion that has a multi-tapered profile, and one or more additional portions that have a cylindrical or other shaped profile.

Figure 7:
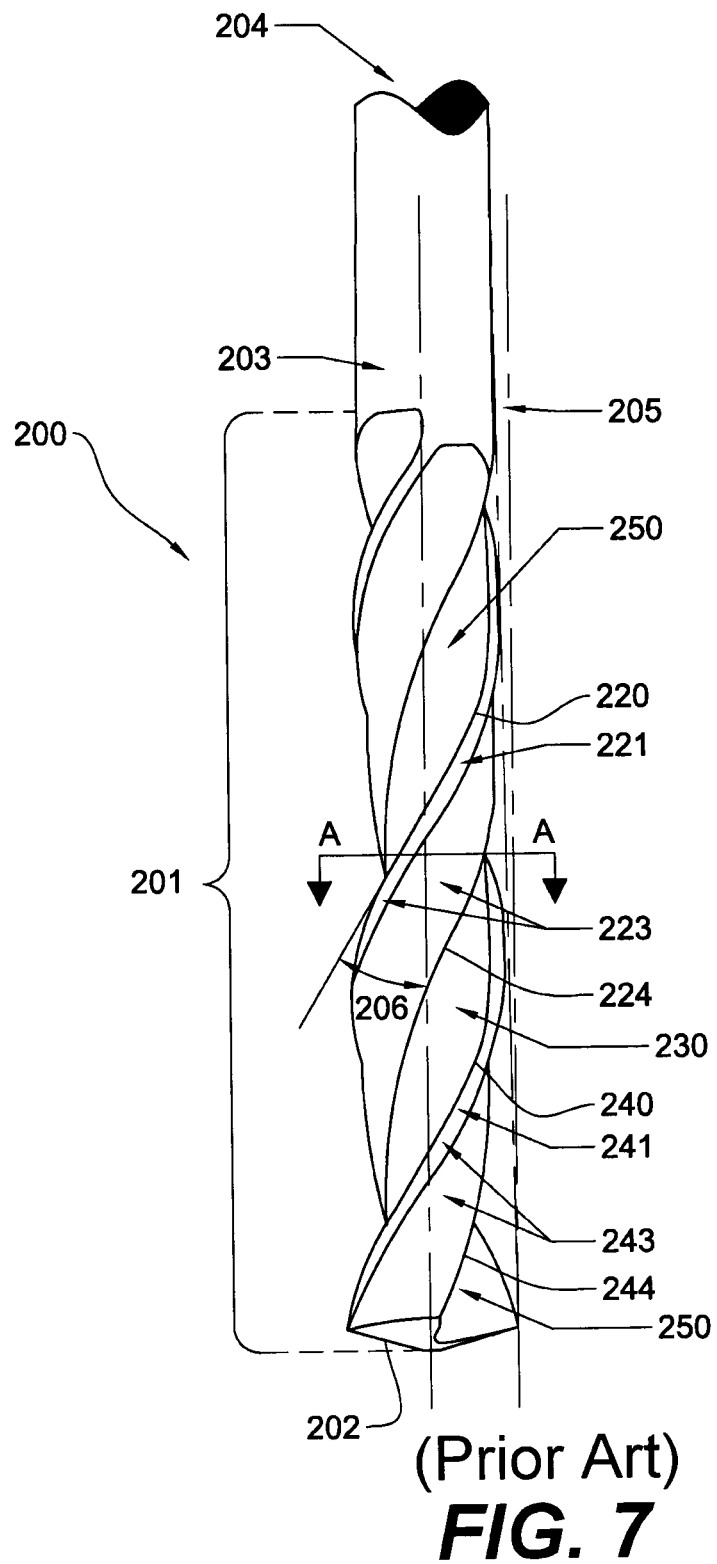
FIGS. 7 and 8 depict a side view and a cross-sectional view respectively of an ordinary twist drill.
Figure 8:
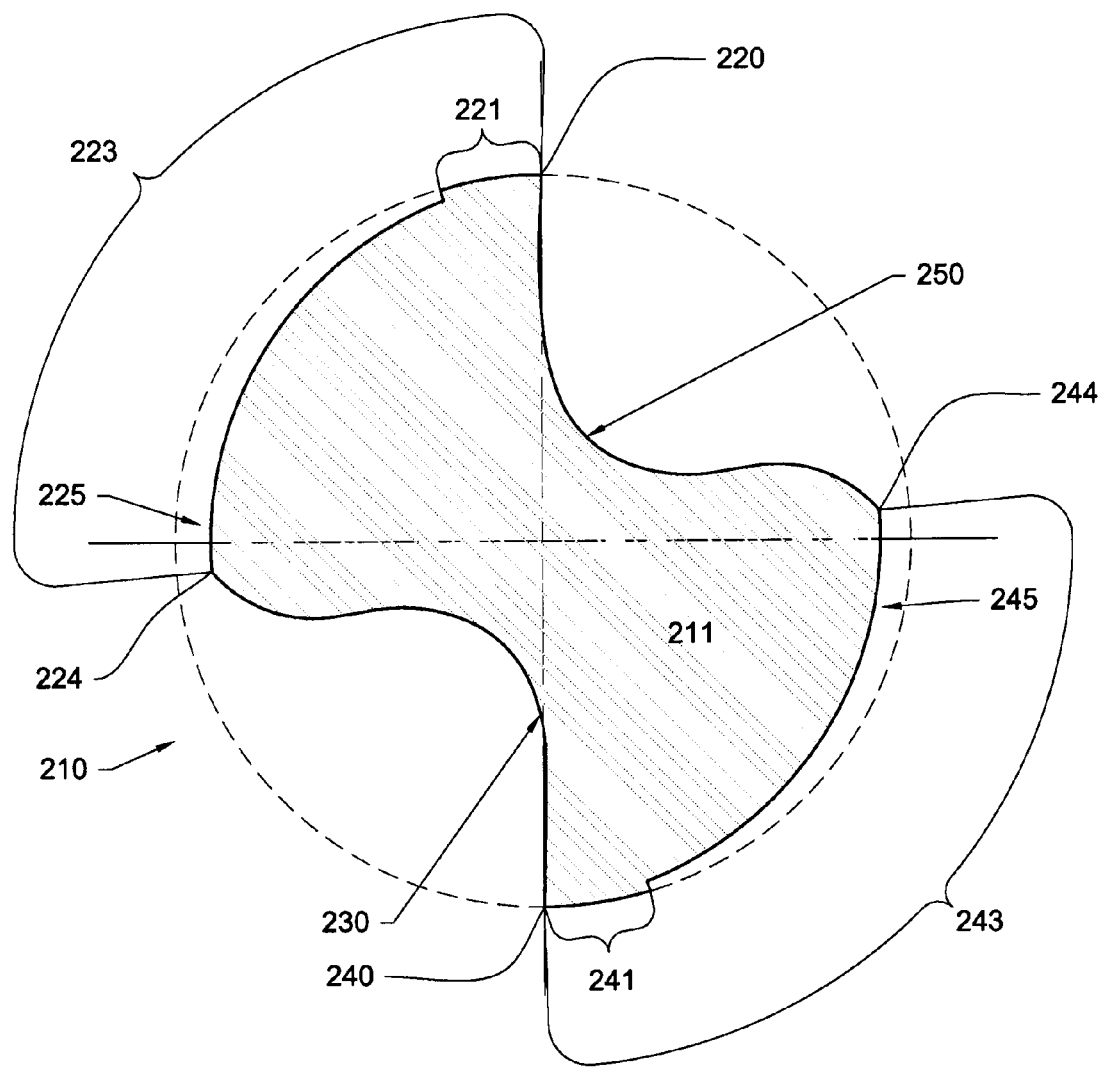
Figure 11:
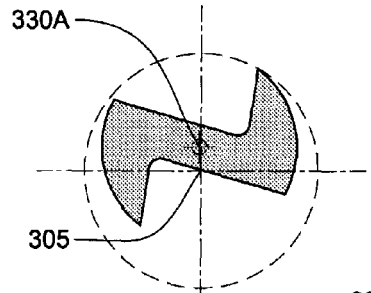
FIGS. 9-13 depict various views of an example two-sided rotary offset drill and/or reamer with a tip end that coincides with the axis of rotation. This drill and/or reamer embodiment cuts a cylindrical cutting envelope.
Figure 12:
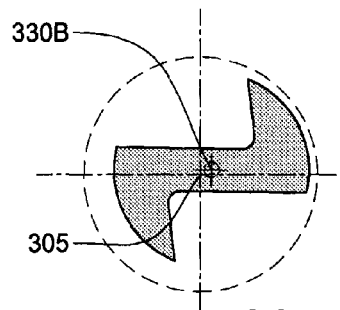
Figure 13:
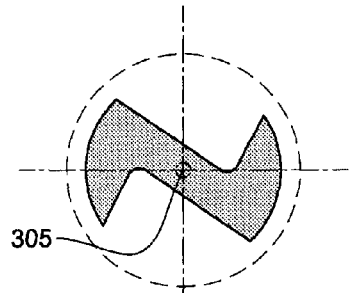
Figures 9, 10:
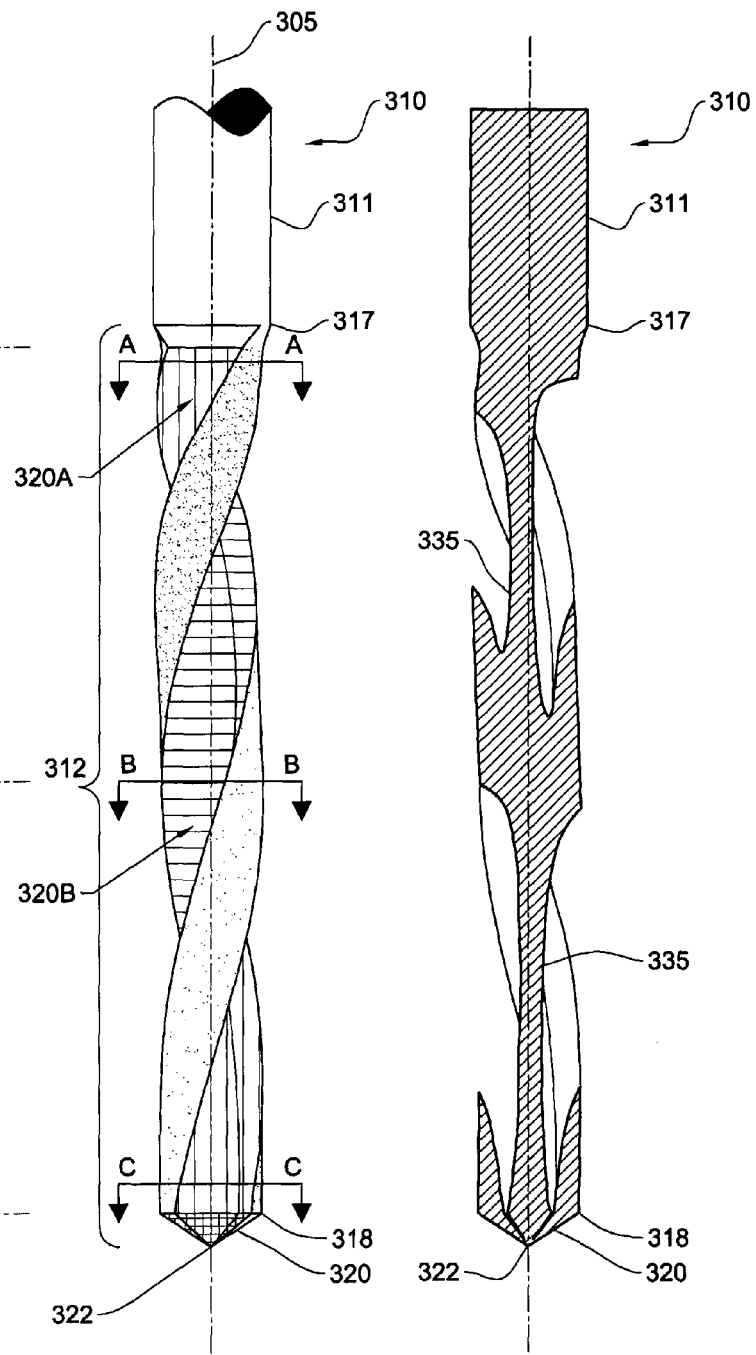

FIGS. 7 and 8 provide an example of a standard twist drill 200 (as previously described).

FIGS. 9-32 illustrate, in a non-limiting sense, various example implementations of the cutting instruments (e.g., drills, reamers, and the like) provided herein. It should be understood that the embodiments provided in the figures of this disclosure are not an exhaustive compilation of the cutting instruments provided herein, but rather serve to illustrate particular concepts and features provided in this disclosure. For example, one feature of at least some of these implementations is that the centers of mass of the transverse cross-sections are further from the axis of rotation at the shank end of the working portion than at the free end or tip end of the working portion. In some embodiments, the offset of the center of mass from the axis of rotation can decrease monotonically, e.g., non-increasing or non-decreasing, from the shank end to the tip end. In some such embodiments, since the cross-sectional shape of the working portion rotates from the shank end to the tip end, the centers of mass of the cross-sections form a spiral path of decreasing diameter (from shank to tip) around the axis of rotation. Although the implementations of FIGS. 9-32 are illustrated with the center of mass at the tip end of the working portion located on the axis of rotation, this is not necessary. That is, the center of mass at the tip end of the working portion can be offset from the axis of rotation (although, in some embodiments, not as much as the shank end).

In some embodiments, the diameter of the working portion can be substantially constant from the shank to the tip end. Alternatively, some embodiments have some degree of "back taper" at angle of less than 10 degrees from the axis of rotation.

After the working portion of the drill, the drill narrows (suddenly in some embodiments) to form an angled tip. For example, in some embodiments the tip can have a point angle of about 60 to 75 degrees, about 75 to 90 degrees, about 90 to 105 degrees, about 105 to 120 degrees, about 120 to 135 degrees, about 135 to 150 degrees, or greater than 150 degrees. In some embodiments, the rake angle at the tip is greater than about 40%.

FIGS. 9-13 illustrates an example two-sided rotary offset drill and/or reamer 310. The drill and/or reamer 310 is described as an "offset" drill and/or reamer because at least some of the centers of mass of the cross-sections (e.g., centers of mass 330A and 330B of FIGS. 11 and 12 respectively) along the working portion 312 are offset from the axis of rotation 305 of the drill and/or reamer 310. As shown in cross-sectional view 3C, in this embodiment the offset begins at the shank 311, and migrates from the shank 311 to the tip 320, until the center of mass becomes centered (coincident) on the axis of rotation 305 at the tip end 320 of the instrument 310.

This drill 310 features a narrow web 335. The drill 310 defines two flutes 320A and 320B that, relative to the center of mass, are substantially bisymmetrical in transverse cross-section, and that can be utilized to remove material. An engine driven motor actuator with a hand-piece and/or chuck, or a handle utilized for manual actuation, can be fixedly attached to the shank 311. The drill and/or reamer instrument 310 is well-suited, for example, for use as a pilot drill, drill and/or reamer for a variety of applications. In the depicted embodiment, the tip end 318 is slightly smaller than the working surface near the shank end 317. Therefore, this drill and/or reamer 310 cuts a tapered cutting envelope because of the offset centers of mass. Those skilled in the art will recognize, however, that varying the diameter of the working surface near the shank and/or the tip end would provide for a cutting envelope that is either tapered or parallel (cylindrical).

FIGS. 14-21 illustrate another example embodiment of the drill and/or reamers provided herein. The drill and/or reamer instrument 410 depicted includes a shank 411, a free end or tip 413, and a working portion 412 therebetween. In some embodiments, the diameter of the working portion 412 is tapered or multi-tapered, that is, decreasing or increasing in diameter between the shank 411 and the tip 413. In other embodiments, the diameter of the working portion 412 is consistent along the working portion 412.

The drill 410 defines two flutes 420A and 420C that are relatively bisymmetrical in transverse cross-section, and that can be utilized to remove material. As will be described further, in this embodiment the drill and/or reamer 410 cuts a cavity or hole that is tapered.

An engine driven motor actuator with a hand-piece and/or chuck, or a handle utilized for manual actuation, can be fixedly attached to the shank 411.

The tip 413 can include an active or cutting surface that is confluent with the working portion 412. Alternatively, the leading tip 413 can include a non-active or non-cutting surface that is confluent with the working portion 412.

In the depicted embodiment, the MxFD (maximum flute diameter) 417 of the drill and/or reamer 410 is located near the shank 411 end of the working portion 412. The MnFD (minimum flute diameter) 418 is located near the tip 413. The shank 411 above the working portion 412 is essentially cylindrical and may have a slightly larger diameter than the cutting surface at the MxFD 417. With reference in particular to FIGS. 17-21, those skilled in the art will recognize that the center of mass of a cross-section at the MxFD 417 is offset from the axis of rotation 440 of the drill and/or reamer 410. However, the center of mass of a cross-section at the MnFD 418 lies on or coincides with the axis of rotation 440.

As shown in FIGS. 14-21, the drill and/or reamer 410 defines two continuous helical flutes 420A and 420C. The flutes 420A and 420C are substantially concave grooves following the circumference of the working portion 412 as three-dimensional spirals between the shank 411 and the leading tip 413. The flutes 420A and 420C occur alternately with lands 420B and 420D. In some embodiments, the flutes 420A and 420C have a uniform pitch along the longitudinal axis. In other embodiments, the flutes 420A and 420C may become increasingly tighter or more numerous as they approach the tip 413, or less tighter or less numerous as they approach the tip 413. The total number of turns per flute of the flutes 420A and 420C between the MxFD 417 and the MnFD 416 can depend on the total length of the working portion 412, but is usually not less than one-quarter of one complete revolution. Helical flutes 420A and 420C each originate at the MxFD 417 at separate locations that are equally spaced apart around the circumference of the shank 411, or more specifically, in this embodiment, at 180 degrees of separation for two flutes with a resultant symmetric cross-section. However, those skilled in the art will recognize that asymmetric cross-sections are possible.

Figure 17:
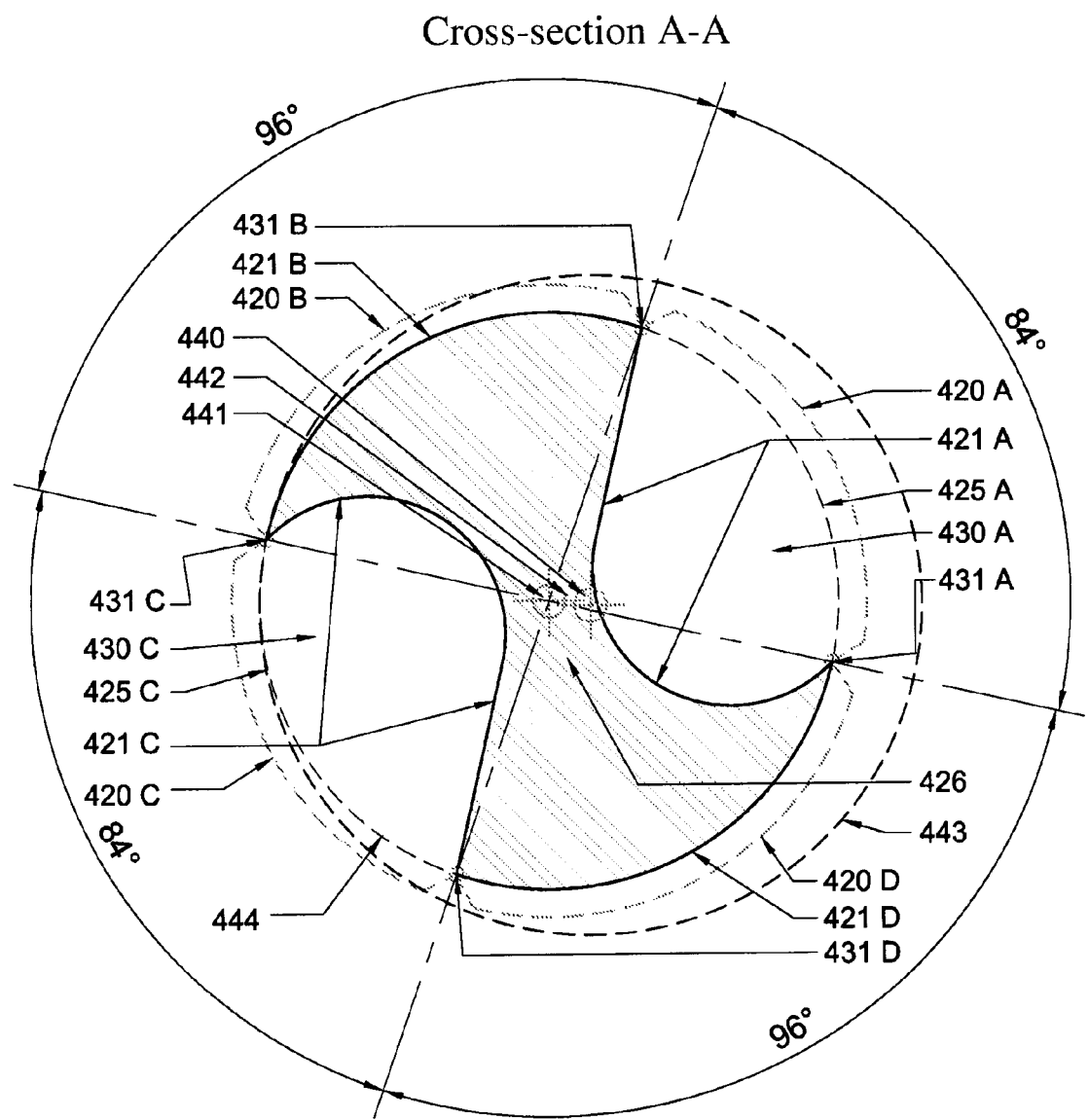
FIGS. 17 and 20 are transverse cross-sectional views of FIG. 14 taken at sections A-A and B-B respectively.
Figure 20:
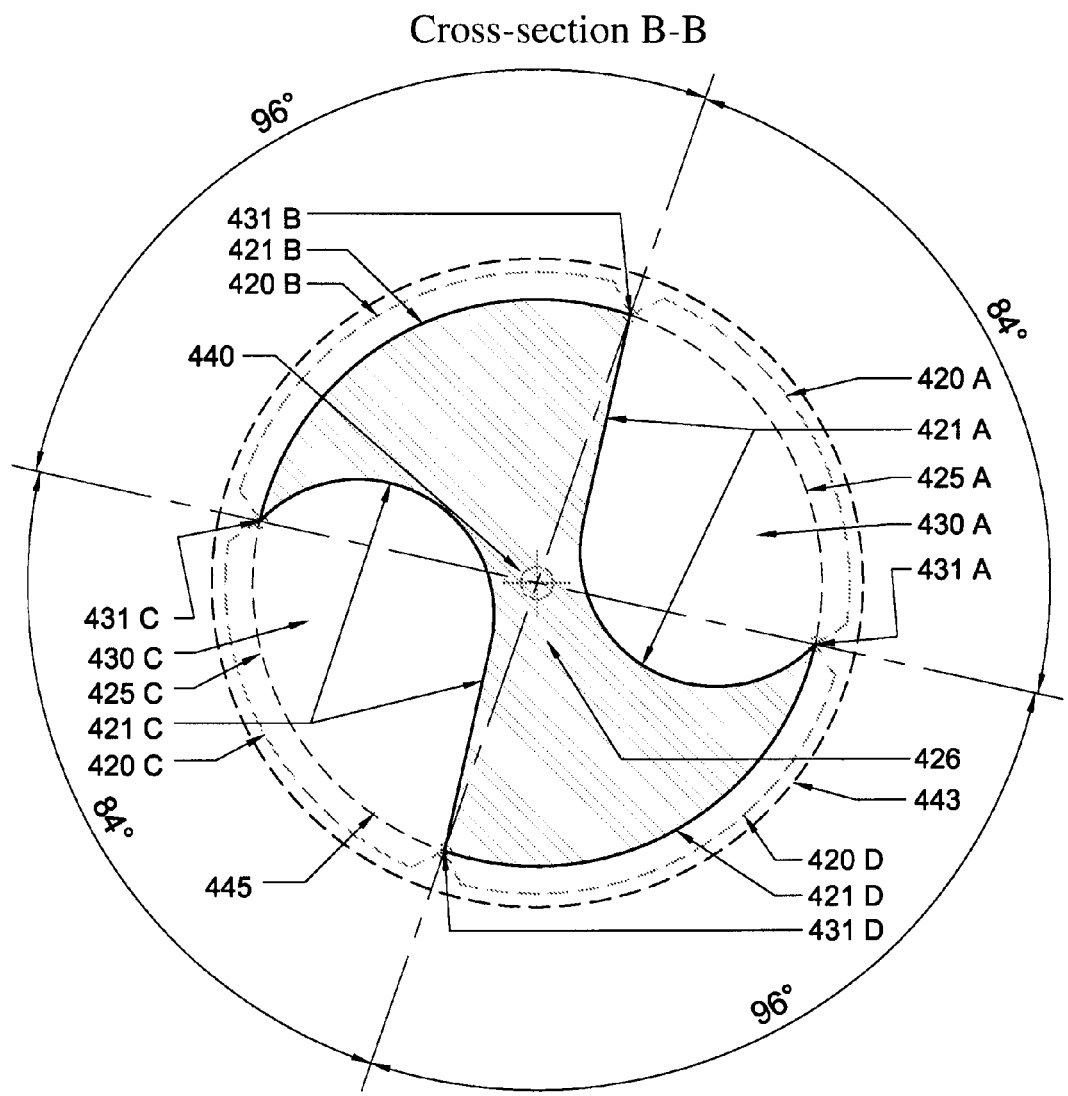
Figure 21:
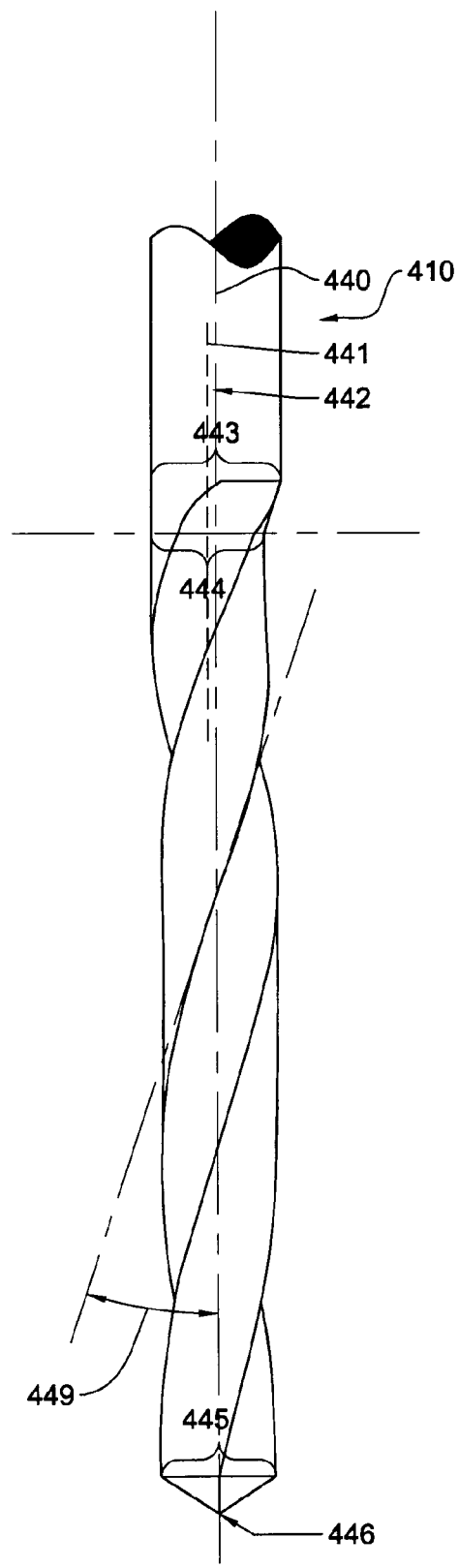
FIG. 21 depicts the two-sided rotary offset drill and/or reamer of FIG. 14, and demarcates the center of rotation and a cross-sectional center of mass, which are offset from each other.

As best seen in FIGS. 17 and 20, the flutes 420A and 420C are defined by J-shaped splines 421A and 421C. The J-shaped splines 421A and 421C intersect with the lands 421B and 421D to form helical cutting edges 431A and 431C extending from the periphery of the shank 411 to the tip 413. The J-shaped splines 421A, 421C and the lands 421B, 421D comprise the surfaces of a web or core 426 of the drill 410. The areas of radial clearance, or cut-outs, of the flutes 421A and 421C outline a portion of the web or core 426. These areas of clearance are designated by numerals 430A and 430C. In transverse cross-section from the shank 411 to the tip 413, the splines 421A and 421C of cutting flutes 420A and 420C form teardrop shaped clearance areas of variable depth. The cutting surfaces 425A and 425C and the splines of the inner walls 421A and 421C circumscribe clearance areas 430A and 430C.

With further reference to FIGS. 17 and 20, it can be seen that the generally J-shaped splines 421A and 421C intersect the periphery of the shank 411 from points 431A to 431B and 431C to 431D. These intersections are equal distances apart, or at about 180° of separation, forming a slightly negative or neutral cutting angle (or approximately a 90° angle to the tangent of the perimeter of shank 411). It is recognized that this cutting angle may be either negative, positive (that is, less than or greater than 90° to the tangent of the perimeter of the shank 411) or neutral. It is envisioned that to create various embodiments of the drill and/or reamers provided herein, splines 421A and 421C may be varied in depth and shape, and may have any of a myriad of different configurations. For example, while the splines 421A and 421C are J-shaped, in some embodiments the splines 421A and 421C are S-shaped splines (e.g., as shown in the embodiment of FIG. 22), or linear, and may be individually symmetrical or asymmetrical, and may or may not be mirror images of each other. While the depth and shape of each spline 421A and 421C can vary, the cross-sectional diameter of the core portion 426 is generally not narrower than about 20% percent of the diameter of the shank 411.

As stated above, the drill and/or reamer 410 is an example two-sided rotary offset drill and/or reamer embodiment. In regard to the offset feature, and further referencing FIGS. 17 and 20, the drill 410 has a center-line or axis of rotation 440 (about which the drill 410 rotates when in use), and a center of mass path (also referred to herein as a "mass axis") 441 which does not completely coincide with the axis of rotation 440. The mass axis 441 is a curved or linear path defined by the centers of mass of consecutive cross-sectional areas of the drill and/or reamer 410. The offset is the difference between the mass axis 441 and the axis of rotation 440 (which are displaced a distance 442 away from each other at the MxFD 417). In this embodiment, the offset distance 442 decreases continuously from the shank 411 to the tip 413, and is zero at the end-point 446. As stated, this unique offset feature allows the instrument 410 to cut using a precessional motion. Accordingly, in this embodiment the drill and/or reamer 410 cuts a cavity or hole that is tapered.

Figure 18:
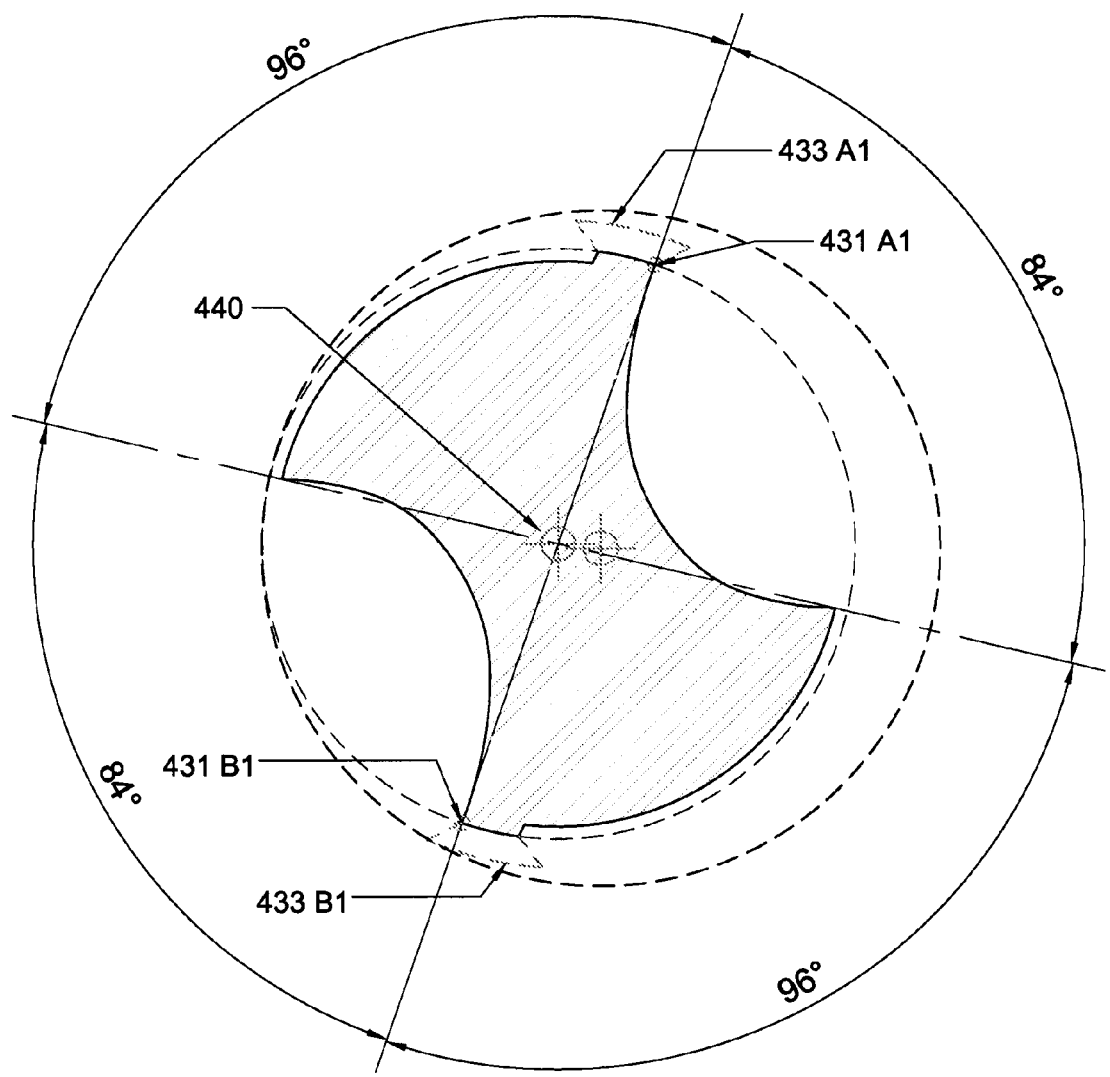
FIGS. 18 and 19 are example alternate transverse cross-sections of FIG. 14 taken at sections A-A and B-B respectively.
Figure 19:
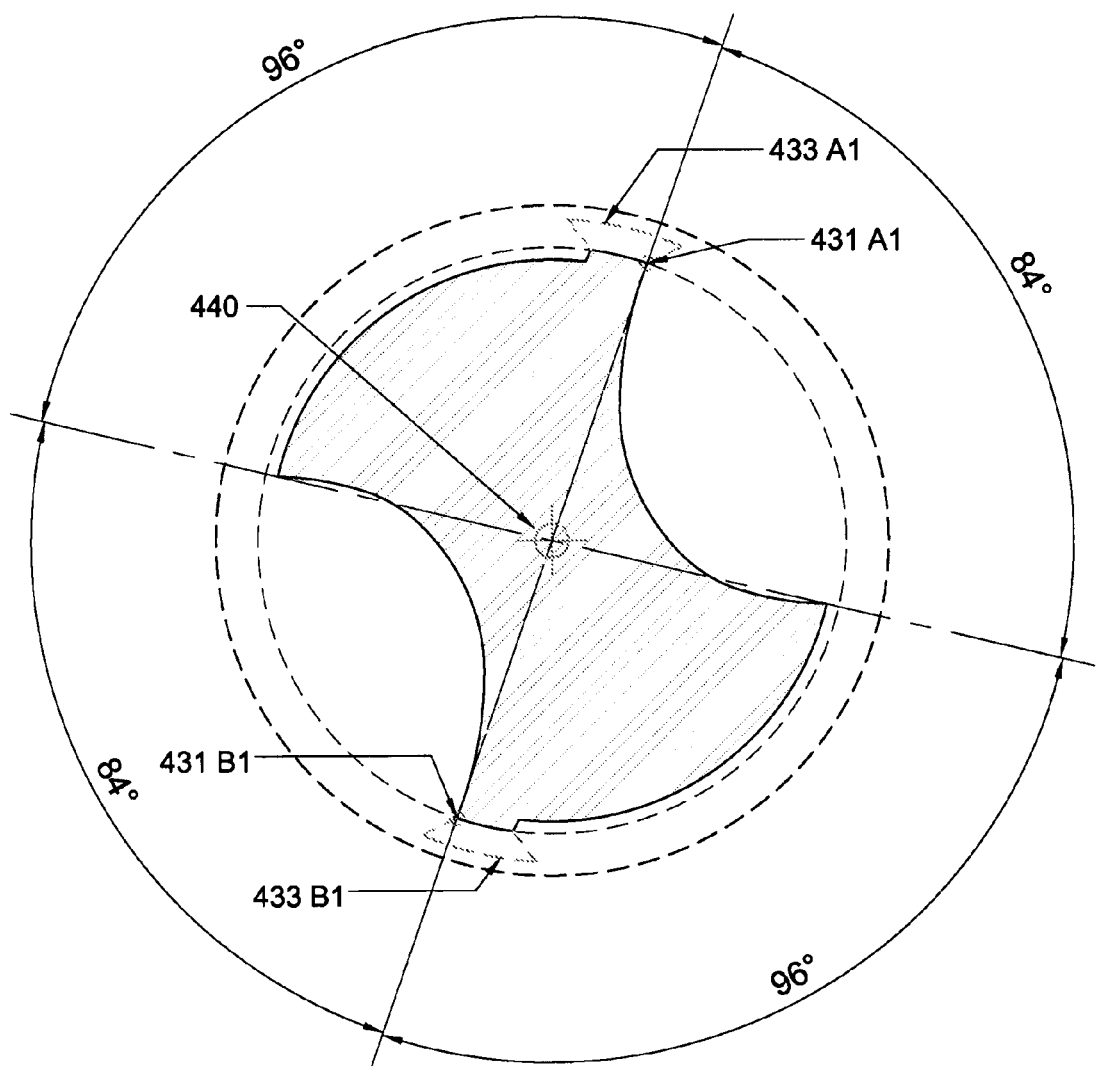

FIGS. 18 and 19 are alternate transverse cross-sections of a drill body specifically designed for strength. FIG. 18 is taken at the shank end of the device and demonstrates and offset center of mass when compared to the axis of rotation. The offset continues toward the tip end progressively decreasing where the axis of rotation and center of mass correspond as shown in FIG. 19. In this example, the flutes 421A1 and 421C1 are essentially arcuate (as opposed to J-shaped in FIGS. 17 and 20), which maximizes the cross-sectional area of the core of web 426. Also note that in this example, margins 433 have been added which can further strengthen and stabilize the device. This design is included as an alternative to the previous cross-sections, and is directed toward use in drilling hard materials with low levels of elasticity such as metals.

FIGS. 22-27 illustrate another example embodiment of an offset drill and/or reamer 510. This offset drill and/or reamer 510 is an example of a three-sided rotary offset drill and/or reamer embodiment. The cutting instrument 510 is generally triangular in transverse cross-section, and can be utilized to remove material in a variety of application during drilling and/or reaming. The offset drill and/or reamer instrument 510 includes a shank 511, a free end or tip 513, and a working portion 512 therebetween. In this embodiment, the diameter of the working portion 512 is slightly tapered, that is, decreasing in diameter from the shank 511 to the tip 513. Alternatively, the diameter of the working portion 512 can remain substantially constant along the length of the working portion 512, or can increase in diameter from the shank 511 to the tip 513. The working portion 512 of the drill 510 defines three flutes 520A, 520B, and 520C. As will be described further, in some embodiments the offset drill and/or reamer 510 cuts material or prepares a hole that is tapered.

An engine driven motor actuator with a hand-piece and/or chuck, or a handle utilized for manual actuation, can be fixedly attached to the shank 511.

The tip 513 can include an active or cutting surface that is confluent the working portion 512. Alternatively, the leading tip 513 can include a non-active or non-cutting surface that is confluent with the working portion 512.

Figure 26:
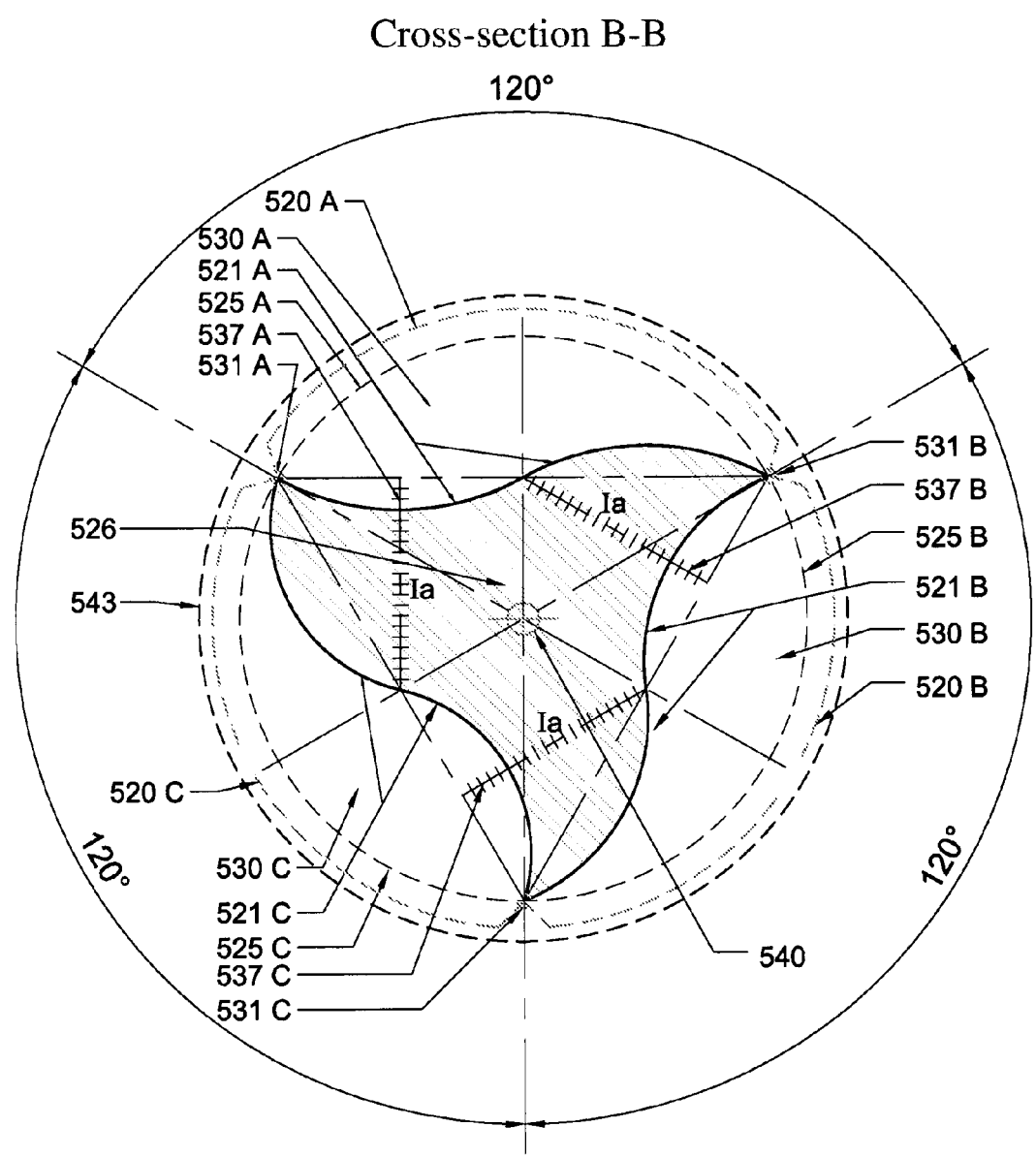
Figure 27:
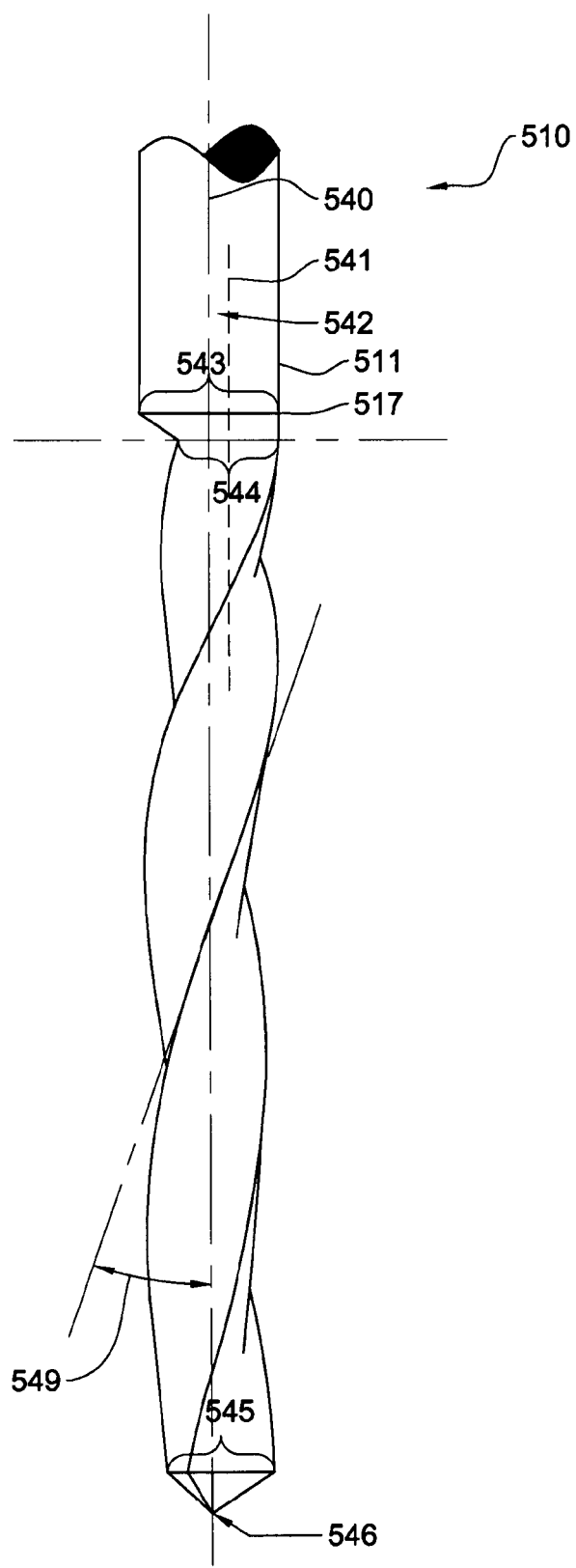
FIG. 27 depicts the three-sided rotary offset drill and/or reamer of FIG. 22, and demarcates the center of rotation and a cross-sectional center of mass, which are offset from each other.

The MxFD 517 is located near the shank 511 end of the working portion 512. The MnFD 518 is located near the tip 513. The shank 511 above the working portion 512 is essentially cylindrical and may have a slightly larger diameter than the cutting surface at the MxFD 517. With reference in particular to FIGS. 26 and 27, those skilled in the art will recognize that the center of mass of a cross-section at the MxFD 517 is offset from the axis of rotation 540 of the offset drill and/or reamer 510 by a distance 542. However, in the depicted embodiment the center of mass of a cross-section at the MnFD 518 coincides with the axis of rotation 540.

As shown in FIGS. 22-27, the offset drill and/or reamer 510 defines three continuous helical flutes 520A, 520B, and 520C. The flutes 520A, 520B, and 520C are substantially concave grooves which follow the circumference of the working portion 512 as spirals between the shank 511 and the leading tip 513 to define concentric circles. In some embodiments, the flutes 520A, 520B, and 520C may be equidistant from each other. In particular embodiments, the flutes 520A, 520B, and 520C may become increasingly tighter or more numerous as they approach the tip 513, or less tighter and less numerous as they approach the tip 513. The total number of turns per flute of the flutes 520A, 520B, and 520C from MxFD 517 to the MnFD 516 can depend on the total length of the working portion 512, but is not less than one-quarter of one complete revolution. In the depicted embodiment, helical flutes 520A, 520B, and 520C each originate at the MxFD 517 at separate locations that are equally spaced apart around the circumference of the shank 511, or more specifically at 120 degrees of separation. However, in some embodiments, the helical flutes 520A, 520B, and 520C may spaced apart from each other at unequal amounts (e.g., 110 degrees, 120 degrees, and 130 degrees, to provide one example).

Figure 25:
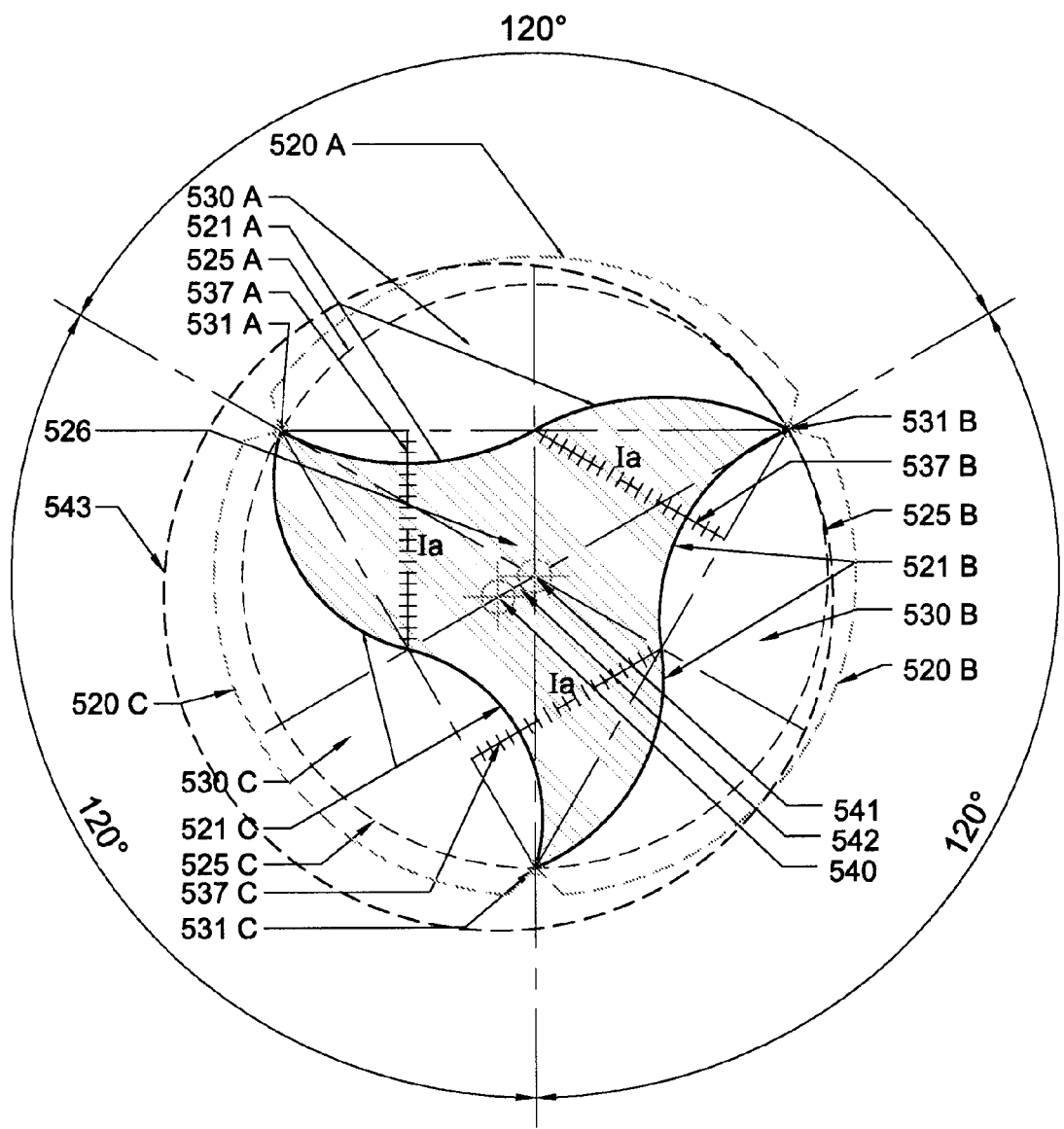
FIGS. 25 and 26 are transverse cross-sectional views of the three-sided rotary offset drill and/or reamer of FIGS. 22-24 taken at sections A-A and B-B respectively.

As best seen in FIGS. 25 and 26, the flutes 520A, 520B, and 520C are defined by surfaces of S-shaped splines 521A, 521B, and 521C. The flutes 520A, 520B, and 520C intersect to form helical cutting edges 531A, 531B, and 531C between the periphery of the shank 511 and tip 513. The helical flutes 520A, 520B, and 520C cooperate to form a web or core 526, which is essentially triangular. The areas of radial clearance or cut-outs 530A, 530B, and 530C of the flutes 521A, 521B, and 521C outline the web or core 526. In transverse cross-section from the shank 511 to the tip 513, the splines 521A, 521B, and 521C of cutting flutes 520A, 520B, and 520C form arcuate shaped clearance areas of variable depth. The cutting edges 525A, 525B, and 525C and the splines of the inner walls 521A, 521B, and 521C circumscribe clearance areas 530A, 530B, and 530C.

With further reference to FIGS. 25 and 26, it can be seen that the S-shaped splines 521A, 521B, and 521C intersect the periphery of the shank 511 at points 531A, 531B, and 531C. In some embodiments, these intersections are equal distances apart, and at 120° of separation to form a neutral cutting angle (90° angle to the tangent of the perimeter of shank 511) or slightly positive rake angle (greater than 90° to the tangent of the perimeter of the shank 511). It should be recognized that this cutting angle maybe either negative or positive (that is, less than or greater than about 90° to the tangent of the perimeter of the shank 511). In this embodiment, lines drawn to connect points 531A, 531B, and 531C form an equilateral triangle. However, those skilled in the art will also recognize that points 531A, 531B, and 531C may be separated by varying degrees and/or distances rendering the cross-section albeit triangular, asymmetrical (for example, at 110, 125, and 125 degrees of separation, or at other degrees of separation). It will also be recognized that splines 521A, 531B, and 521C may be variable in depth and shape and may have any of a myriad of different configurations.

In this example offset drill and/or reamer 510, the splines 521A, 521B, and 521C are S-shaped and are individually symmetrical. However, in some embodiments the splines 521A, 521B, and 521C may have other shapes including linear, J-shaped, and so on. The bisector of each spline divides the spline equally into convex and a concave segments which form the S-shaped profile. The lines that bisect each spline 521A, 521B, and 521C can be drawn to the centroid of the core 526 and are equal in length. Further, an alternate bisector can be drawn from the bisect center point of each spline 521A, 521B, and 521C through the greatest concavity the adjacent spline 521A, 521B, and 521C. Lines drawn perpendicular to the alternate bisector lines form an equilateral triangle. The bisectors for each spline 521A, 521B, and 521C are equal. The greatest depth of each spline can be defined by a segment of Ia (refer to FIGS. 25 and 26). These depths can vary and, furthermore, can be calculated as a percentage of the length of Ia. The greatest depths of splines 521A, 521B, and 521C, indicated with demarcated line segments 537A, 537B, and 537C, are about 15%, 20%, or 25% of the length of Ia, respectively. The greatest convexities of splines 521A, 521B, and 521C are mirror images of the greatest concavities of the same splines. While the depth and height of each spline 521A, 521B, and 521C can vary, the cross-sectional diameter of the core portion 526 is generally not narrower than about 20% percent of the diameter of the shank 511.

As stated above, the offset drill and/or reamer 510 is an example of a three-sided rotary offset drill and/or reamer embodiment. In regard to the offset feature, and further referencing FIGS. 25-27, the drill 510 has a center-line or axis of rotation 540 (about which the drill 510 rotates when in use), and a mass axis 541 that does not completely coincide with the axis of rotation 540. The mass axis (or center of mass path) 541 is a continuum of points defined by the centers of mass of consecutive cross-sectional areas of the offset drill and/or reamer 510. The offset is the difference between the mass axis 541 and the axis of rotation 540 (which are displaced a distance 542 away from each other). The offset distance 542 decreases continuously from the shank 511 to the tip 513, and is zero at the end-point 546 in the depicted embodiment. This unique offset feature allows the instrument 510 to cut with a precessional motion. In addition, in some implementations at any position along the working body 512 at least one of cutting edges 531A, 531B, or 531C is out of contact with the material being cut by the cutting instrument 510. In the depicted embodiment, the offset drill and/or reamer 510 can cut a cavity or hole in a variety of materials that is tapered. However, those skilled in the art will recognize that adjustments of the MxFD 517 and MnFD 518 can render a hole that is variably tapered or parallel.

FIGS. 28-33 illustrate another example offset drill and/or reamer 610. The offset drill and/or reamer 610 is another example of a three-sided rotary offset drill and/or reamer embodiment. The offset drill and/or reamer 610 has three sides, is generally triangular in transverse cross-section, and can be utilized to remove material in a variety of applications during drilling and/or reaming. The offset drill and/or reamer instrument 610 includes a shank 611, a free end or tip 613, and a working portion 612 therebetween. In the depicted embodiment, the diameter of the working portion 612 is slightly tapered, that is, increasing in diameter from the shank 611 to the tip 613. Alternatively, the diameter of the working portion 612 can remain substantially constant along the length of the working portion 612, or can decrease in diameter from the shank 611 to the tip 613. The working portion 612 of the drill 610 defines three flutes 620A, 620B, and 620C. As will be described further, in this embodiment the offset drill and/or reamer 610 cuts a cavity or hole that is generally cylindrical.

An engine driven motor actuator with a hand-piece and/or chuck, or a handle utilized for manual actuation, can be fixedly attached to the shank 611.

The tip 613 can include an active or cutting surface that is confluent the working portion 612. Alternatively, the leading tip 613 can include an active or cutting tip or non-active or non-cutting surface that is confluent with the working portion 612.

Figure 32:
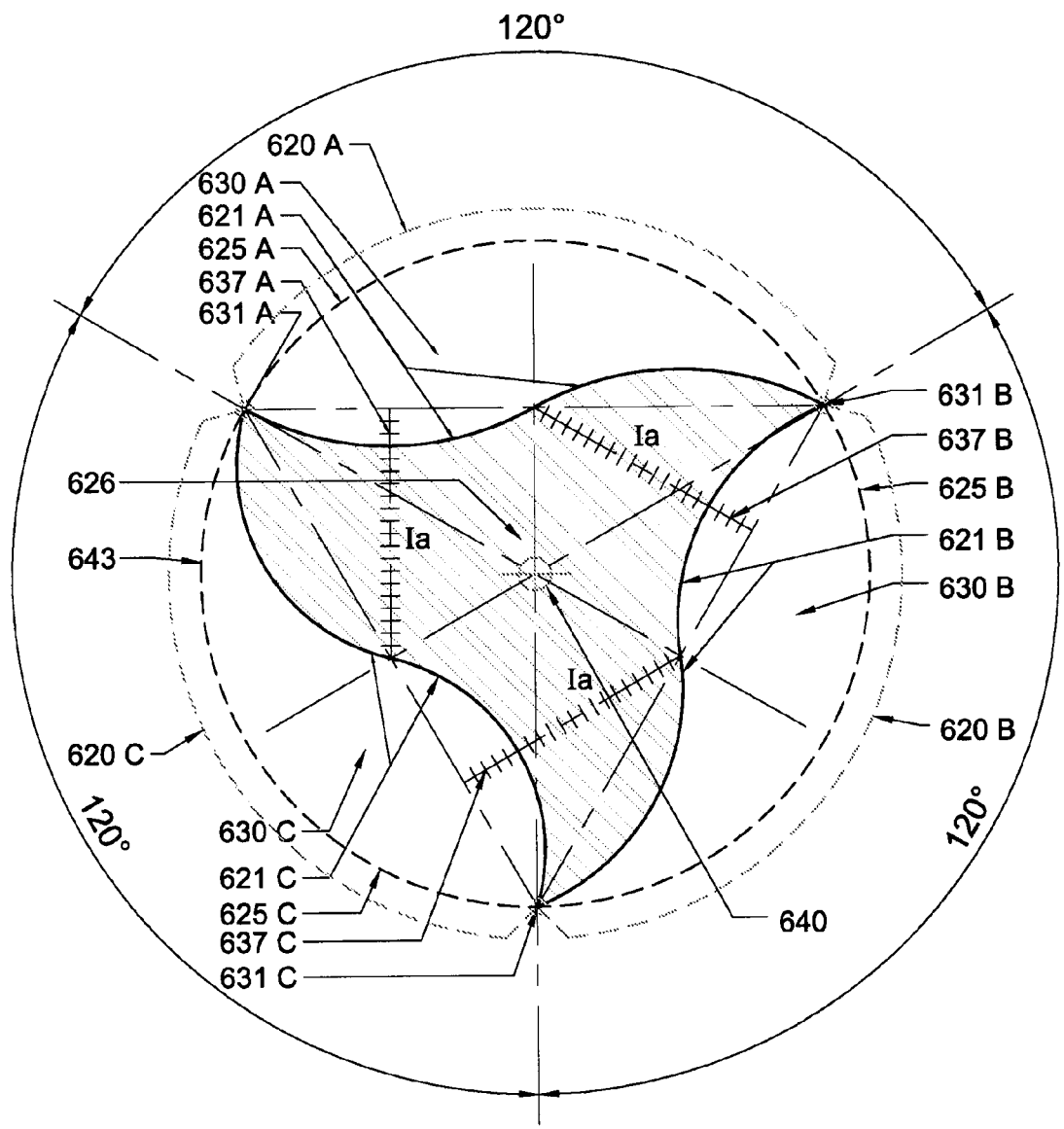
Figure 33:
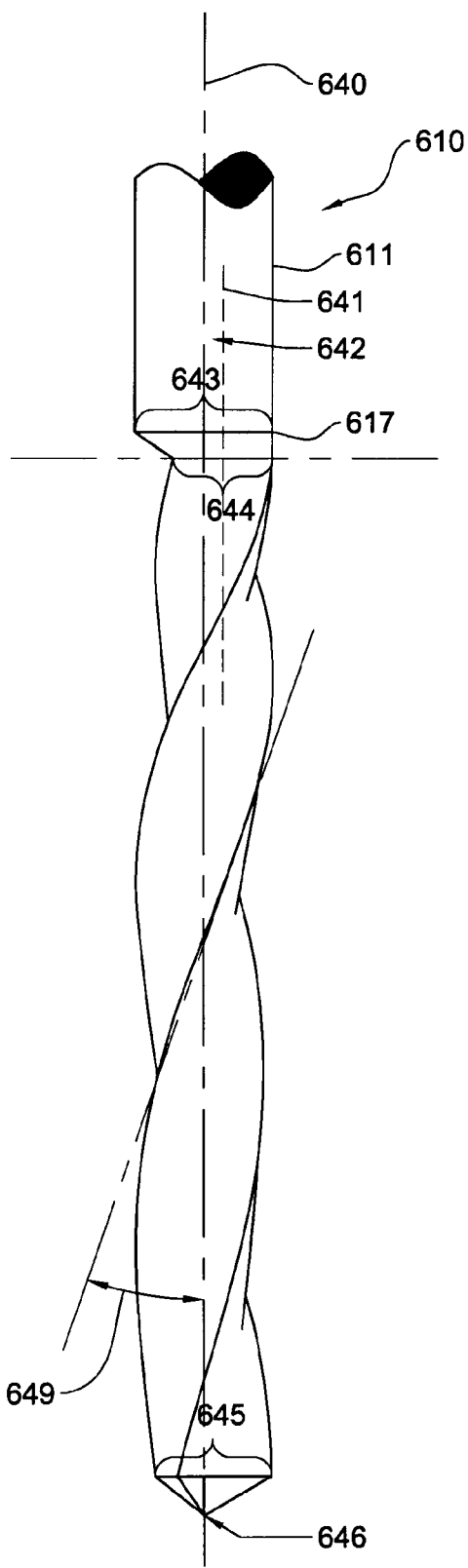
FIG. 33 depicts the three-sided rotary offset drill and/or reamer of FIG. 28, and demarcates the center of rotation and a cross-sectional center of mass, which are offset from each other.

In the depicted embodiment, the MnFD 617 is located near the shank 611 end of the working portion 612. The MxFD 618 is located near the tip 613. The shank 611 above the working portion 612 is essentially cylindrical and exhibits a slightly larger diameter than the cutting surface at the MnFD 617. With reference in particular to FIGS. 32 and 33, those skilled in the art will recognize that the center of mass of a cross-section at the MnFD 617 is offset from the axis of rotation 640 of the offset drill and/or reamer 610 by distance 642. However, the center of mass of a cross-section at the MxFD 618 coincides with the axis of rotation 640.

As shown in FIGS. 28-33, the offset drill and/or reamer 610 defines three continuous helical flutes 620A, 620B, and 620C. The flutes 620A, 620B, and 620C are substantially concave grooves that follow the circumference of the working portion 612 as spirals between the shank 611 and the leading tip 613 to define concentric circles. In some embodiments, the flutes 620A, 620B, and 620C may be equidistant from each other. In some embodiments, the flutes 620A, 620B, and 620C may become increasingly tighter or more numerous as they approach the tip 613. The total number of turns per flute of the flutes 620A, 620B, and 620C from MnFD 617 to the MxFD 616 can depend on the total length of the working portion 612, but is not less than one-quarter of one complete revolution. In the depicted embodiment, helical flutes 620A, 620B, and 620C each originate at the MnFD 617 at separate locations that are equally spaced apart around the circumference of the shank 611, or more specifically at 120 degrees of separation. Each helical structure of the offset drill and/or reamer 610, i.e., the mass between the flutes 620A, 620B, and 620C and defining the flutes 620A, 620B, and 620C, is continuous along the length of the cutting surface 612 from the shank 611 to the leading tip 613.

Figure 31:
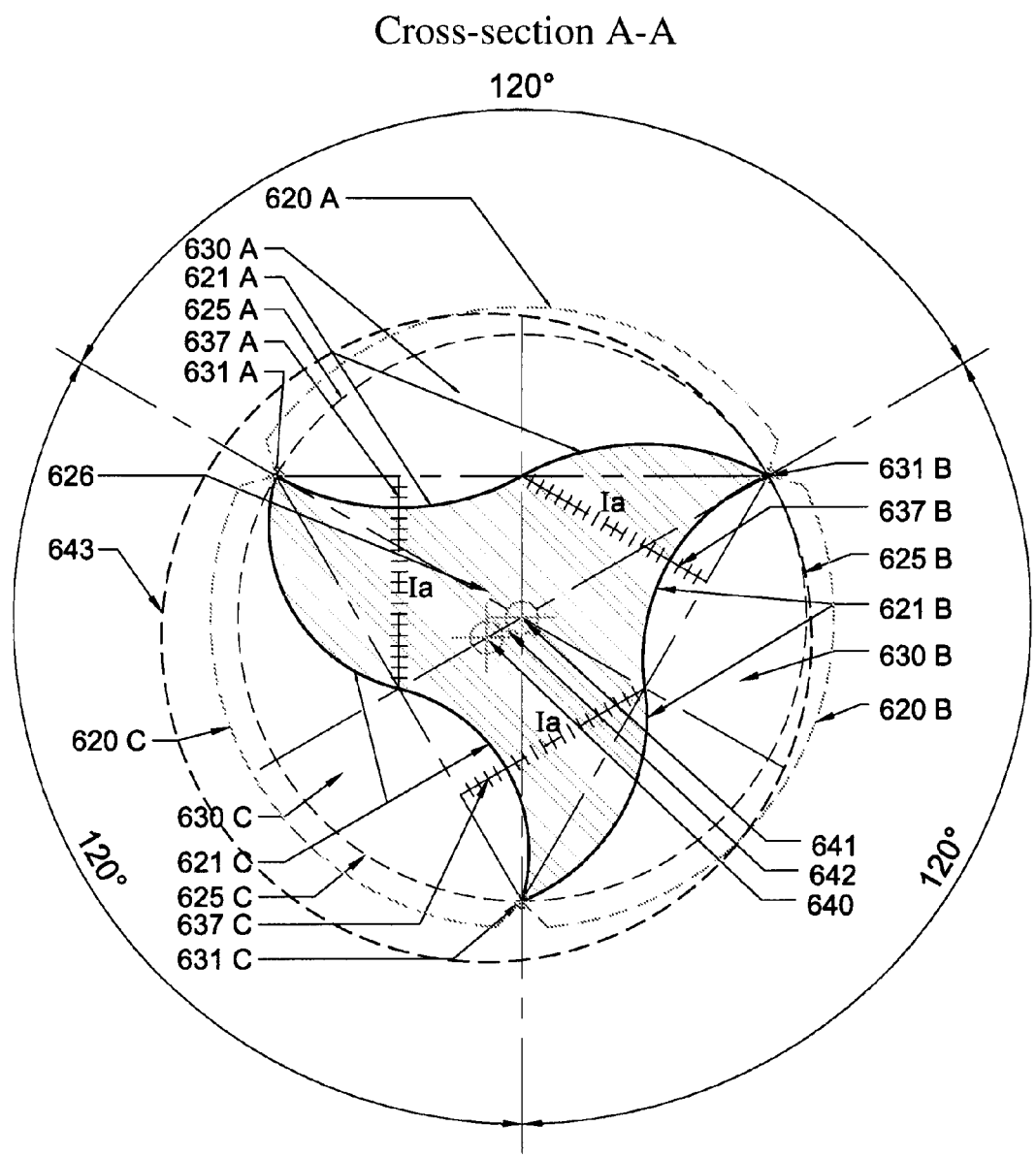
FIGS. 31 and 32 are transverse cross-sectional views of the three-sided rotary offset drill and/or reamer of FIGS. 28-30 taken at sections A-A and B-B respectively.

With further reference to FIGS. 31 and 32, it can be seen that the S-shaped splines 621A, 621B, and 621C intersect the periphery of the shank 611 at cutting edges defined by points 631A, 631B, and 631C. In some embodiments, these intersections are equal distances apart, and at 120° of separation to form a neutral cutting angle (90° angle to the tangent of the perimeter of shank 611) or slightly positive rake angle (greater than 90° to the tangent of the perimeter of the shank 611). It should be recognized that this cutting angle maybe either negative or positive (that is, less than or greater than 90° to the tangent of the perimeter of the shank 611). In this embodiment, lines drawn to connect points 631A, 631B, and 631C form an equilateral triangle. However, those skilled in the art will also recognize that points 631A, 631B, and 631C may be separated by varying degrees and/or distances rendering the cross-section albeit triangular, asymmetrical (for example, at 110, 125, and 125° of separation, or at other degrees of separation). It will also be recognized that splines 621A, 631B, and 621C may be variable in depth and shape and may have any of a myriad of different configurations, including but not limited to linear, J-shaped, and so on.

In this example offset drill and/or reamer 610, the splines 621A, 621B, and 621C are S-shaped and are individually symmetrical. The bisector of each spline divides the spline equally into convex and a concave segments which form the S-shaped profile. The lines that bisect each spline 621A, 621B, and 621C can be drawn to the centroid of the core 626 and are equal in length. Further, an alternate bisector can be drawn from the bisect center point of each spline 621A, 621B, and 621C through the greatest concavity the adjacent spline 621A, 621B, and 621C. Lines drawn perpendicular to the alternate bisector lines form an equilateral triangle. The bisectors for each spline 621A, 621B, and 621C are equal. The greatest depth of each spline can be defined by a segment of Ia (refer to FIGS. 31 and 32). These depths can vary and, furthermore, can be calculated as a percentage of the length of Ia. The greatest depths of splines 621A, 621B, and 621C, indicated with demarcated line segments 637A, 537B, and 537C, are about 15%, 20%, and 25% of the length of Ia, respectively. The greatest convexities of splines 621A, 621B, and 621C are mirror images of the greatest concavities of the same splines. While the depth and height of each spline 621A, 621B, and 621C can vary, the cross-sectional diameter of the core portion 626 is generally not narrower than about 20% percent of the diameter of the shank 611.

As stated above, the offset drill and/or reamer 610 is an example of a three-sided rotary offset drill and/or reamer embodiment. In regard to the offset feature, and further referencing FIGS. 31-33, the drill 610 has a center-line or axis of rotation 640 (about which the drill 610 rotates when in use), and a mass axis 641 that does not completely coincide with the axis of rotation 640. The mass axis 641 is a path defined by the centers of mass of consecutive cross-sectional areas of the offset drill and/or reamer 610. The offset is the difference between the mass axis 641 and the axis of rotation 640 (which are displaced a distance 642 away from each other at MnFD 617). In the depicted embodiment, the offset distance 642 decreases continuously from the shank 611 to the tip 613, and is zero at the end-point 646. However, in other embodiments the offset distance 642 can have any other relationship with the axis of rotation 640 (e.g., equidistant, variable taper, etc.). This unique offset feature allows the instrument 610 to cut with a precessional motion. In result, in some implementations at any position along the working body 512 at least one of cutting edges 531A, 531B, or 531C is out of contact with the material being cut by the cutting instrument 510. In this embodiment, the offset drill and/or reamer 610 can cut a cavity or hole in a variety of materials that is cylindrical. However, those skilled in the art will recognize that adjustments of the MxFD 617 and MnFD 618 can render a hole that is tapered, variably tapered, or parallel, and the like.

The features of the various offset drill and/or reamer embodiments described herein can be combined together in any suitable combination. For example, an offset drill and/or reamer having the cross-sectional shape of offset drill and/or reamer 410 can be used with tapered diameters of offset drill and/or reamers 310, 510, or 610, and the like. In another example, a first portion of an offset drill and/or reamer can have the cross-sectional shape of the offset drill and/or reamer 410, and a second portion of the same offset drill and/or reamer can have the cross-sectional shape of the offset drill and/or reamers 510 or 610. In another example, an offset drill and/or reamer with three flutes such as drills 510 and 610 can have a consistent diameter along the entire working lengths 512 and 612 respectively. In still another example, an offset drill and/or reamer of the shape of 510 of FIG. 22 could be used with decreasing diameter of offset drill and/or reamer 610 of FIG. 28. Similarly, any and all other such combinations and sub-combinations are envisioned within the scope of this disclosure.

Figure 34:
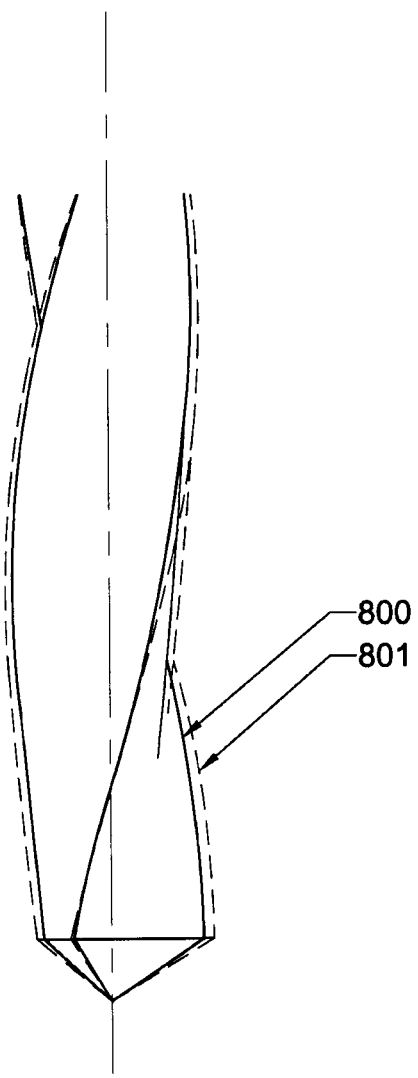
FIG. 34 shows the differential of the cutting envelope of the cutting instrument of FIGS. 22-27 (a tapered cutting envelope) in comparison to the cutting envelope of the cutting instruments of FIGS. 28-33 (a parallel cutting envelope).

FIG. 34 illustrates the differential between the sizes and shapes of the cutting envelopes of the drill 510 of FIGS. 22-27 and the drill 610 of FIGS. 28-33. Drill 510 exhibits a tapered cutting envelope, while drill 610 exhibits a parallel or cylindrical cutting envelope. The tapered cutting envelop of drill 510 is depicted by profile 800 (with solid lines), and the parallel cutting envelope of drill 610 is depicted by profile 801 (with dashed lines).

Figure 35:
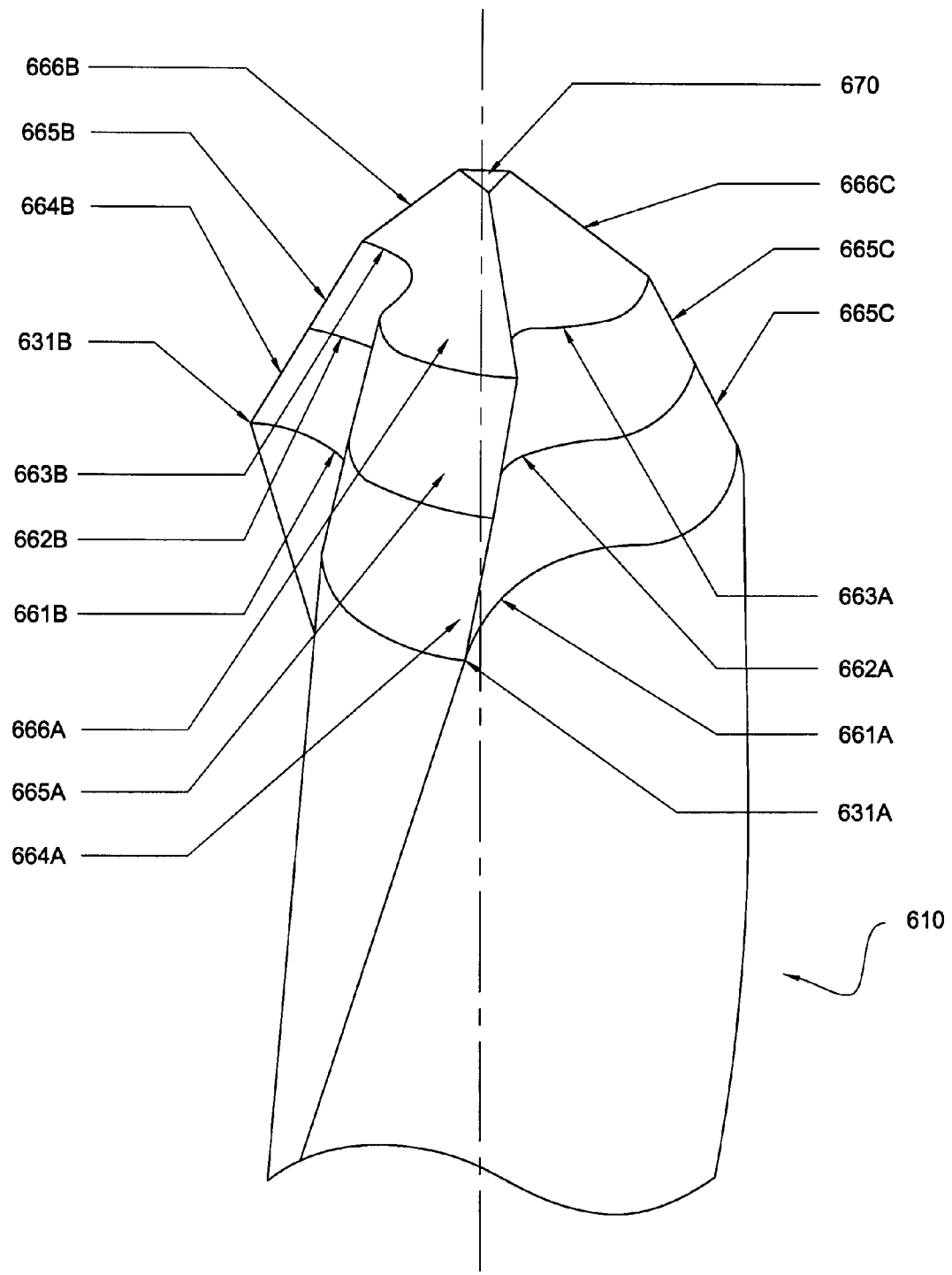
FIG. 35 is a side view and FIG. 36 is an end view of the tip of the cutting device of FIGS. 28-33.
Figure 36:
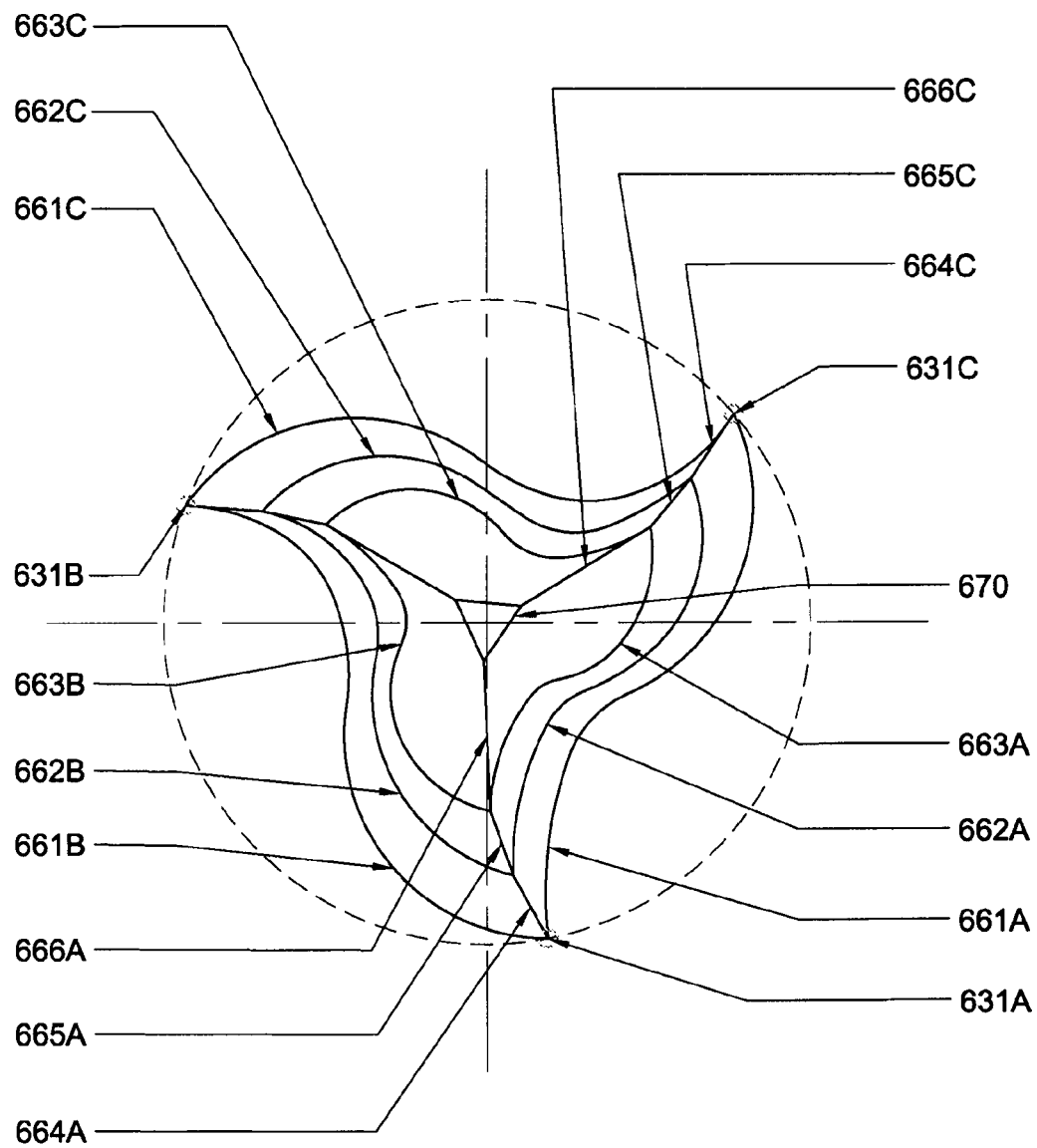

FIG. 35 is a side view and FIG. 36 is an end view of the tip of the device in FIGS. 28-33. The tip 610 of this embodiment is essentially pyramidal with three sides and unlike most chisel tips, which are two sided. Emanating from the sharp tip 670 are three incline planes or facets 666A, 666B and 666C which cooperate to form the first set of cutting lips limited in length by edges 663A, 663B and 663C. In this embodiment, and when viewed from the side, the first incline plane or facet extends laterally away from the central axis and approximates 60 degrees. Thus, in a side view, any two incline planes cooperate to form an angle that approximates 120 degrees. This angle may be increased when used to drill softer materials and decrease when drilling harder materials. This first set of facets is subtended by a second set of facets 665A, 665B and 665C, which are shorter in length than the first set of facets, and cooperate to form a second set of lips limited in length by edges 662A, 662B and 662C. This second set of facets and lips extend away from the central axis at an angle that is less than the angle of the first set of facets. The second set of facets is subtended by a third set of facets 664A, 664B and 664C which are limited in length by edges 661A, 661B and 661C. The third set of facets and lips extend away from the central axis at an angle that is even less than the angle of the first set and second set of facets.

Multi-faceted tip configurations can improve self-centering ability, hole geometry or symmetry, reduce exit burr production, improve chip breakage and hauling capacity, and reduce the axial force or thrust required to operate the drill. Dependent on the needs of the operator and the quality and hardness of the work piece, the numbers of facets and the angle of the incline planes of each facet can be increased or decreased. Designs such as these will work synergistically with precessional cutting tools with offset transverse cross-sections to further improving cutting efficiency.

Referring now to FIGS. 43 and 44 that show examples of active tips 710 and 720 of a pilot drill. Those skilled in the art will recognize that, similar to a drill that has an offset profile, the tip may also be offset from the drill's axis of rotation. FIG. 44 shows a chisel tip 713 that displays incline planes 700B and 703B that are relatively equal. FIG. 43, however, shows a chisel tip 713 where the incline 700A is lower than the incline plane of 703A. The diagrams also illustrate that the surface areas formed by facets 701A and 702A are smaller in combination than the surface area formed by facet 703A. It should also be recognized that in some embodiments a cutting instrument that is offset from shank to tip will also display an offset in the distal extent of the drill and or tip. In some embodiments, the tips can remain substantially centered when in use.

In some of the embodiments described in reference to FIGS. 9-32, the point at the free end or tip, (e.g., the point 322 at the end of the tip 320) is approximately coincident with the axis of rotation. However, that coincidence of the point at the tip and the axis of rotation is not required. For example, in some embodiments the pointed end of the tip can be offset from the axis of rotation.

FIGS. 37-42 show an example cutting instrument 710 having such an offset tip (i.e., the pointed end of the tip is offset from the axis of rotation) in accordance with some embodiments. This can be the case in embodiments where the center of mass of the shank end of the working portion coincides with the axis or rotation, and/or where the center of mass of the shank end of the working portion is offset from the axis of rotation.

In the depicted embodiment, the offset drill and/or reamer 710 is a three-sided rotary offset drill and/or reamer embodiment that is generally triangular in transverse cross-section. However, in some embodiments the cutting instrument 710 can be two-sided, four-sided, five-sided, and so on. The offset drill and/or reamer 710 has three sides, is generally triangular in transverse cross-section, and can be utilized to remove material in a variety of applications during drilling and/or reaming. The offset drill and/or reamer instrument 710 includes a shank 711, a tip 713 (also referred to herein as a free end), and a working portion 712 therebetween. In some embodiments, the diameter of the working portion 712 is slightly tapered, that is, increasing in diameter from the shank 711 to the tip 713. Alternatively, the diameter of the working portion 712 can remain substantially constant along the length of the working portion 712, or can be tapered such that the diameter decreases from the shank 711 to the tip 713. The working portion 712 of the drill 710 defines three flutes 720A, 720B, and 720C. As will be described further, in this embodiment the offset drill and/or reamer 710 cuts a cavity or hole that is generally cylindrical.

An engine driven motor actuator with a hand-piece and/or chuck, or a handle utilized for manual actuation, can be fixedly attached to the shank 711.

The tip 713 can include an active or cutting surface that is confluent with the working portion 712 (for example, like the tip shown in FIGS. 43 and 44). Alternatively, the leading tip 713 can include a non-active or non-cutting surface that is confluent with the working portion 712.

In the depicted embodiment, the MnFD 717 is located near the shank 711 end of the working portion 712, and the MxFD 718 is located near the tip 713. The shank 711 above the working portion 712 is essentially cylindrical and exhibits a slightly larger diameter than the cutting surface at the MnFD 717. With reference in particular to FIGS. 41 and 42, those skilled in the art will recognize that the center of mass 741 of a cross-section at the MnFD 717 (cross-section A-A shown in FIG. 40) is offset from the axis of rotation 740 of the offset drill and/or reamer 710. In addition, the center of mass 741 of a cross-section at the MxFD 718 (cross-section B-B shown in FIG. 41) is also offset from the axis of rotation 740. While the centers of mass of the cross-sections 717 and 718 (and the centers of mass of the cross-sections therebetween) are offset from the axis of rotation, in this embodiment the pointed end of the tip 713 coincides with the axis of rotation. However, in alternative embodiments the pointed end of the tip can also be offset from the axis of rotation.

As shown in FIGS. 37-42, the offset drill and/or reamer 710 defines three continuous helical flutes 720A, 720B, and 720C that spiral along the length of the working portion 712. In the depicted embodiment, the flutes 720A, 720B, and 720C are substantially concave grooves that follow the circumference of the working portion 712 as spirals between the shank 711 and the leading tip 713 to define concentric circles. In some embodiments, the flutes 720A, 720B, and 720C may be equidistant from each other. In some embodiments, the flutes 720A, 720B, and 720C may become increasingly tighter or more numerous as they approach the tip 713, or decreasingly tighter or less numerous as they approach the tip 713. The total number of turns per flute of the flutes 720A, 720B, and 720C from MnFD 717 to the MxFD 718 can depend on the total length of the working portion 712, but is typically not less than one quarter of one complete revolution. Helical flutes 720A, 720B, and 720C each originate at the MnFD 717 at separate locations that are spaced relatively equally apart around the circumference of the shank 711, or more specifically at about 120° of separation. Alternatively, in some embodiments helical flutes 720A, 720B, and 720C can originate at the MnFD 717 at separate locations that are spaced relatively unequally apart around the circumference of the shank 711 (e.g., at 105°, 120°, and 135°).

Figure 40:
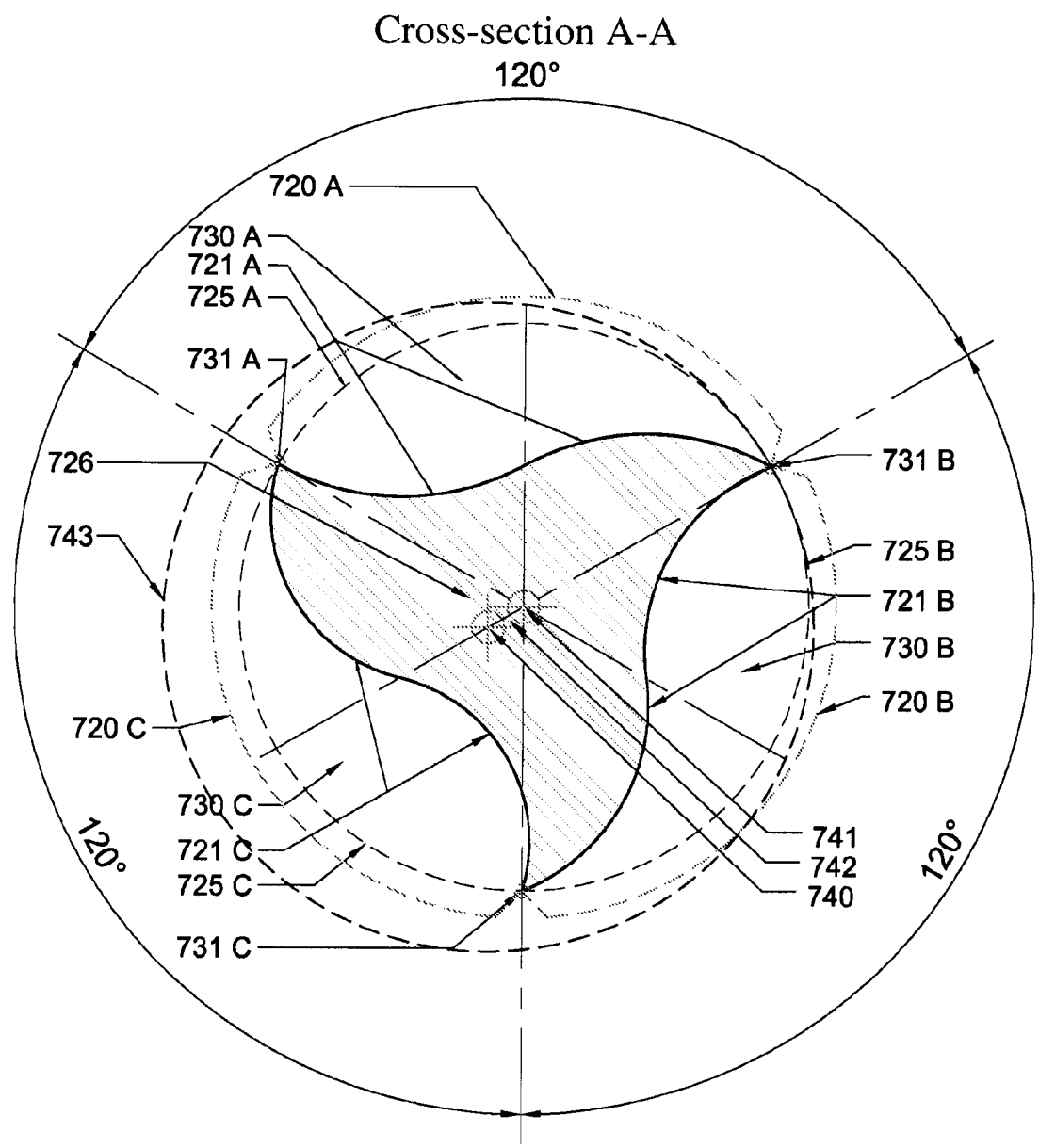
FIGS. 40 and 41 are transverse cross-sectional views of the three-sided rotary offset drill and/or reamer of FIG. 37 taken at sections A-A and B-B respectively.
Figure 41:
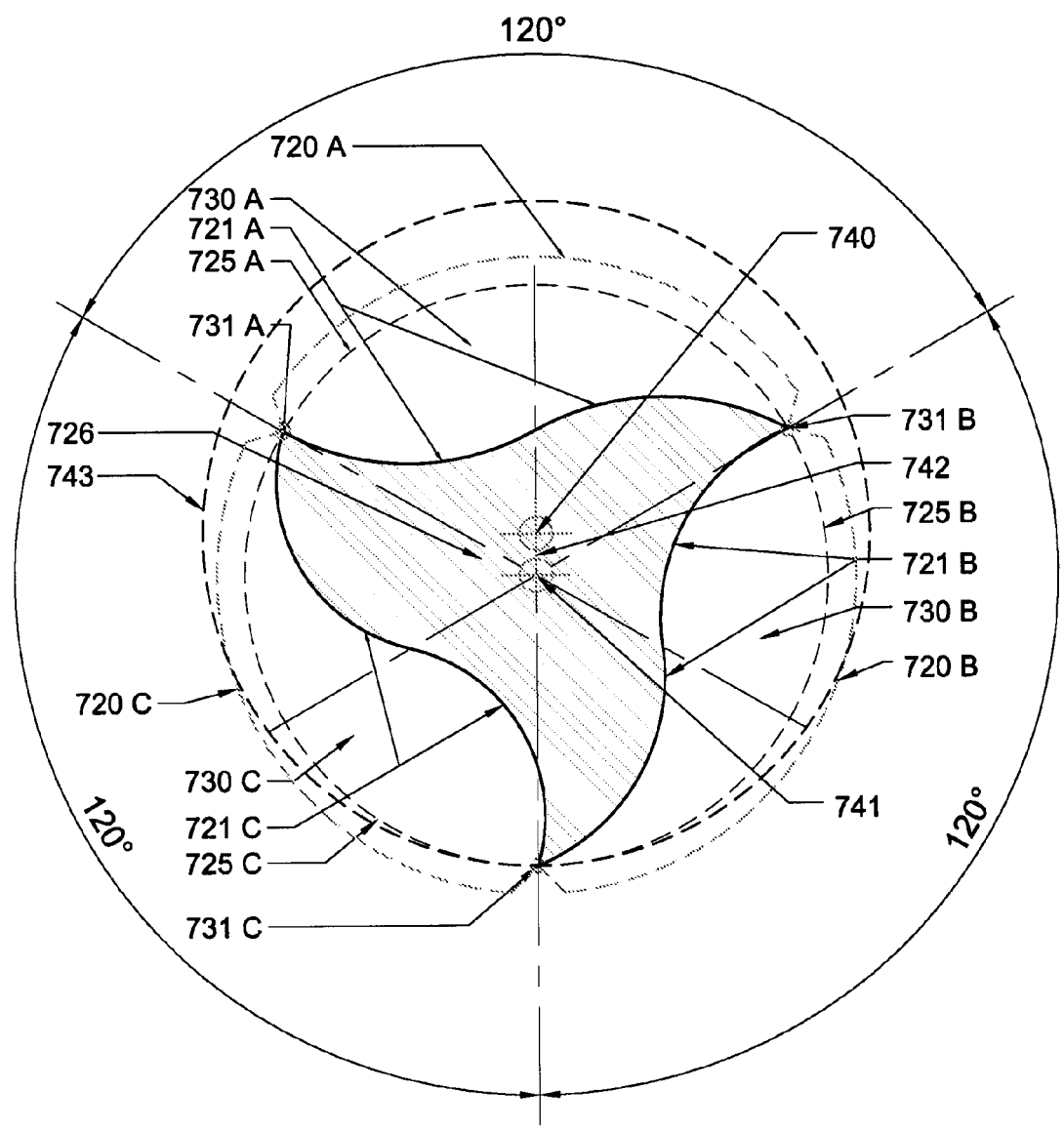
Figure 42:
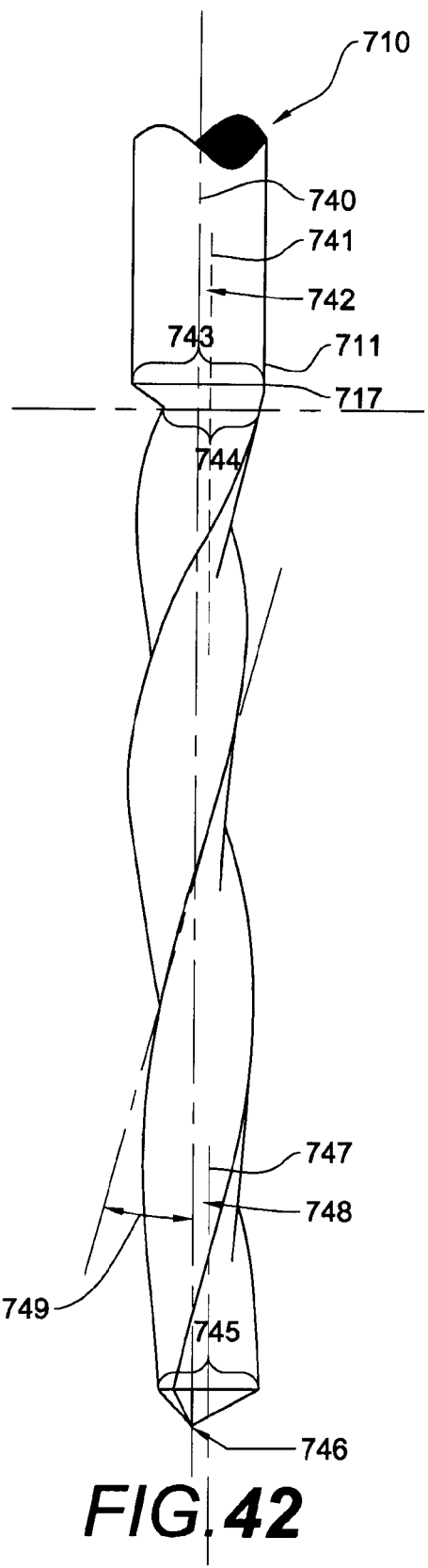
FIG. 42 depicts the three-sided rotary offset drill and/or reamer of FIG. 37, and demarcates the axis of rotation and the center of mass path defined by the centroids of all transverse cross-sections. In this embodiment, the axis of rotation and the center of mass path of all transverse cross-sections are essentially parallel.

With further reference to FIGS. 40 and 41, it can be seen that the S-shaped splines 721A, 721B, and 721C define cutting edges at points 731A, 731B, and 731C. In some embodiments, these intersections are equal distances apart, and at about 120° of separation to form a neutral cutting angle (90° angle to the tangent of the perimeter of shank 711) or slightly positive rake angle (greater than 90° to the tangent of the perimeter of the shank 711). It should be recognized that this cutting angle may be either negative or positive (that is, less than or greater than 90° to the tangent of the perimeter of the shank 711). In this embodiment, lines drawn to connect points 731A, 731B, and 731C form an equilateral triangle. However, those skilled in the art will also recognize that points 731A, 731B, and 731C may be separated by varying degrees and/or distances rendering the cross-section albeit triangular, asymmetrical (for example, at 110, 125, and 125 degrees of separation, or at other degrees of separation). It will also be recognized that splines 721A, 731A, and 721C may be variable in depth and shape (e.g., linear, J-shaped, etc.) and may have any of a myriad of different configurations.

In this example offset drill and/or reamer 710, the splines 721A, 721B, and 721C are S-shaped and are individually symmetrical. The bisector of each spline divides the spline equally into convex and a concave segments which form the S-shaped profile. The lines that bisect each spline 721A, 721B, and 721C can be drawn to the centroid 741 of the core 726 and are equal in length. Further, an alternate bisector can be drawn from the bisect center point of each spline 721A, 721B, and 721C through the greatest concavity the adjacent spline 721A, 721B, and 721C. Lines drawn perpendicular to the alternate bisector lines form an equilateral triangle. The bisectors for each spline 721A, 721B, and 721C are equal. As mentioned previously, the greatest depth of each spline 721A, 721B, and 721C can vary in some embodiments. While the depth and height of each spline 721A, 721B, and 721C can vary, the cross-sectional diameter of the core portion 727 is generally not narrower than about 20% percent of the diameter of the shank 711. However, in some embodiments, the cross-sectional diameter of the core portion 727 can be narrower than about 20% percent of the diameter of the shank 711.

As stated above, the offset drill and/or reamer 710 is an example of a three-sided rotary offset drill and/or reamer embodiment. In regard to the offset feature, and referencing FIGS. 40-42 in particular, the drill 710 has an axis of rotation 740 (about which the drill 710 rotates when in use), and a mass axis 741 that does not consistently coincide with the axis of rotation 740. In other words, the mass axis 741 is offset from the axis of rotation 740. The mass axis 741 is the continuum of points defined by the collection of the centroids (centers of mass) of each consecutive transverse cross-sectional area along the working portion 712. In this embodiment, the mass axis 741 is offset from the axis of rotation 740 by a distance 742. In this embodiment, the offset distance 742 remains relatively consistent from the shank 711 to the tip 713, and linear. This unique offset feature allows the instrument 710 to cut with a precessional motion. Accordingly, the offset drill and/or reamer 710 cuts a cavity or hole that is substantially cylindrical. Further, in some implementations the precessional motion results in, at any position along the working body 712, at least one of cutting edges 731A, 731B, or 731C is out of contact with the material being cut by the cutting instrument 710.

In some embodiments, some or the entire mass axis can be offset from the axis of rotation. Other spatial relationships may exist therebetween (other than the relatively consistent distance 742 and linear mass axis 741 of drill bit 710). For example, in some embodiments some or the entire mass axis 741 can approximate a helical form that revolves around the axis of rotation 740. In other embodiments, some or the entire mass axis 741 can form a spiral around the axis of rotation 740. In some embodiments, the mass axis 741 can intersect the axis of rotation along a portion of the working length 712 of the instrument 710, and can be offset from the axis of rotation 740 along other portions of the working length 712. In particular embodiments, the mass axis 741 intersects the axis of rotation 740 at one or more points, while other points of the mass axis 741 are offset from the axis of rotation 740. For example, in some embodiments the mass axis 741 can form a wavy, sinusoidal, or curved shape that may intersect the axis of rotation 740 at one or more points.

While alternative spatial relationships between the center of mass path 741 and axis of rotation 740 are described above in the context of cutting instrument 710, it should be understood that the alternative spatial relationships can be implemented in any of the other cutting instruments provided herein, and in any hybrid cutting instrument comprised of a combination of features from various exemplary embodiments provided herein.

FIGS. 45-50 illustrate another example offset drill and/or reamer 810. The offset drill and/or reamer 810 is an example of a four-sided rotary offset cutting instrument embodiment. The offset drill and/or reamer 810 has four sides, is both quadrilateral and radial in transverse cross-section. The offset drill and/or reamer instrument 810 includes a shank 811, a free end or tip 813, and a working portion 812 therebetween. In this embodiment, the diameter of the working portion 812 is slightly tapered, that is, increasing in diameter from the shank 811 to the tip 813. In other embodiments, the taper may be in the reverse direction, or the drill may have no taper. The working portion 812 of the drill 810 defines four flutes 820A, 820B, 820C and 820D. As will be described further, this embodiment of the offset drill and/or reamer 810 and can be utilized to remove material in a variety of applications during drilling and/or reaming creating a hole that is generally cylindrical.

An engine driven motor actuator with a hand-piece and/or chuck, or a handle utilized for manual actuation, can be fixedly attached to the shank 811.

The tip 813 can include an active or cutting surface that is confluent the working portion 812. Alternatively, the leading tip 813 can include a non-active or non-cutting surface that is confluent with the working portion 812.

Figure 48:
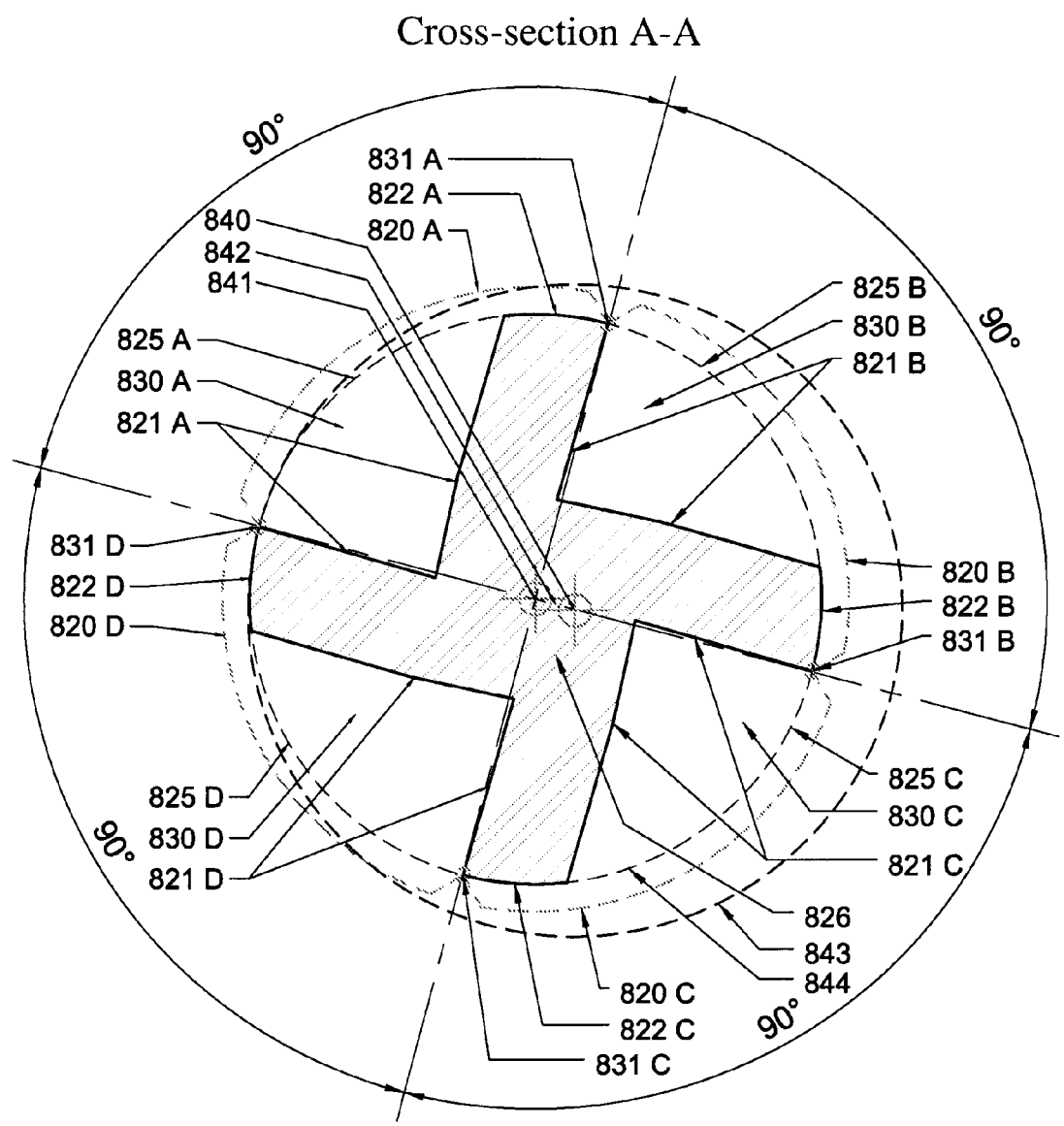
FIGS. 48 and 49 are transverse cross-sectional views of the four-sided rotary offset drill and/or reamer of FIG. 45 taken at sections A-A and B-B respectively.
Figure 49:
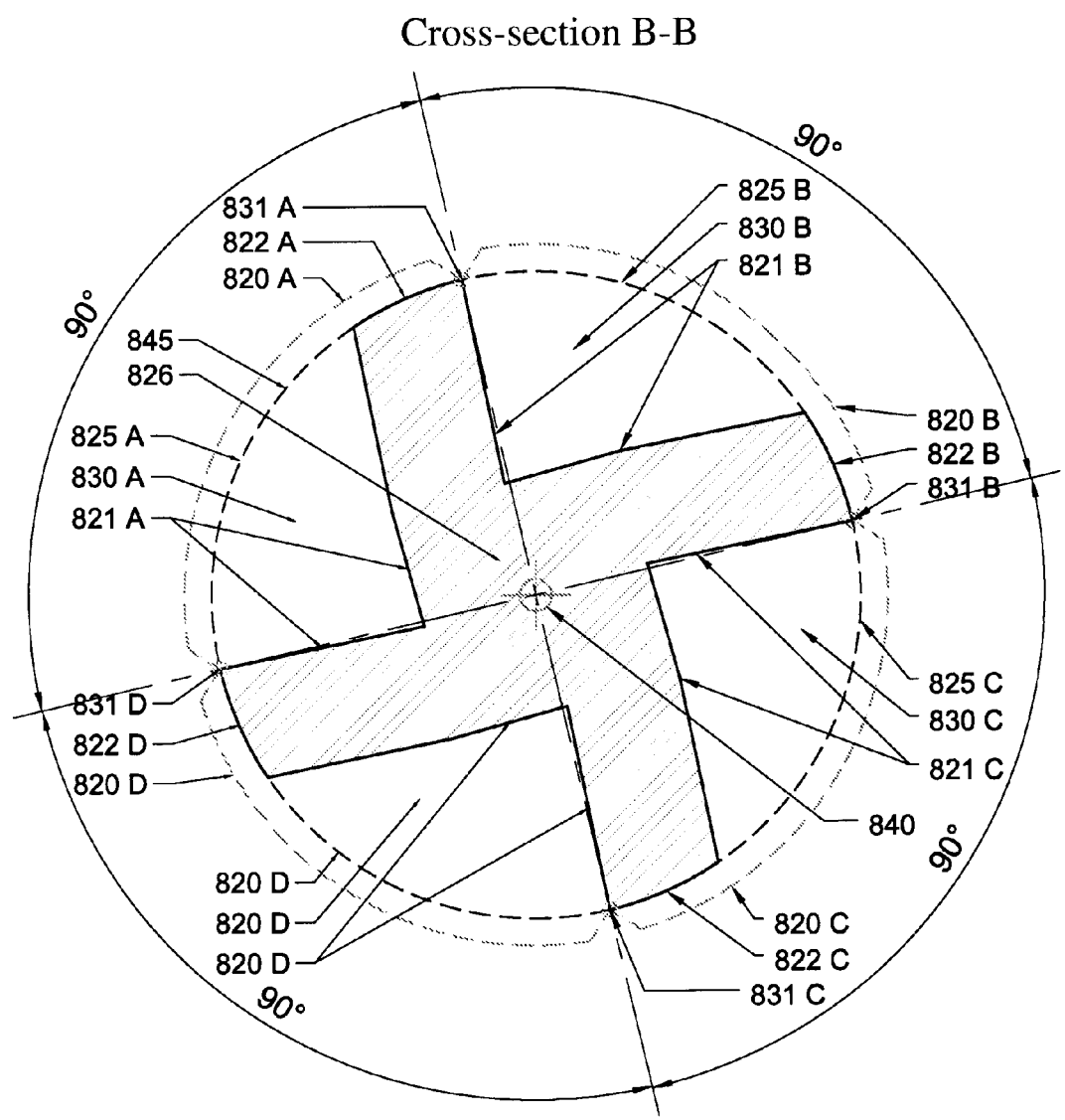
Figure 50:
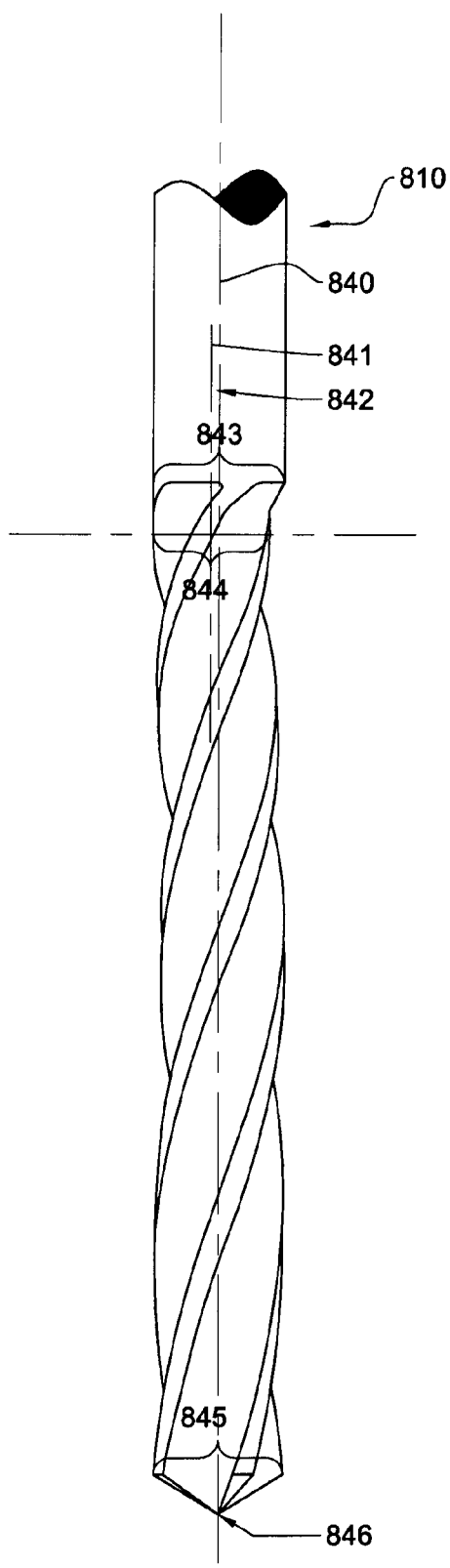
FIG. 50 depicts the four-sided offset drill and/or reamer of FIG. 45, and demarcates the center of rotation and a cross-sectional center of mass, which are offset from each other.

The MnFD 817 is located near the shank 811 end of the working portion 812. The MxFD 818 is located near the tip 813. The shank 811 above the working portion 812 is essentially cylindrical and exhibits a slightly larger diameter than the cutting surface at the MnFD 817. With reference in particular to FIGS. 48-50, those skilled in the art will recognize that the center of mass 841 of a cross-section at the MnFD 817 is offset from the axis of rotation 840 of the offset drill and/or reamer 810. However, the center of mass of a cross-section at the MxFD 818 coincides with the axis of rotation 840.

As shown in FIGS. 45-50, the offset drill and/or reamer 810 defines four continuous helical flutes 820A, 820B, 820C, and 820D. The flutes 820A, 820B, 820C, and 820D are angular groves which follow the circumference of the working portion 812 as spirals between the shank 811 and the leading tip 813 to define concentric circles. In some embodiments, the flutes 820A, 820B, 820C, and 820D may be equidistant from each other. In some embodiments, the flutes 820A, 820B, 820C, and 820D may become increasingly tighter or more numerous as they approach the tip 813, or decreasingly tighter or less numerous as they approach the tip 813. The total number of turns per flute of the flutes 820A, 820B, 820C, and 820D from MnFD 817 to the MxFD 818 can depend on the total length of the working portion 812, but is generally not less than one-quarter of a complete revolution. In some embodiments, helical flutes 820A, 820B, 820C, and 820D each originate at the MnFD 817 at separate locations, and are equally spaced apart around the circumference of the shank 811, or more specifically are at about 90° of separation. Alternatively, the helical flutes 820A, 820B, 820C, and 820D can originate at locations that are unequally spaced apart around the circumference of the shank 811 (e.g., at about 85°, about 95°, about 85°, and about 95°, in one such example).

With further reference to FIGS. 48 and 49, it can be seen that the angular splines 821A, 821B, 821C, and 821D associated with flutes 820A, 820B, 820C, and 820D intersect the periphery of the shank 811 at points 831A, 831B, 831C, and 831D. In this embodiment, these intersections are equal distances apart, and at about 90° of separation. It should be understood, however, that these intersections may be at different points of origin, such as at about 80°, 100°, 80°, and 100°, to provide another such example.

In this embodiment, splines 821A, 821B, 821C, and 821D form a neutral cutting angle (at about a 90° angle to the tangent of the perimeter of shank 811). Alternatively, the splines may form a positive rake angle (e.g., greater than 90° to the tangent of the perimeter of the shank 811). It is also recognized that this cutting angle may be negative (e.g., less than 90° to the tangent of the perimeter of the shank 811) or positive (e.g., more than 90° to the tangent of the perimeter of the shank 811). In this embodiment, lines drawn to connect points 831A, 831B, 831C, and 831D join to form a quadrilateral configuration. However, those skilled in the art will also recognize that points 831A, 831B, 831C, and 831D may be separated by varying degrees and/or distances rendering the cross-section albeit quadrilateral, asymmetrical, for example, at about 80, 85, 95, and 100 degrees of separation (or at other degrees of separation). It will also be recognized that splines 821A, 831B, 821C, and 821D may be variable in depth and shape and may have a wide variety of configurations.

In this example of an offset drill and/or reamer 810, the splines 821A, 821B, 821C, and 821D are angular (e.g., forming nearly a right angles) adjacent to the web or core 826, and the splines 821A, 821B, 821C, and 821D are individually approximately symmetrical. However, in some embodiments the splines 821A, 821B, 821C, and 821D may be asymmetrical.

The greatest depths of splines 821A, 821B, 821C, and 821D are dictated by the width of the core 826 and can be constant or variable. The cross-sectional diameter of the core portion 826, is, generally, not narrower than about 20% percent of the diameter of the shank 811. But in some cases, the cross-sectional diameter of the core portion 826 may be narrower than about 20% of the diameter of the shank 811.

As stated above, the offset drill and/or reamer 810 is an example of a four-sided rotary offset drill and/or reamer embodiment. In regard to the offset feature, and further referencing FIGS. 48-50, the drill 810 has a center-line or axis of rotation 840 (about which the drill 810 rotates when in use), and a mass axis 841 that at least partially does not coincide with the axis of rotation 840. The mass axis 841 is a line defined by the centers of mass of consecutive cross-sectional areas of the offset drill and/or reamer 810. The offset is the difference between the mass axis 841 and the axis of rotation 840, which are displaced a distance 842 away from each other. In this embodiment, the offset distance 842 decreases continuously from the shank 811 to the tip 813, and is zero at the end-point 846. This unique offset feature allows the instrument 810 to cut with a precessional motion, which carves a cutting envelope 843 using a cross-section with a smaller cross-section 844. Accordingly, the offset drill and/or reamer 810 cuts a cavity or hole that remains cylindrical and corresponds to the diameter of MxFD 818, with an drill that is substantially smaller in cross-section longitudinally. In other embodiments, the offset distance 842 can be different, e.g., zero at the shank 811 and increasing continuously to the tip 813. Alternatively, the degree of offset may be variable and/or may terminate at some distance short of the tip 813.

The features of the various offset drill and/or reamer embodiments described herein can be combined together in any suitable combination. For example, the offset drill and/or reamer 810 is an example of a four-sided rotary offset drill and/or reamer embodiment that increases in diameter from the shank 811 to the tip 813. Other embodiments can also be adapted to include such a taper and/or cross-sectional shape. For instance, an offset drill and/or reamer having the cross-sectional shape of offset drill and/or reamer 410, 510, 610, or 710 or could be used with tapered diameters of offset drill and/or reamer 810. All hybrid designs including combinations and sub-combinations of any and/or all of the features and designs provided herein are within the scope of this disclosure.

Figure 54:
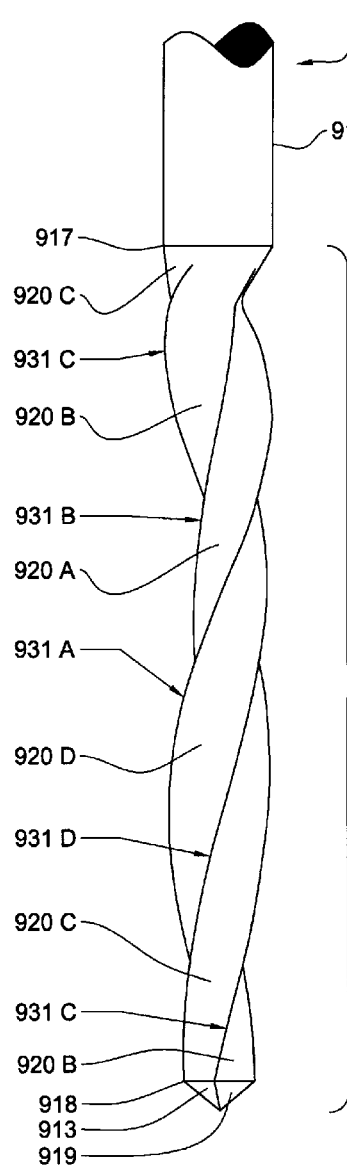
Figure 55:
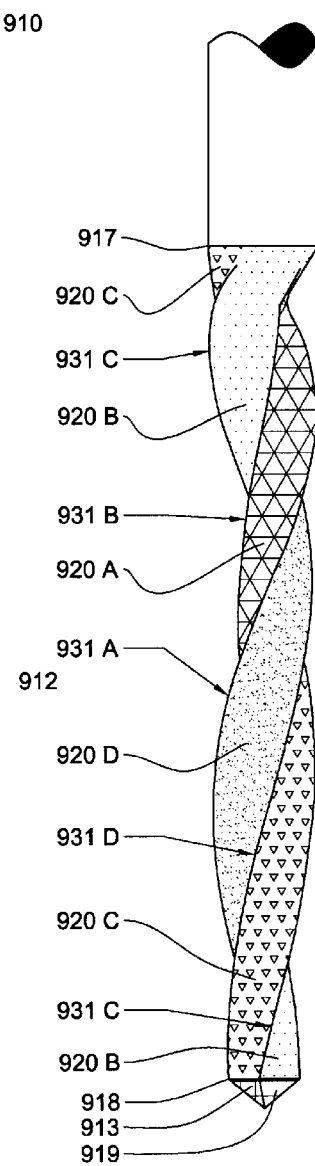
Figure 56:
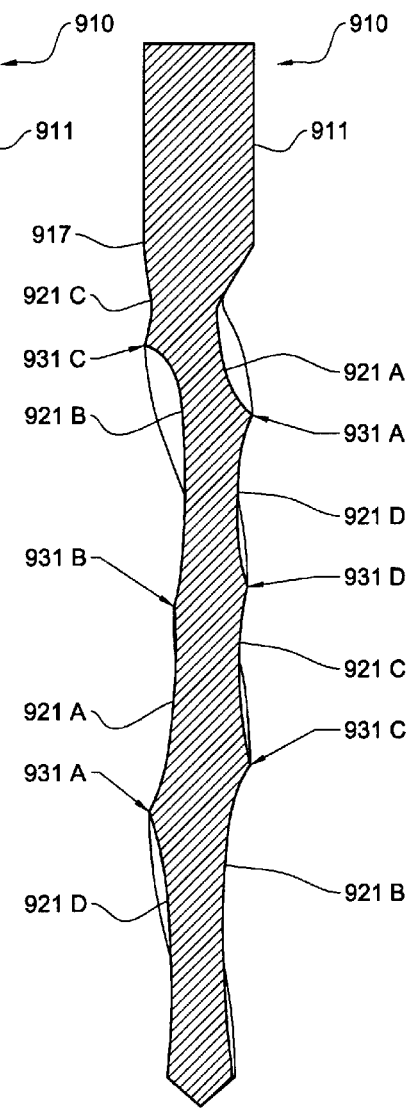

FIGS. 51-53, 54-56, 57, 58, and 67 illustrate another example offset drill and/or reamer 910. FIGS. 51-53 and 54-56 show the same offset drill and/or reamer 910, but the views are rotated 90° in relation to each other. That is, for example, FIG. 54-56 are the views of the offset drill and/or reamer 910 from a perspective that are rotated 90° from the views of FIG. 51-53.

The offset drill and/or reamer 910 is an embodiment of a four-sided rotary offset drill and/or reamer. The offset drill and/or reamer 910 has a transverse cross-section that is shaped approximately as a parallelogram. In these embodiments, the cross-sectional shape can also approximate a rhombus with varying degrees at the point angles, or a rectangle, square, trapezoid, triangle, and so on. The offset drill and/or reamer 910 and can be utilized to remove material in a variety of applications during drilling and/or reaming.

The offset drill and/or reamer instrument 910 includes a shank 911, a tip 913 (or free end), and a working portion 912 therebetween. In this embodiment, the diameter of the working portion 912 (as defined by the rotary path of points 931A and 931C, which are the intersections of the splines 921A with 921D, and 921B with 921C) is slightly tapered, that is, increasing in diameter from the shank 911 to the tip 913. In other embodiments, the taper may be in the reverse direction or the drill may have no taper. The working portion 912 of the drill 910 defines four flutes 920A, 920B, 920C, and 920D. As will be described further, this embodiment of the offset drill and/or reamer 910 cuts a cavity or prepares a hole that is generally cylindrical. An engine driven motor actuator with a hand-piece and/or chuck, or a handle utilized for manual actuation, can be fixedly attached to the shank 911.

The tip 913 can include an active or cutting surface that is confluent with the working portion 912. Alternatively, the leading tip 913 can include a non-active or non-cutting surface that is confluent with the working portion 912.

Figure 57:
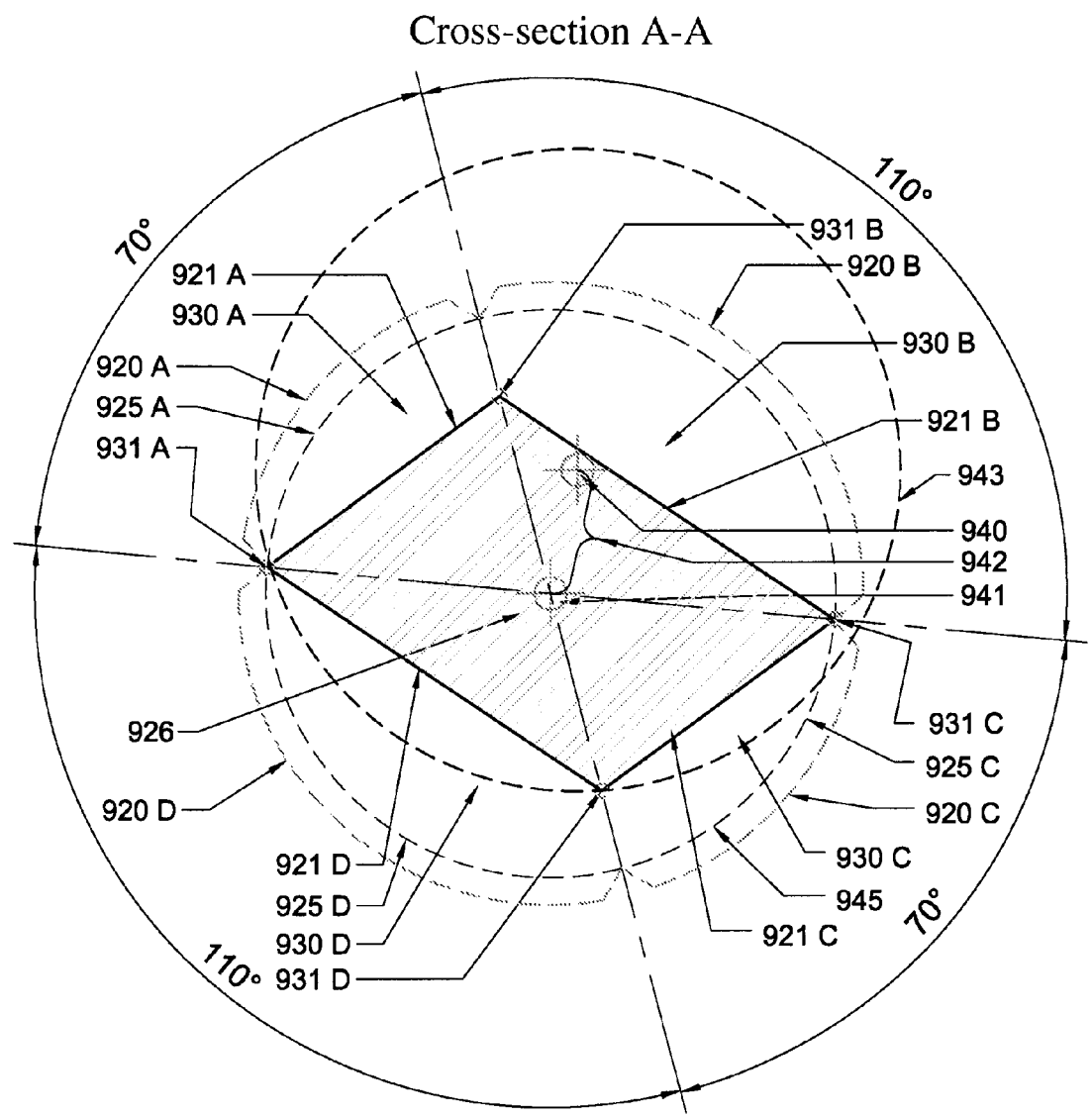
FIGS. 57 and 58 are transverse cross-sectional views of the four-sided rotary offset drill and/or reamer of FIG. 51 taken at sections A-A and B-B respectively.
Figure 67:
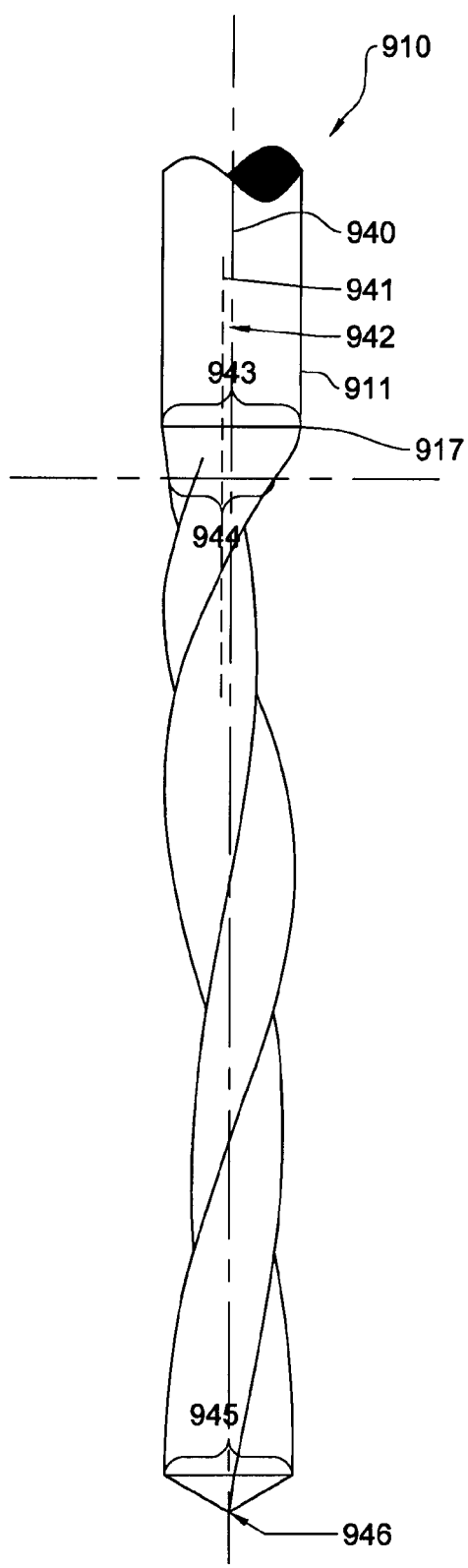
FIG. 67 depicts the four-sided rotary offset drill and/or reamer of FIG. 51, and demarcates the center of rotation and a cross-sectional center of mass, which are offset from each other.
Figure 68:
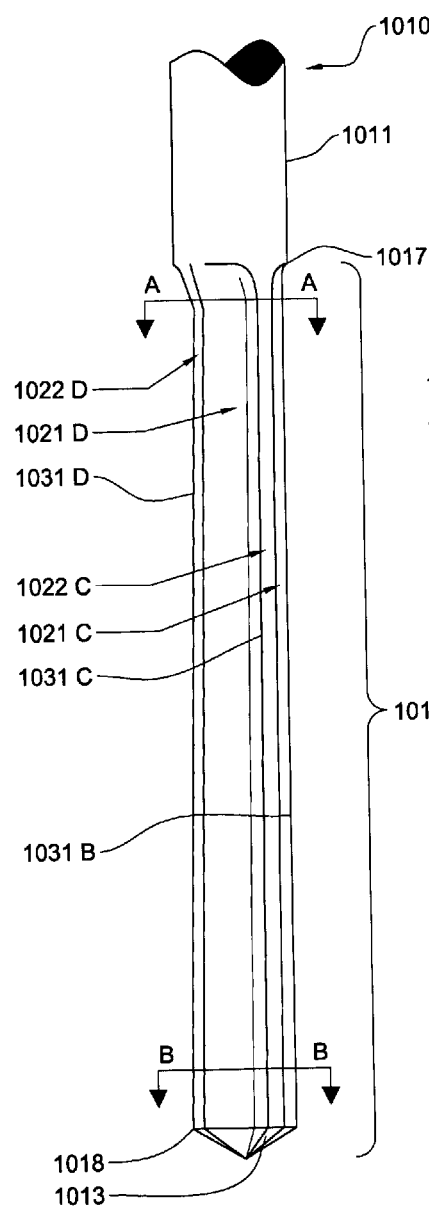
FIGS. 68-70 show views of an example three-sided rotary offset drill and/or reamer. This design has substantially straight flutes as opposed to flutes that revolve around the central axis. This device is designed to cut a parallel space and may be particularly useful in reaming.
Figure 69:
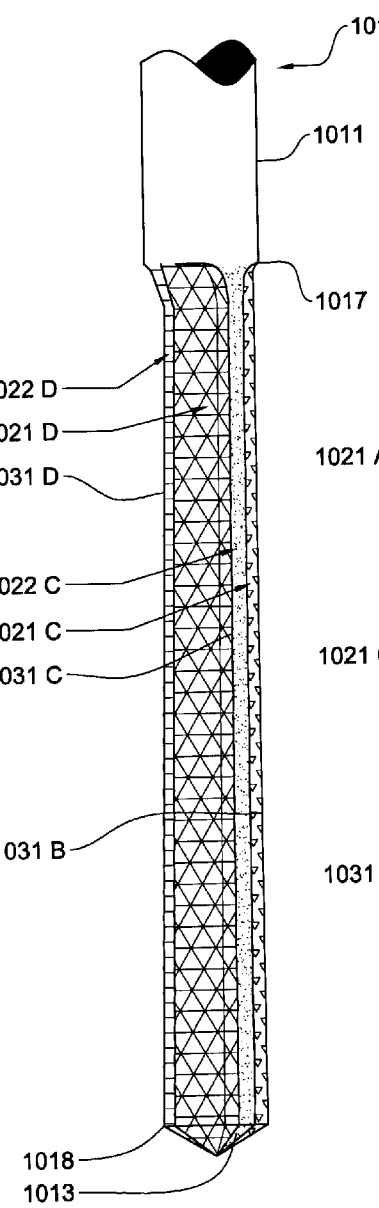
Figure 70:
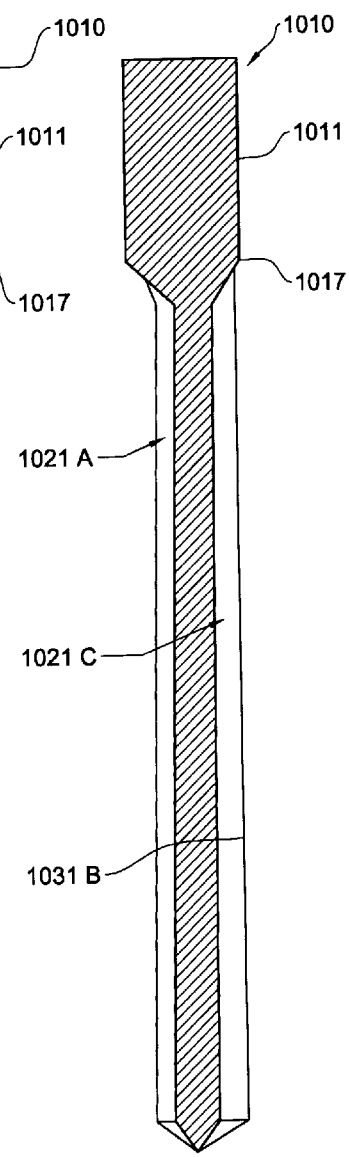

In this embodiment, the MnFD 917 is located near the shank 911 end of the working portion 912, and the MxFD 918 is located near the tip 913. In other embodiments, the locations of the MnFD and MxFD can be anywhere elsewhere along the working portion 912. The shank 911 above the working portion 912 is essentially cylindrical and exhibits a slightly larger diameter than the cutting surface at the MnFD 917. With reference in particular to FIGS. 57, 158, and 67, those skilled in the art will recognize that the center of mass 941 of a cross-section at the MnFD 917 (e.g., refer to FIG. 57) is offset from the axis of rotation 940 of the offset drill and/or reamer 910. However, in the depicted embodiment the center of mass of a cross-section at the MxFD 918 coincides with the axis of rotation 940. In other embodiments, the centers of mass of cross-sections at various positions along the working portion of an instrument may form a mass axis that has a different spatial relationship from the axis of rotation (i.e., different than the spatial relationship between the mass axis and axis of rotation defined by drill 910). For example, as described above, some or the entire mass axis may be helical (spiral-shaped), wavy, canted, curved, or linear, but offset from the axis of rotation, or partially coincident to the axis of rotation, and so on. In some embodiments, combinations of such features can be included in a single instrument.

As shown in FIGS. 51-53, 54-56, 57, 57, and 67, the offset drill and/or reamer 910 defines four continuous helical flutes 920A, 920B, 920C, and 920D that revolve around the central axis 940. In this embodiment, the splines 921A, 921B, 921C, and 921D are generally planar surfaces. In alternative embodiments, the splines 921A, 921B, 921C, and 921D have curved profiles with one or more concave or convex portions, S-shaped profiles, J-shaped profiles, and the like. Consistent with the parallelogram cross-sections shown in FIGS. 57 and 58, the flutes 920A, 920B, 920C, and 920D form a bi-symmetrical rectilinear shape with flutes 920A and 920C being relatively equal and circumscribing the smallest arc, and flutes 920B and 920D being relatively equal and circumscribing the widest arc. Those skilled in the arc will recognize that the arc lengths may vary such that asymmetrical cross-sectional shapes can be defined in some embodiments. In this embodiment, these arcs will, again, display bi-symmetry and revolve around the axis at a relatively equal rate from shank to tip. In other embodiments, the flutes 920A, 920B, 920C, and 920D may become increasingly tighter or more numerous as they approach the tip 913 (or tighter at the shank end). The total number of turns per flute of the flutes 920A, 920B, 920C, and 920D from MnFD 917 (refer to cross-section A-A shown in FIG. 57) to the MxFD 919 (refer to cross-section B-B shown in FIG. 58) can depend on the total length of the working portion 912, but is generally not less than one-quarter of a complete revolution.

Figure 58:
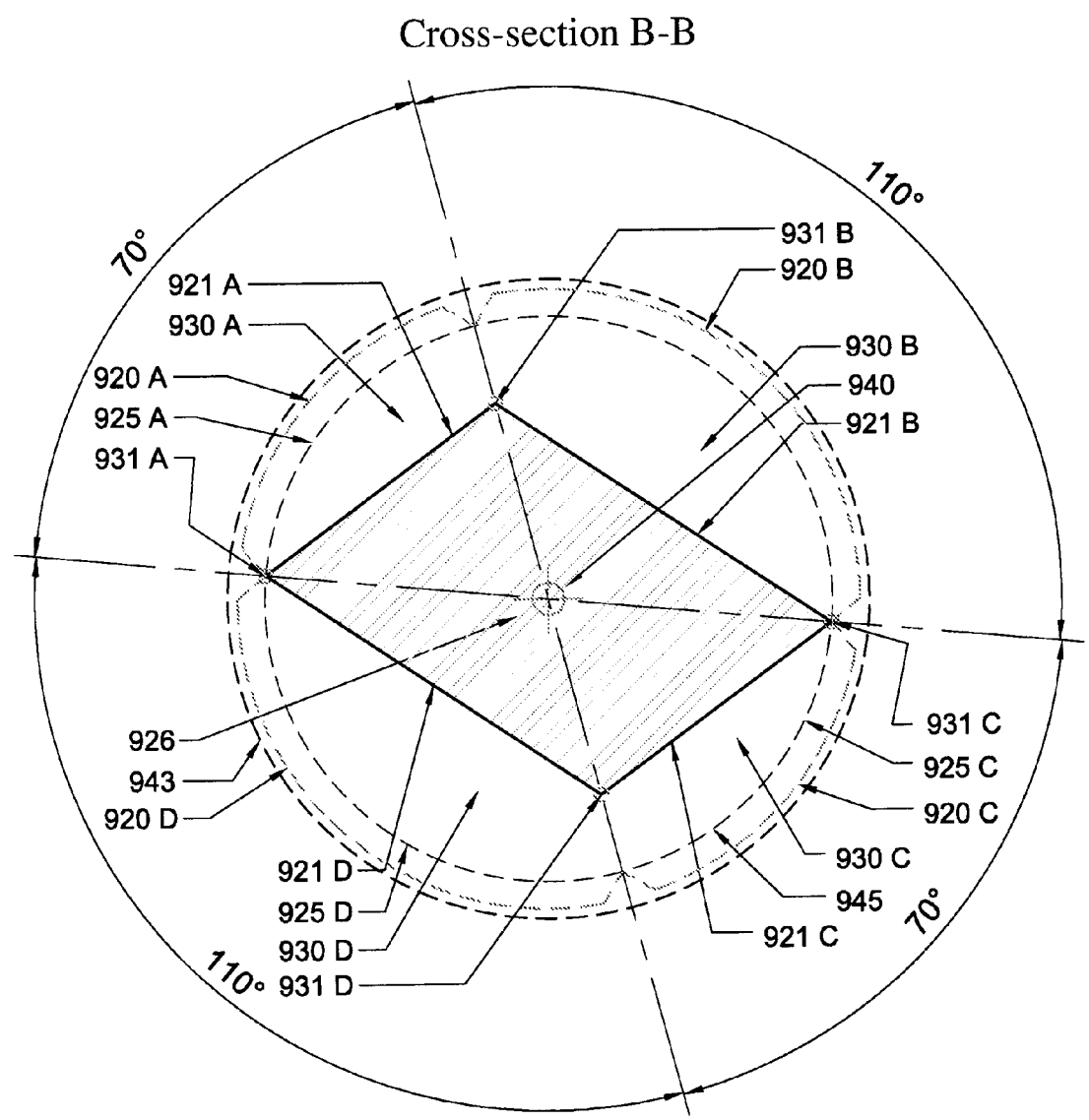

With further reference to FIGS. 57 and 58, it can be seen that the splines 921A, 921B, 921C, and 921D associated with flutes 920A, 920B, 920C, and 920D intersect at points 931A, 931B, 931C, and 931D. In this embodiment, the intersections 931A, 931B, 931C, and 931D define arcuate segments therebetween at angles of about 70°, 110°, 70°, and 110°. It should be understood, however, that other angles may be used in other embodiments, such that the shape of the transverse cross-section may become narrower, wider, asymmetrical, triangular, and so on. In addition, the shape of the transverse cross-sections may vary along the working length of the instrument. For example, the shape of a transverse cross-section near the shank may be rhomboidal and the shape of a transverse cross-section elsewhere may be a parallelogram as depicted in FIG. 58 (or another type of shape). In another example, the shape of a transverse cross-section near the shank may be parallelogram and the shape of a transverse cross-section near the tip FIG. 58 is a square (or some other shape). A configuration whereby the shape varies from being substantially rectilinear at the shank to substantially square at the tip anticipates a requirement for greater strength at the tip end.

In this embodiment, splines 921A, 921B, 921C, and 921D form negative cutting angles tangent with the perimeter of shank 911. Alternatively, the splines may form a neutral or positive rake angle tangent with the perimeter of the shank 911.

It will also be recognized that splines 921A, 931B, 921C, and 921D may include concaved portions that can be formed to have various depths, shapes and may have a wide variety of configurations. The greatest depths of splines 921A, 921B, 921C, and 921D is affected by the width of the core 943, and the depths can be constant or variable along the working portion 912. The cross-sectional diameter of the core portion 943 is generally not narrower than about 20% percent of the diameter of the shank 911. However, in some embodiments the cross-sectional diameter of the core portion 943 can be narrower than about 20% percent of the diameter of the shank 911.

Figure 59:
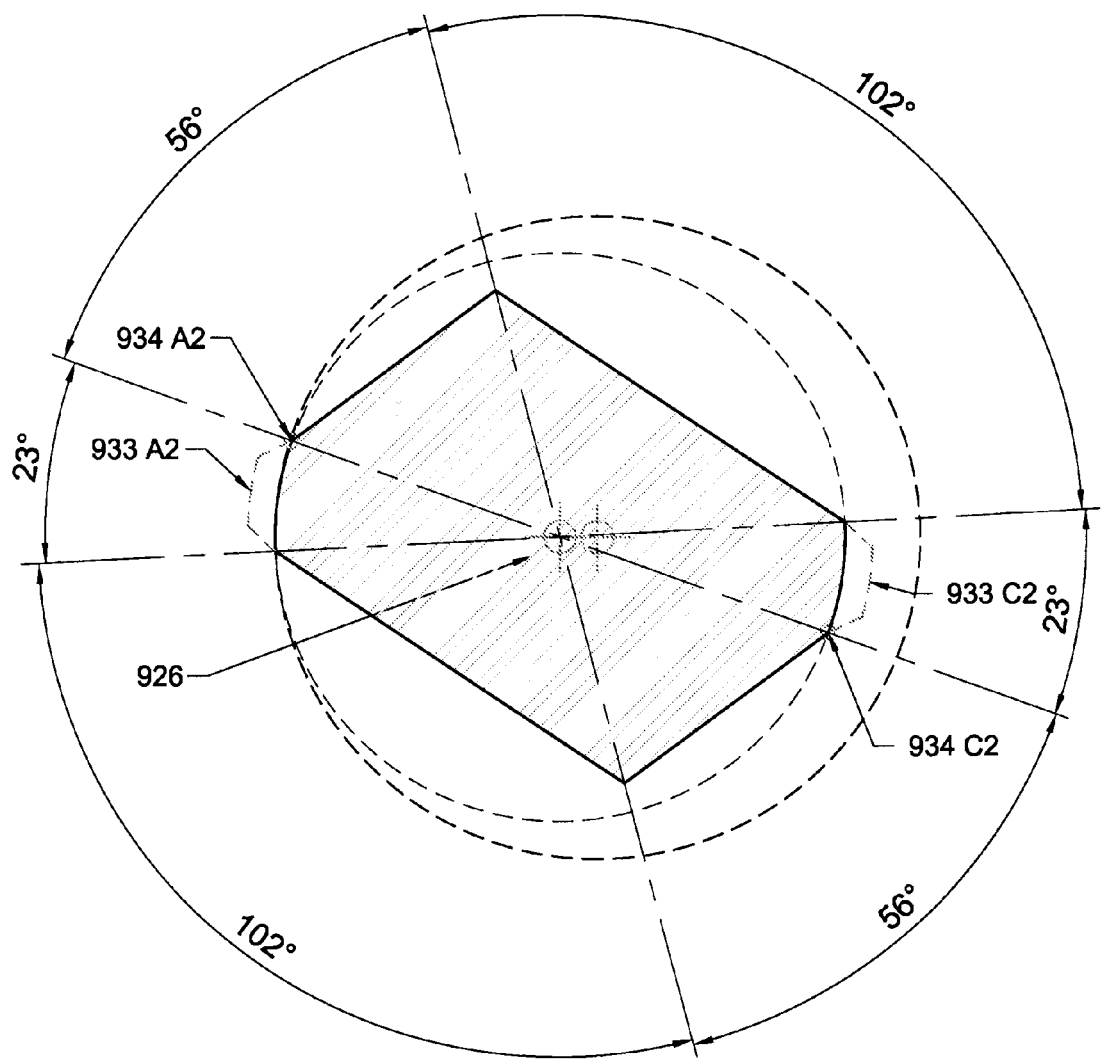
FIGS. 59 and 60 are alternate transverse cross-sections of the four-sided rotary offset drill and/or reamer of FIG. 51 taken at sections A-A and B-B respectively and featuring margins.
Figure 60:
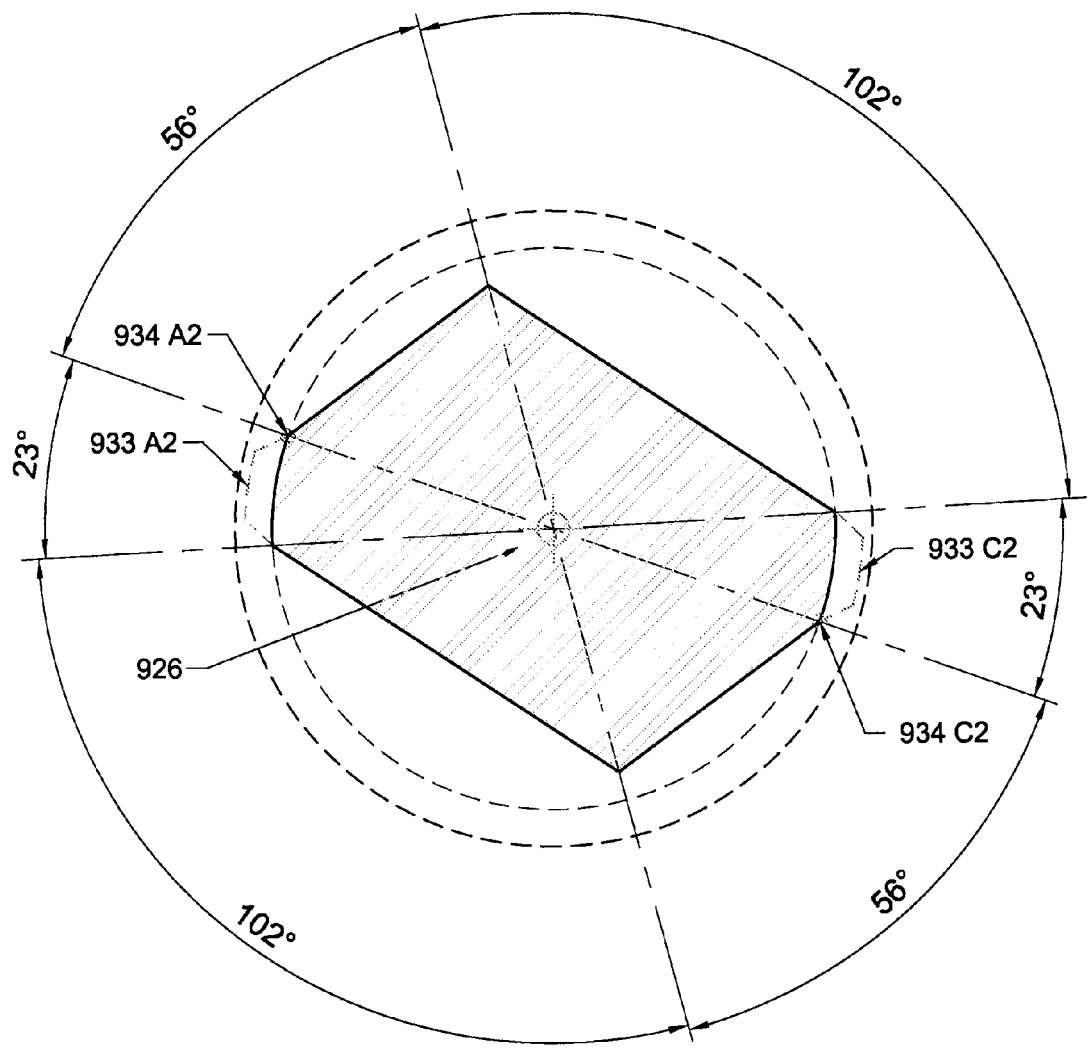

FIGS. 59 and 60 are alternate transverse cross-sections of a drill body 51-53 and 57. This embodiment features a more modest degree of offset whereby cutting is accomplished along the leading edges associated with margins 933A and 933C. A design of this nature can further strengthen and stabilize the device.

Figure 61:
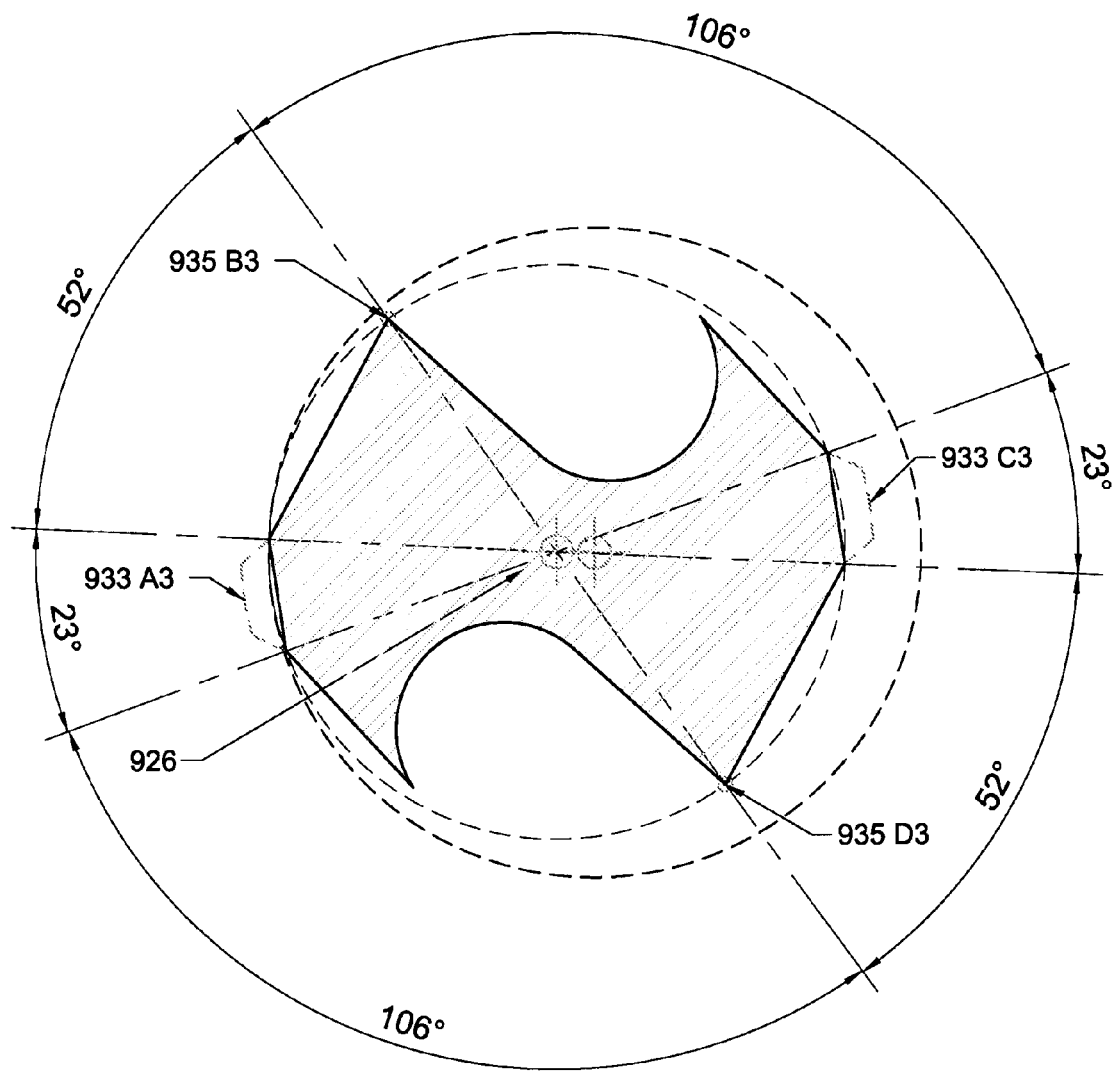
FIGS. 61 and 62 are alternate transverse cross-sections of the four-sided rotary offset drill and/or reamer of FIG. 51 taken at sections A-A and B-B respectively and featuring margins that are separated from the leading edges.
Figure 62:
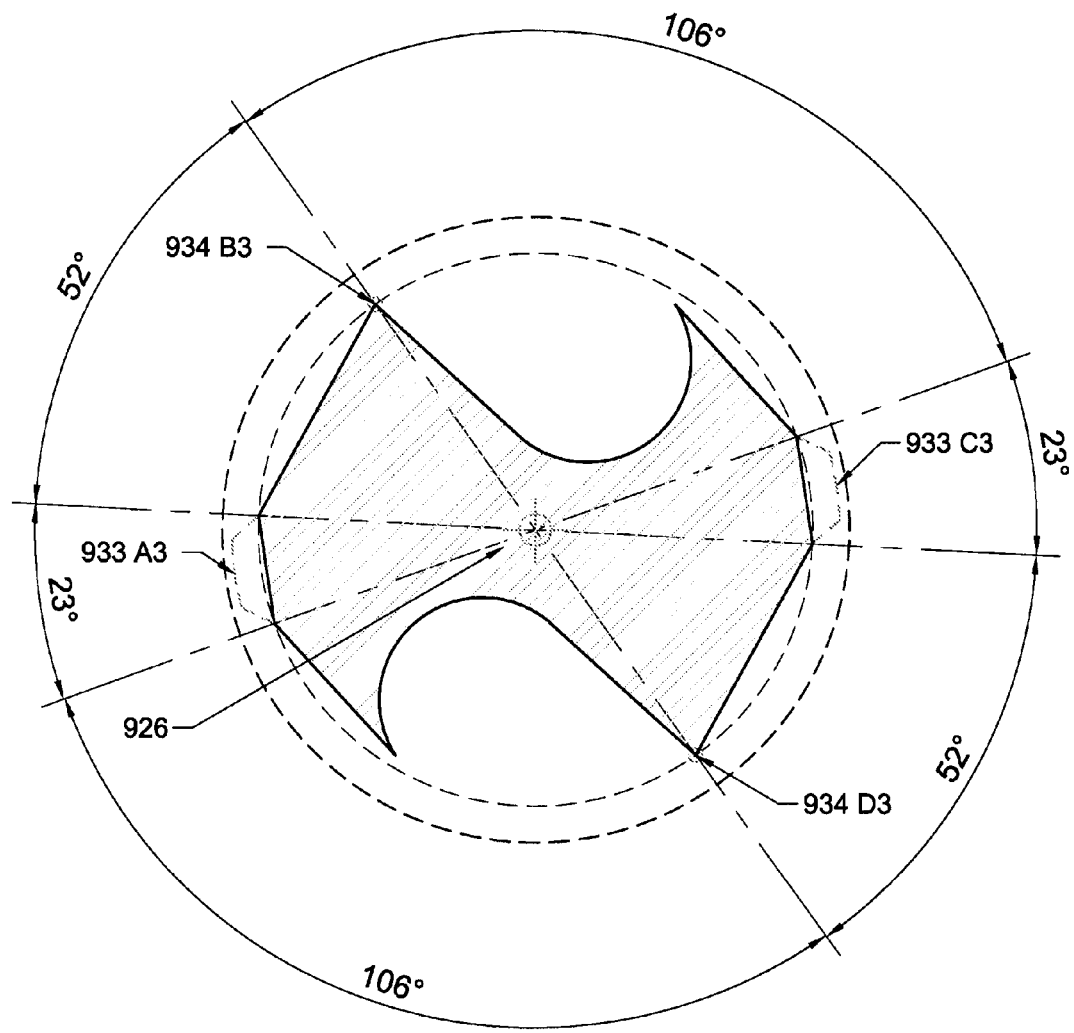

FIGS. 61 and 62 are alternate transverse cross-sections of a drill body also specifically designed for strength. FIG. 61 is taken at the shank end of the device and demonstrates and offset center of mass when compared to the axis of rotation. The offset continues toward the tip end progressively decreasing where the axis of rotation and center of mass correspond as shown in FIG. 62. This cross-section is a hybridization of the quadrilateral cross-section displayed in FIGS. 57 and 58 and the two-sided offset drill design in FIGS. 12 and 13 or 17 and 20, which featured J-shaped flutes. This design exhibits a number of unique features, the most notable, of which, are the margins 933A and 933C, which are placed at a distance behind the leading edges 933B and 933D. A design of this nature not only serves to maximize the cross-sectional area of the core or web 926 adding additional core strength, but allows the cutting edges work independently and unimpeded by the margins that now in the middle of the land. The cutting edges can now work in a pure cutting modality, while the margins, which add stability, can act as a burnishing feature, which may be particularly useful in cutting metal.

Figure 63:
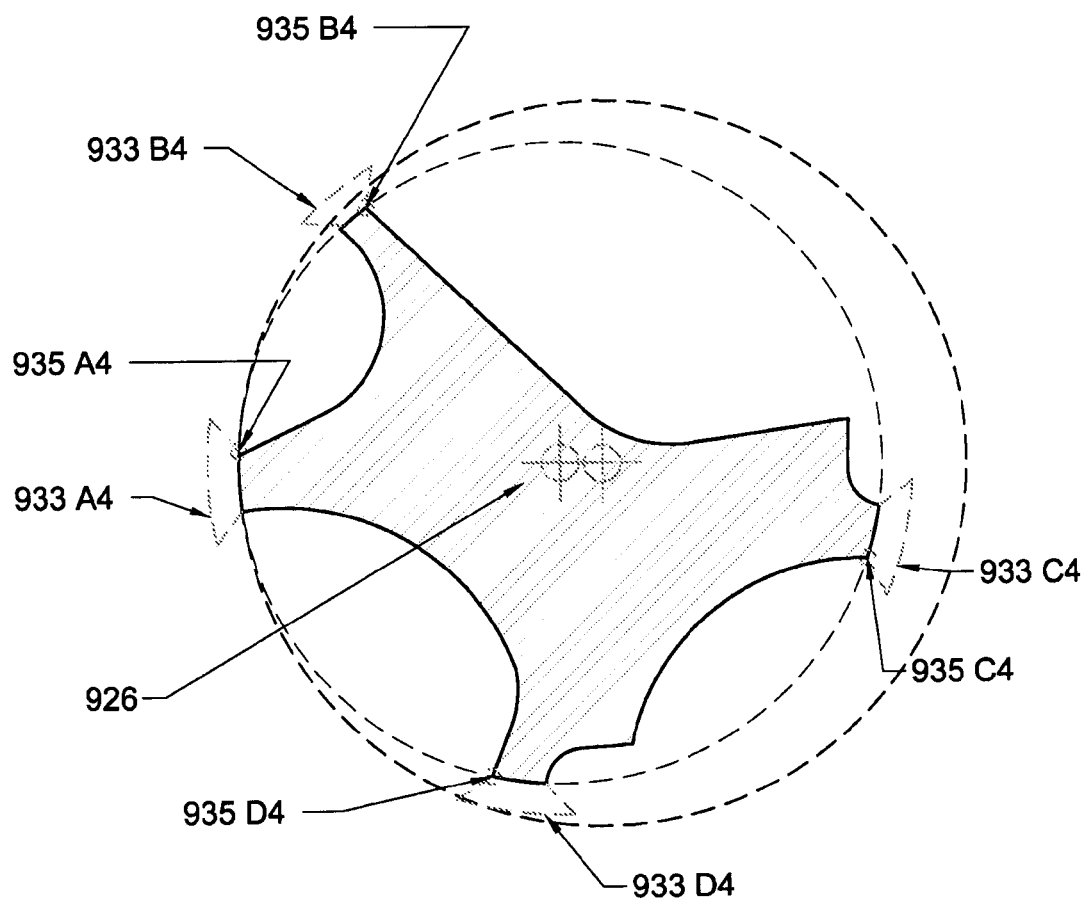
FIGS. 63 and 64 are alternate transverse cross-sections of the four-sided rotary offset drill and/or reamer of FIG. 51 taken at sections A-A and B-B respectively and featuring a multi-faceted asymmetric cross-section with margins.
Figure 64:
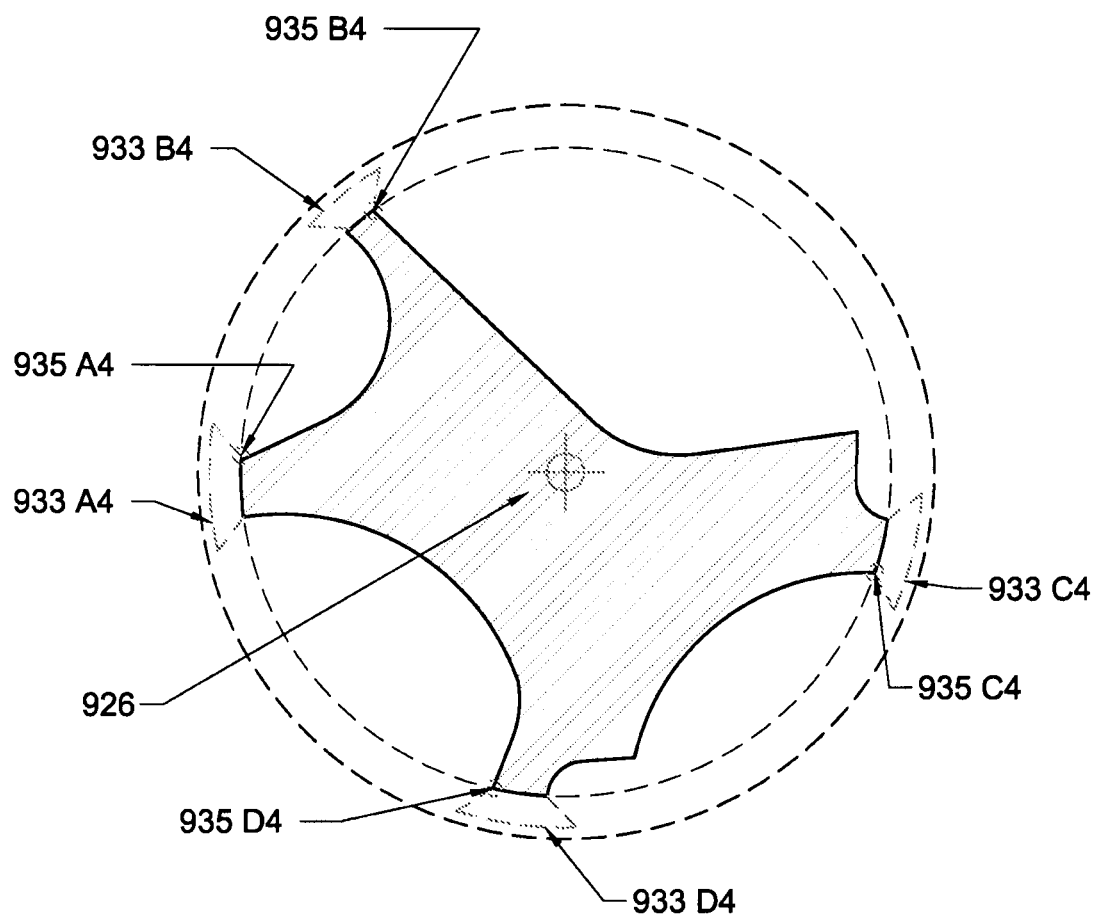

FIGS. 63 and 64 are alternate transverse cross-sections of a drill body also specifically designed for strength, penetrability, stability and chip breaking. FIG. 63 is taken at the shank end of the device and demonstrates and offset center of mass when compared to the axis of rotation. The offset continues toward the tip end progressively decreasing where the axis of rotation and center of mass correspond as shown in FIG. 64. Although his cross-section takes on some of the features of the quadrilateral cross-section displayed in FIGS. 57 and 58, it is distinctly asymmetrical. This design exhibits a number of unique features, which include four leading edges 935A4, 935B4, 935C4, and 935D4 which are intended in some embodiments to be positive, and four margins 933A4, 933B4, 933C4, and 933D4, which are distributed in both and offset and asymmetrically configuration. Thus, a multi-faceted design emerges. Multi-faceted devices are known to require less axial force for penetration, are capable of self-centering, offer superior penetrability, a reduction or exit burrs and chip breaking. A cross-section of this nature, when combined with the offset feature, which is the hallmark of this application, can work synergistically to meet the most demanding needs in drilling.

Figure 65:
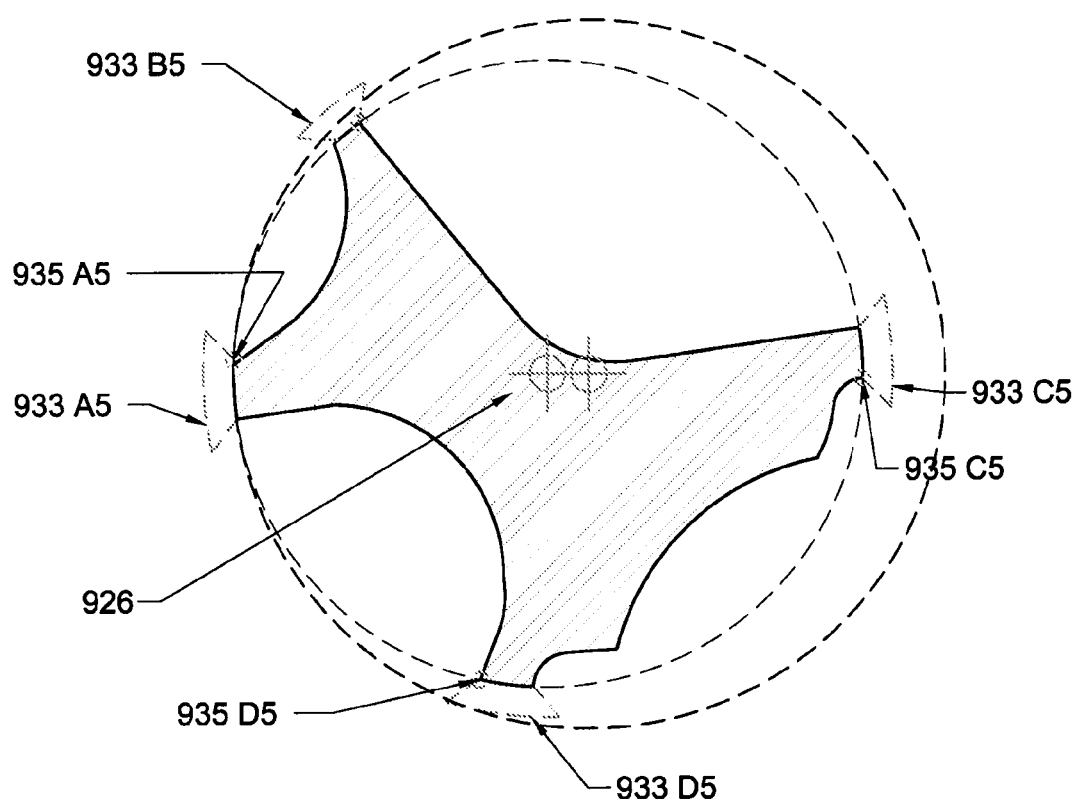
FIGS. 65 and 66 are alternate transverse cross-sections of the four-sided rotary offset drill and/or reamer of FIG. 51 taken at sections A-A and B-B respectively and featuring a multi-faceted asymmetric cross-section with margins that can cut in both a right handed and left handed direction.
Figure 66:
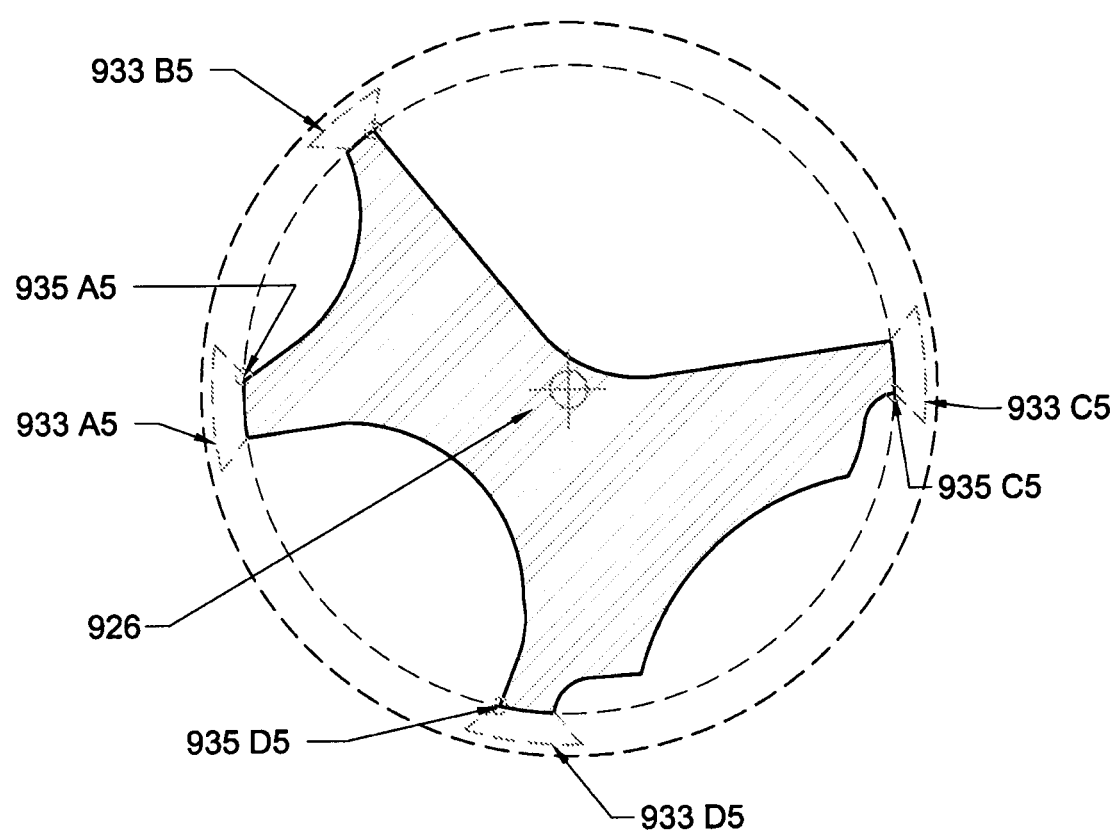

FIGS. 65 and 66 are alternate transverse cross-sections of a drill body also specifically designed for strength, penetrability, stability and chip breaking and is similar to FIGS. 63 and 64 in both design and function. It should be noted, however, that in FIGS. 65 and 66, the cutting edge 935C4 (in FIGS. 63 and 64) is reversed whereby the margin 933C5 is in front of the leading edge 935C5 assuming the device were rotating in a right handed or clockwise direction. Although a device of this nature is functional in right hand cut, it is, perhaps, more useful when used in reciprocation, i.e., alternately in a right handed and then left handed direction.

As stated above, the offset drill and/or reamer 910 is an example of a four-sided rotary offset drill and/or reamer that has the transverse cross-section of a parallelogram. In regard to the offset feature, and further referencing FIGS. 57, 58, and 67, the drill 910 has a center-line or axis of rotation 940 (about which the drill 910 rotates when in use), and a mass axis 941 that does not consistently coincide with the axis of rotation 940. The mass axis 941 is a continuum of points defined by the centers of mass (centroids) of consecutive cross-sectional areas of the offset drill and/or reamer 910 along the working portion 912. The offset is the spatial difference between the mass axis 941 and the axis of rotation 940 (which are displaced a distance 942 away from each other near the shank 911). In this embodiment, the offset distance 942 decreases from the shank 911 to the tip 913, and is about zero at the end-point 946. This unique offset feature allows the instrument 910 to cut with a precessional motion, which can remove material in an envelope at least as large as cutting envelope 943, while using an instrument with a smaller cross-section 944. Accordingly, the offset drill and/or reamer 910 cuts a cavity or prepare a hole that remains generally cylindrical and corresponds to the diameter of MxFD 918, with a drill 910 that is substantially smaller in cross-section. In other embodiments, the offset distance 942 can be different, e.g., about zero at the shank 911 and increasing to the tip 913, or the offset may be essential consistent from shank to tip as shown, for example, in the embodiment of FIGS. 37-42.

In some drill instrument embodiments having cross-sections shaped as a parallelogram, other spatial relationships can exist between the mass axis and the axis of rotation (that is, other than the distance 942 near the shank 911 and that decreases to about zero at the tip 913). For example, in some embodiments some or all of the mass axis can approximate a helical or corkscrew form that revolves around the axis of rotation. In other embodiments, the mass axis can form a three-dimensional spiral around the axis of rotation. In some embodiments, the mass axis can intersect the axis of rotation along a portion of the working length of the instrument, and can be offset from the axis of rotation along other portions of the working length. In particular embodiments, the mass axis intersects the axis of rotation at one or more points, while other points of the mass axis are offset from the axis of rotation. For example, in some embodiments the mass axis can form a wavy, S-shape, sine wave, or curved shape that may generally intersect the axis of rotation at one or more points.

FIGS. 68-73 illustrate another example offset drill and/or reamer 1010. This offset drill and/or reamer 1010 is an example of a three-sided rotary offset drill and/or reamer embodiment. This offset drill and/or reamer 1010 is both triangular and radial in transverse cross-section and can be utilized to drill and/or reamer a hole in a variety of materials. The offset drill and/or reamer instrument 1010 includes a shank 1011, a free end or tip 1013, and a working portion 1012 therebetween. In this embodiment, the diameter of the working portion 1012 is slightly tapered, that is, increasing in diameter from the shank 1011 to the tip 1013. In other embodiments, the taper may be in the reverse direction, or the drill may have no taper. The working portion 1012 of the drill 1010 defines three flutes 1020A, 1020B, and 1020C. As will be described further, this embodiment of the offset drill and/or reamer 1010 and can be utilized to create a hole that is generally cylindrical.

An engine driven motor actuator with a hand-piece and/or chuck, or a handle utilized for manual actuation, can be fixedly attached to the shank 1011.

The tip 1013 can include an active or cutting surface that is confluent the working portion 1012. Alternatively, the leading tip 1013 can include a non-active or non-cutting surface that is confluent with the working portion 1012.

Figure 71:
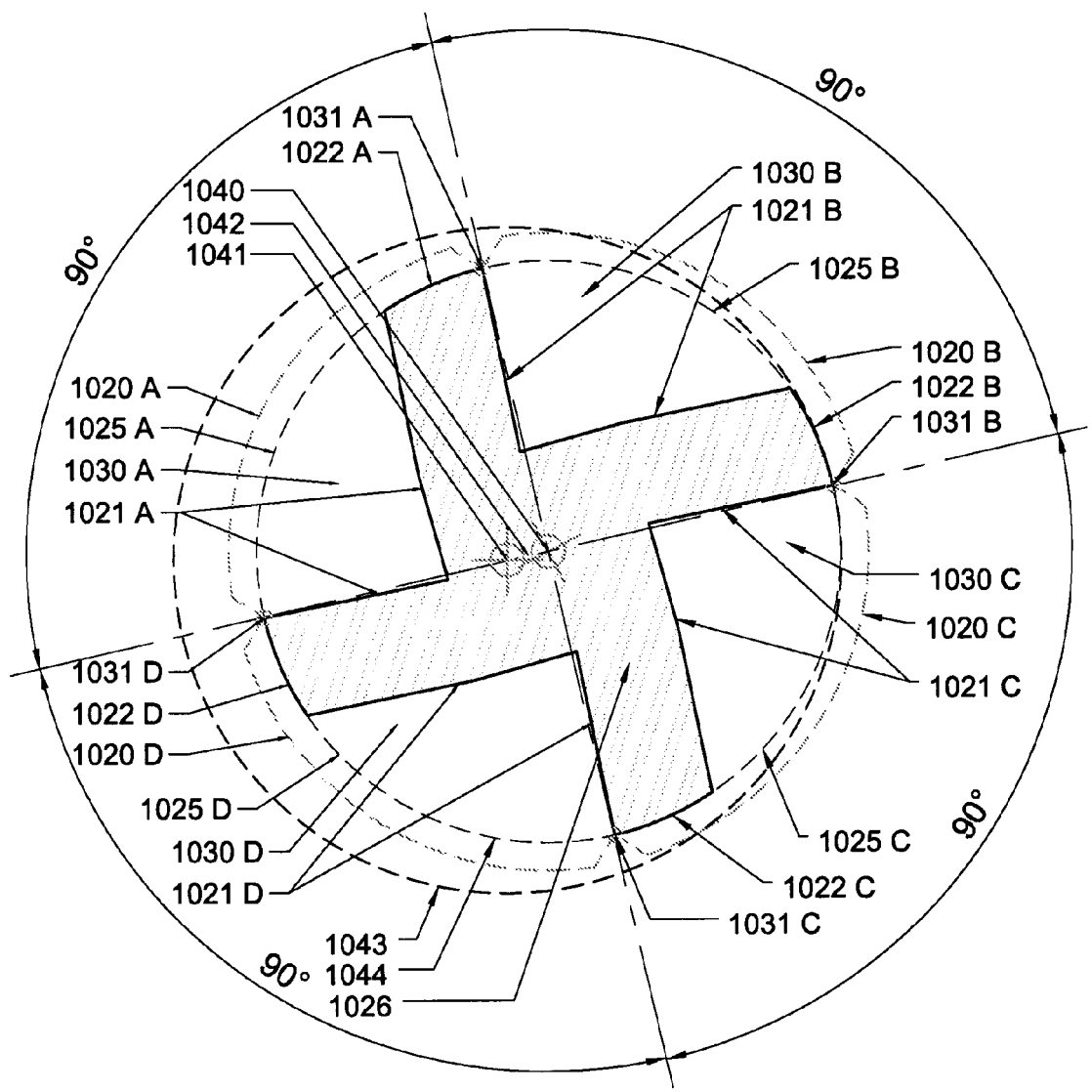
FIGS. 71 and 72 are alternate transverse cross-sectional views of the rotary offset drill and/or reamer of FIG. 68 taken at sections A-A and B-B respectively.
Figure 72:
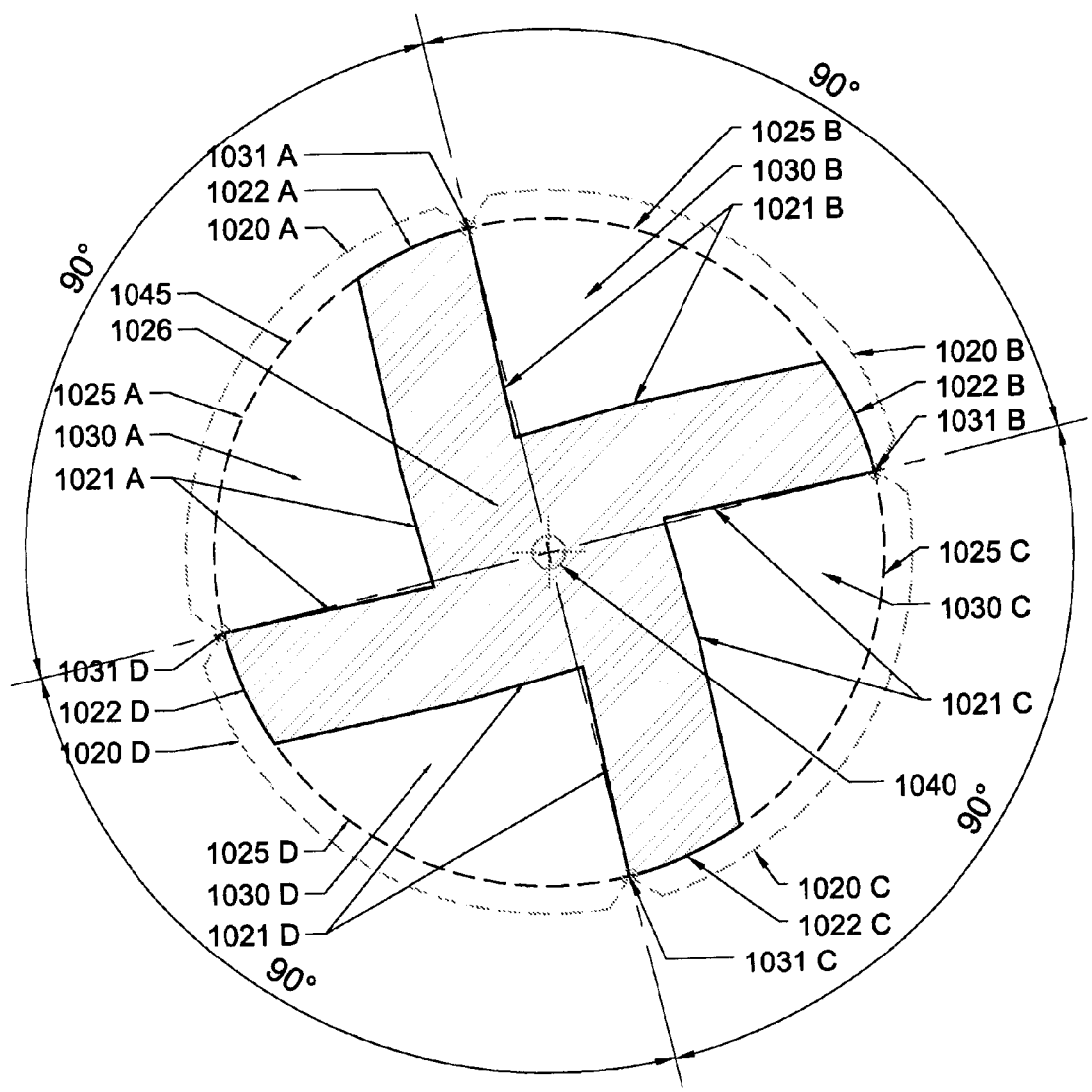
Figure 73:
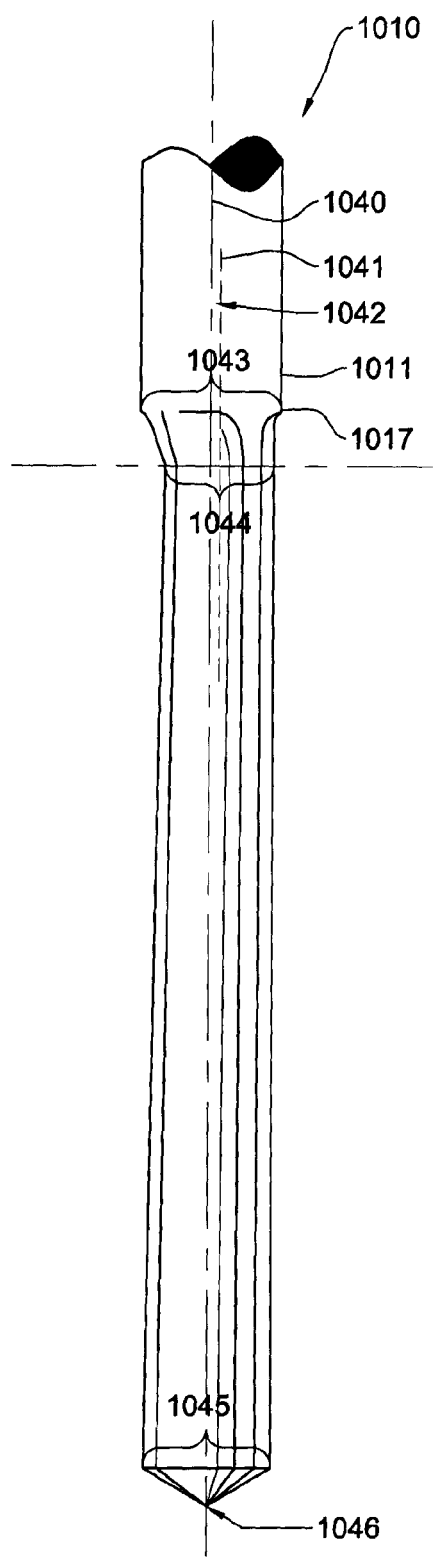
FIG. 73 depicts the three-sided rotary offset drill and/or reamer of FIG. 68, and demarcates the center of rotation and a cross-sectional center of mass, which are offset from each other.
Figure 74:
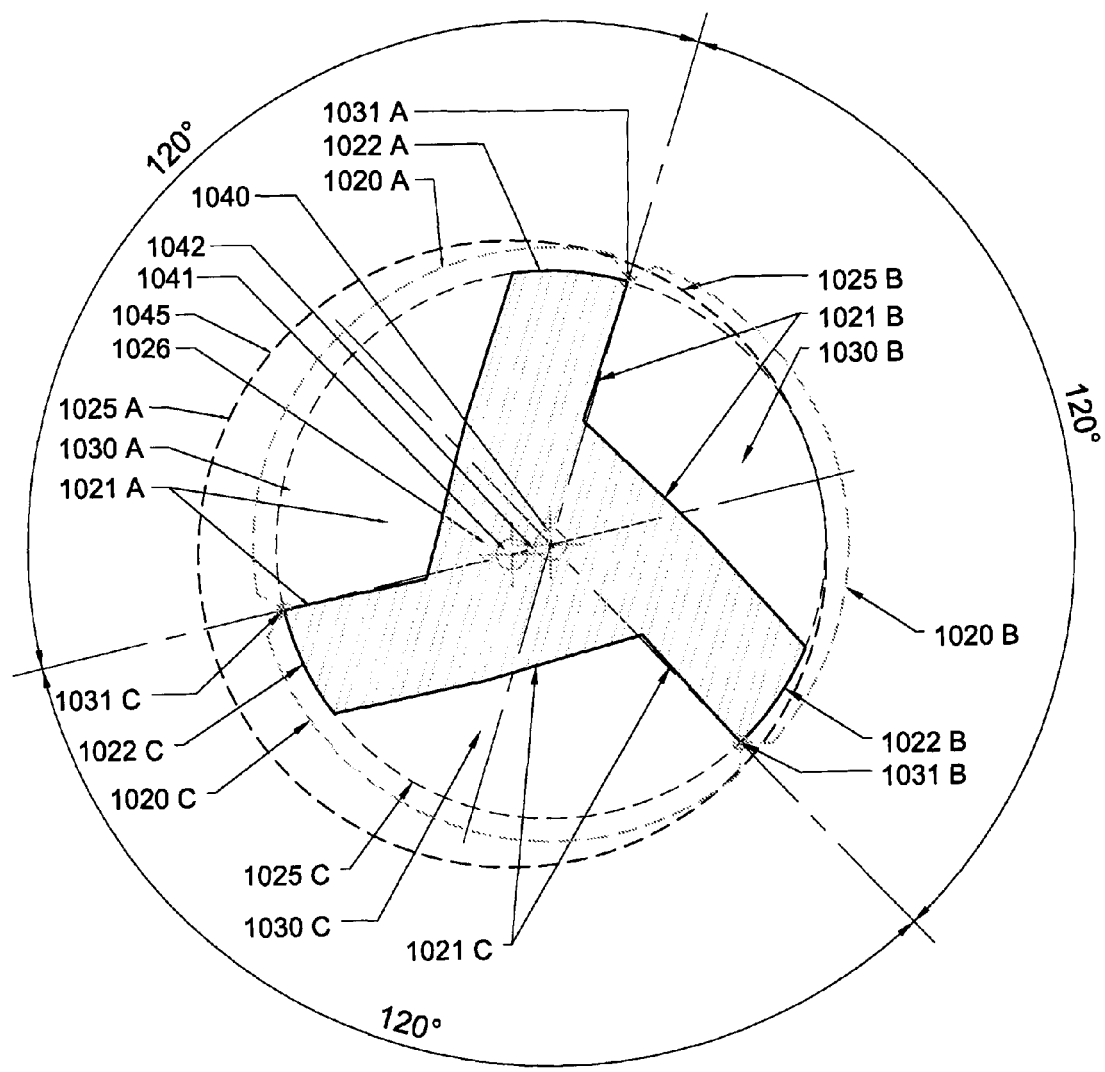
FIGS. 74 and 75 are transverse cross-sectional views of the three-sided rotary offset drill and/or reamer of FIG. 68 taken at sections A-A and B-B respectively.
Figure 75:
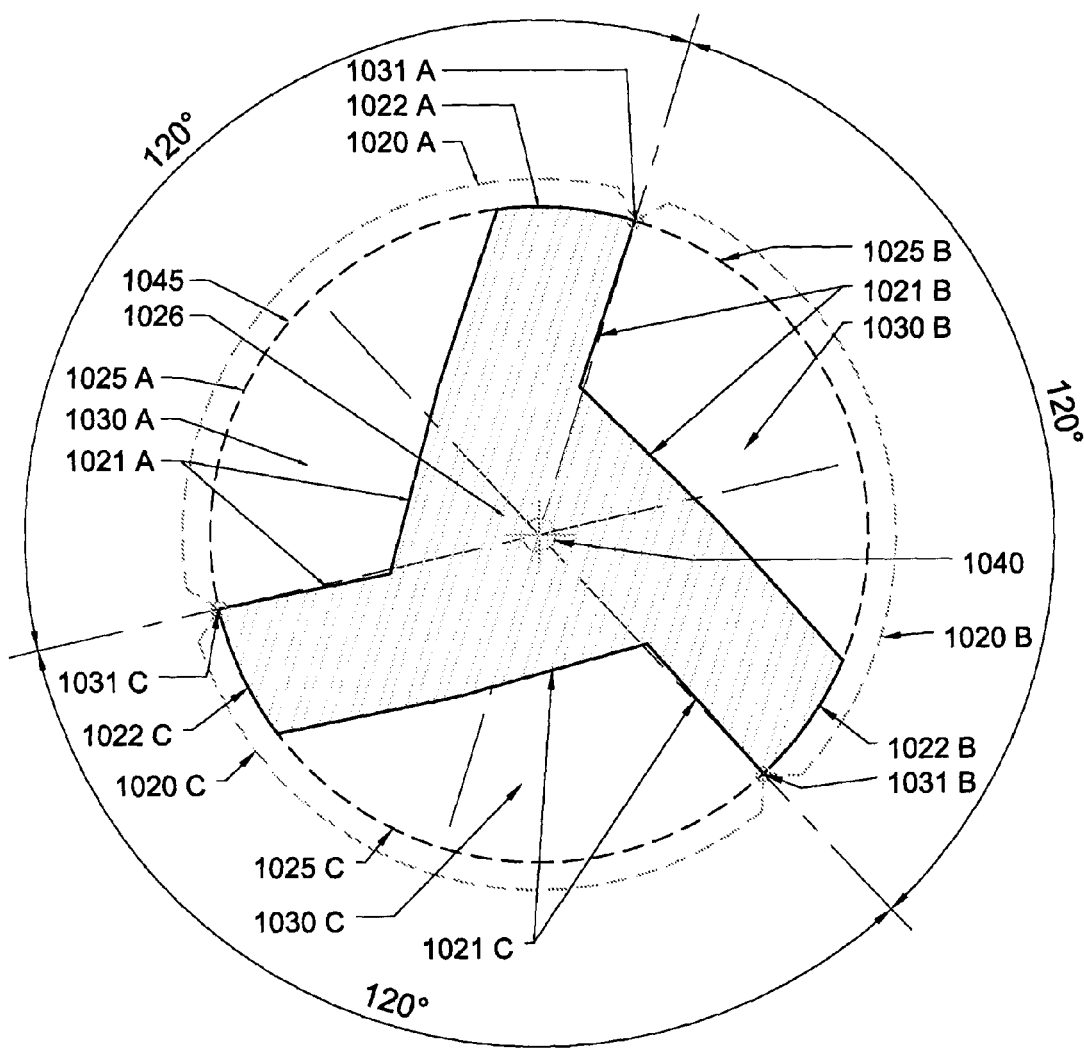
Figure 79:
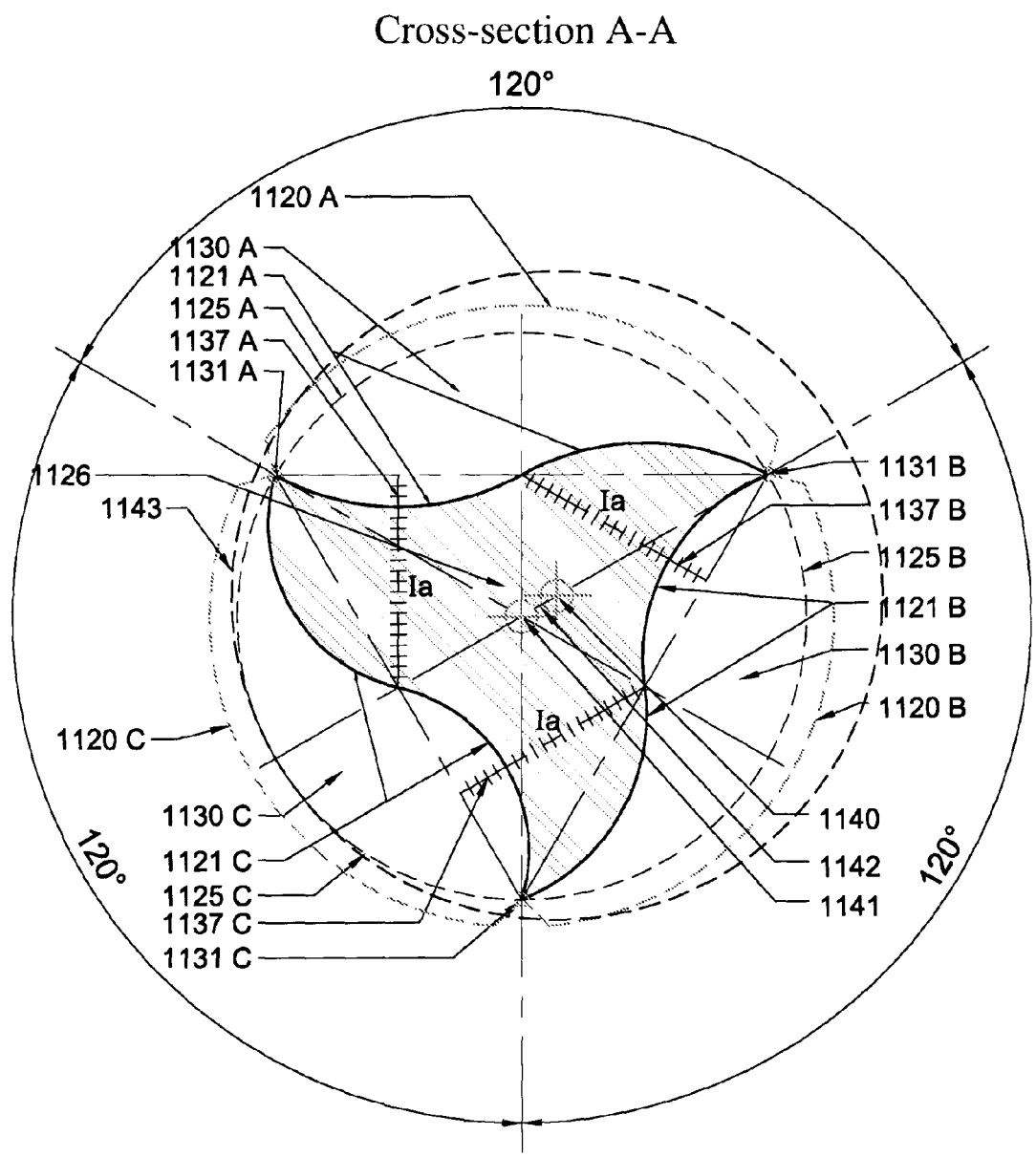
FIGS. 79 and 80 are transverse cross-sectional views of the three-sided rotary offset drill and/or reamer of FIG. 76 taken at sections A-A and B-B respectively.
Figure 80:
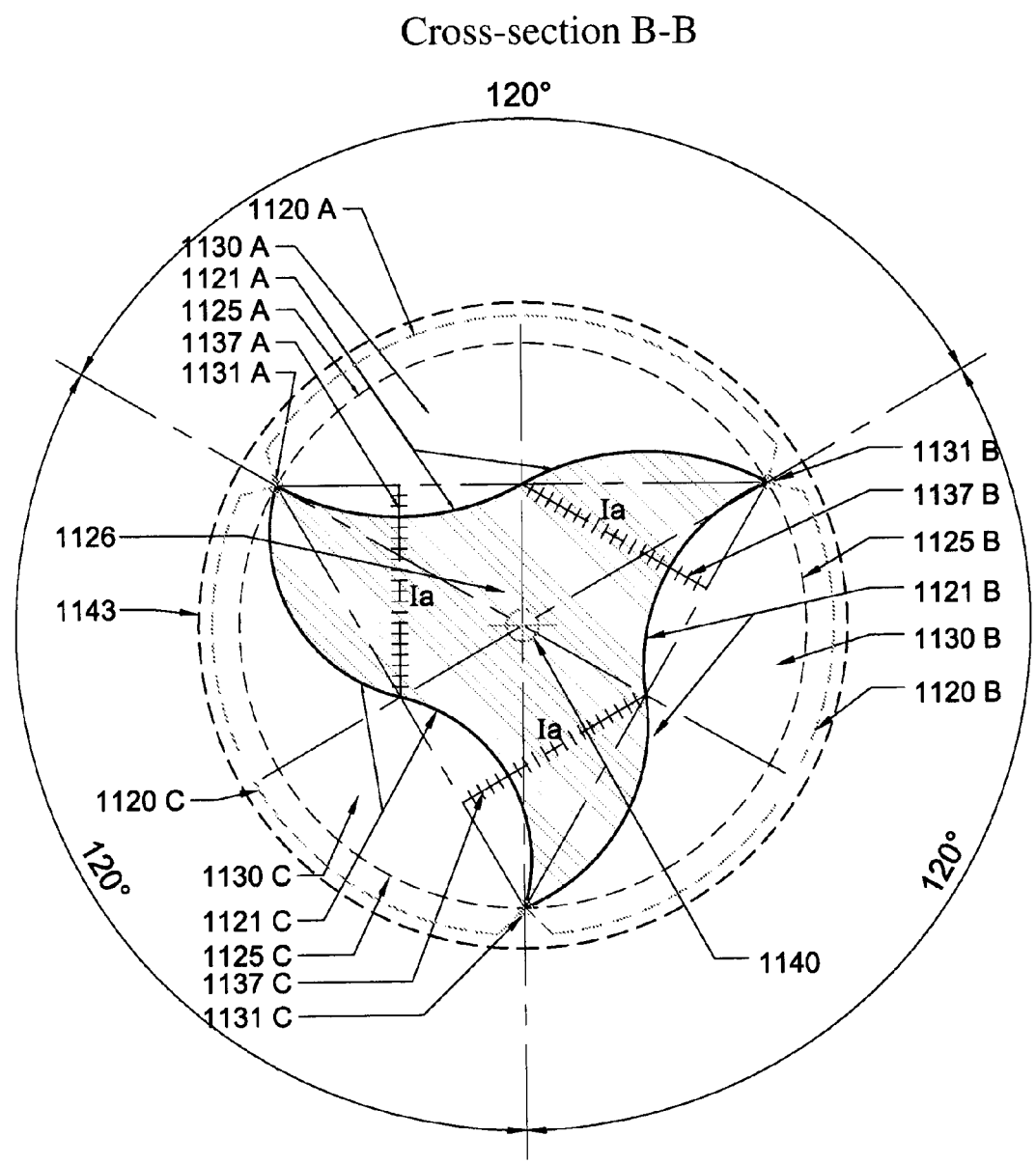

In the depicted embodiment, the MnFD 1017 is located near the shank 1011 end of the working portion 1012, and the MxFD 1018 is located near the tip 1013. Alternatively, the MnFD 1017 and the MxFD 1018 may be located at any other locations along the working body 1012. The shank 1011 above the working portion 1012 is essentially cylindrical and exhibits a slightly larger diameter than the cutting surface at the MnFD 1017. With reference in particular to FIGS. 71-73, those skilled in the art will recognize that in the depicted embodiment the center of mass 1041 of a cross-section at the MnFD 1017 is offset from the axis of rotation 1040, while the center of mass of a cross-section at the MxFD 1018 coincides with the axis of rotation 1040. Alternative arrangements are also envisioned.

As shown in FIGS. 68-73, the offset drill and/or reamer 1010 defines three continuous flutes 1020A, 1020B, and 1020C. The flutes 1020A, 1020B, and 1020C are angular groves, which extend linearly along the circumference of the working portion 1012 between the shank 1011 and the leading tip 1013 to define generally straight channels. In some embodiments, the flutes 1020A, 1020B, and 1020C may be equidistant at about 120° apart from each other. In some embodiments, the flutes 1020A, 1020B, and 1020C may be irregularly spaced, for example at 110°, 120°, and 130° to provide one example.

With further reference to FIGS. 71 and 72, it can be seen that the angular splines 1021A, 1021B and 1021C associated with flutes 1020A, 1020B, and 1020C intersect the periphery of the shank 1011 at points 1031A, 1031B, and 1031C. In the depicted embodiment, these intersections are at about 90° and are considered neutral cutting angles. It should be understood, however, that these intersections may be less than 90° (or negative, or greater than 90°).

In this embodiment, lines drawn to connect points 1031A, 1031B, and 1031C join to form a triangular configuration and are of equal depth. However, those skilled in the art will also recognized that splines 1021A, 1031B, and 1021C may be variable in depth and/or shape, and may have a wide variety of configurations.

In this example offset drill and/or reamer 1010, the splines 1021A, 1021B, and 1021C are angular (e.g., forming obtuse angles) adjacent to the web or core 1026, and the splines 1021A, 1021B, and 1021C are individually symmetrical. However, these angles may be asymmetrical in some embodiments.

The greatest depths of splines 1021A, 1021B, and 1021C are dictated by the width of the core 1026 and can be constant or variable. The cross-sectional diameter of the core portion 1026 is generally not narrower than about 20% percent of the diameter of the shank 1011. But in some cases, the cross-sectional diameter of the core portion 1026 may be narrower than about 20% of the diameter of the shank 1011.

As stated above, the offset drill and/or reamer 1010 is an example of a three-sided rotary offset drill and/or reamer embodiment. In regard to the offset feature, and further referencing FIGS. 71-73, the drill 1010 has a center-line or axis of rotation 1040 (about which the drill 1010 rotates when in use), and a mass axis 1041 that does not coincide with the axis of rotation 1040, by a distance 1042 at MnFD 1017. The mass axis 1041 is a path defined by the centers of mass of consecutive cross-sectional areas of the offset drill and/or reamer 1010. The offset is the difference between the mass axis 1041 and the axis of rotation 1040, which are displaced a distance 1042 away from each other. In this embodiment, the offset distance 1042 decreases continuously from the shank 1011 to the tip 1013, and is zero at the end-point 1046. This unique offset feature allows the instrument 1010 to cut with a precessional motion, which carves a cutting envelope with a diameter about equal to 1043 while using a smaller cross-section 1044. Accordingly, the offset drill and/or reamer 1010 cuts a cavity or hole that is generally cylindrical and corresponds to the diameter of MxFD 1018, with a drill that is substantially smaller in cross-section longitudinally. In other embodiments, the offset distance 1042 can be different, e.g., zero at the shank 1011 and increasing continuously to the tip 1013.

The features of the various offset drill and/or reamer embodiments described herein can be combined together in any suitable combination. For example, the offset drill and/or reamer 1010 is an example of a three-sided rotary offset drill and/or reamer embodiment that increases in diameter from the shank 1011 to the tip 1013, and other embodiments can also be adapted to include such a taper. For instance, an offset drill and/or reamer having the cross-sectional shape of offset drill and/or reamer 410, 510, 610, or 710 or could be used with tapered diameters of offset drill and/or reamer 1010. All combinations and sub-combinations of the features and designs provided herein are within the scope of this disclosure.

Figure 81:
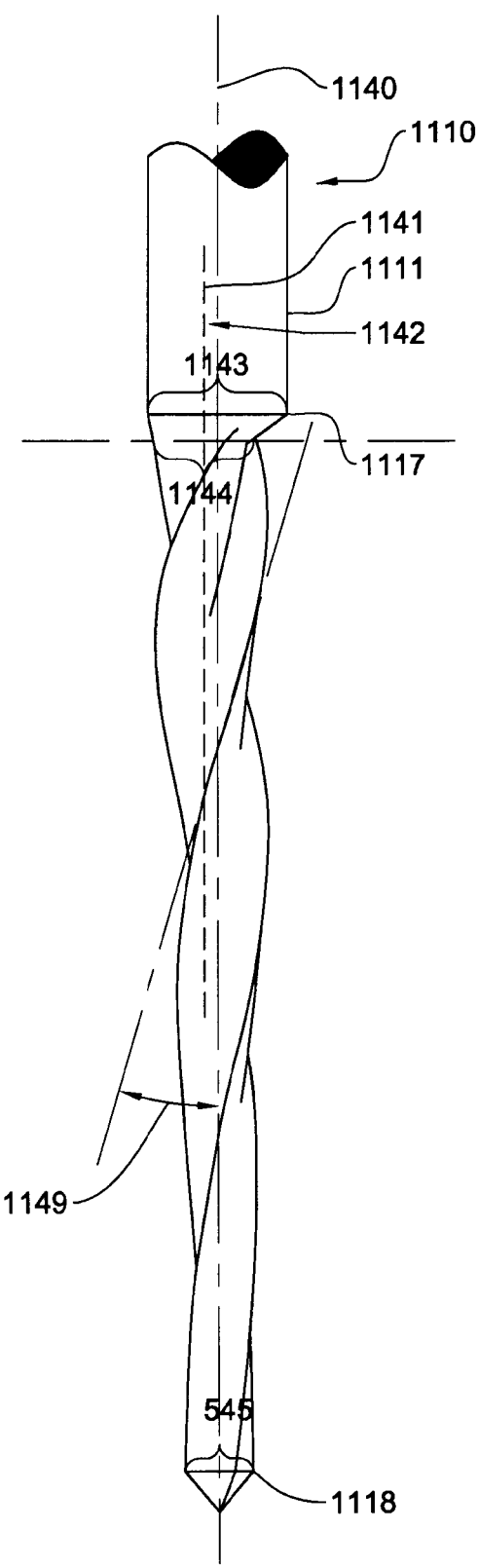
FIG. 81 depicts the three-sided rotary offset drill and/or reamer of FIG. 76, and demarcates the center of rotation and a cross-sectional center of mass, which are offset from each other.

FIG. 76-81 provide an example hybridized twist drill 1110 design that includes a working body 1112 with standard twist drill at the tip end and a precessional cutting device in the middle and/or shank end of the cutting device 1110. The distal or tip end is intended to create a pilot hole, while upper part of the device will cut a tapered (or cylindrical) hole precessionally after the tip potion passes completely through the work piece. To avoid repetition, it can be understood that in the depicted embodiment the design characteristics in the middle and/or shank end are similar to those of FIG. 22-26 and the design characteristics in the distal or tip end are similar to those of FIGS. 7 and 8, though in this embodiment the tool is three-sided. Thus, those features will not be repeated here. An additional visualization of the hybridization embodiment is depicted in FIG. 81. It should be understood that any of features of any of the precessional cutting instrument embodiments provided herein can be incorporated in the middle and/or shank end of the device 1110.

As illustrated in FIG. 81 the drill 1110 has a center-line or axis of rotation 1140 (about which the drill 1110 rotates when in use), and a mass axis 1141 that does not consistently coincide with the axis of rotation 1140. The mass axis 1141 is a path of points defined by the centers of mass of consecutive cross-sectional areas of the offset drill and/or reamer 1110. The offset is the difference between the mass axis 1141 and the axis of rotation 1140 (which are displaced a distance 1142 away from each other). In the depicted embodiment, the offset distance 1142 decreases continuously from the shank 1111 to the tip 1113, and becomes zero before it completely reaches the tip end 1148. However, other relationships between the mass axis 1141 and the axis of rotation 1140 are also envisioned.

FIG. 82 depicts another example embodiment of an offset cutting instrument 1210. This embodiment has a corkscrew shape or three-dimensional spiral shape. For example, as shown in FIG. 83, a center of mass path 1241 of cutting instrument 1210 revolves around the axis of rotation 1240 as shown. In some embodiments, the corkscrew shape of the mass axis 1241 extends the entire working body of the instrument 1210. In some embodiments, the corkscrew shape of the mass axis 1241 extends along only a portion of the working body of the instrument 1210.

It should be understood that the cutting instrument 1210 can include any of the cross-sectional shapes and/or other features of any of the other cutting instrument embodiments provided herein, and extensions thereof, and combinations thereof.

FIGS. 84, 85, and 86 illustrate the characteristic of the drill 1210 to cut using precessional motion. As previously mentioned, precession describes the motion which occurs whenever the axis about which a body is spinning is, itself, rotating about another axis. As shown in FIG. 83, the theoretical axis of rotation 1240 and the mass axis 1241 are offset from each other. The amount of offset between the axis of rotation 1240 and the mass axis 1241 is defined by the distance between these two axes, and the offset distance varies along the length of the drill. Due to having centers of mass that are offset from the axis of rotation 1240, the drill 1210 exhibits a phenomenon during rotation that is known as precession or, in the vernacular, swagger. In the case of offset drills, the axis of precession is substantially "inherent" or ground into design and not controlled by external variables. By building the axis of precession into the offset drill, the precessional angle, and therefore the cutting action, can be precisely controlled.

With adequate angular velocity and a sufficient offset center of mass, an offset drill can experience angular accelerations, which can in turn produce radial bodily movements of the drill. This occurs because the vector of centrifugal force $F=ma$ (or force equals mass times acceleration) displaces the centroids of the drill radially to an extent that is limited by the spring constant for the drill as defined by Hooke's law $F=-kx$ (where k is the spring constant and x is the unit length of deflection). In any event, cutting along a precessional axis is accomplished by offsetting the centroid or center of mass of the geometric cross-sectional area over a unit length of the drill 1210 and away from the axis or center of rotation 1240 of the drill 1210. Application of simple wave theory may also be useful in understanding the precessional motion of the cutting instruments provided herein.

With further reference to elongate drill 1210, and as a further description of the properties of the drill 1210, the arcuate cutting path can be associated with a wave of amplitude x (refer to FIG. 83). Thus, the total distance traveled by any point on the arc equals 2x, which relates to the cut diameter for that point.

With continued reference to FIGS. 84, 85, and 86, it can also be envisioned that cutting occurs alternately in that no two cutting angles engage the walls of the hole immediately opposite each other at any one time. Said differently, at locations along the length of the working body, not all cutting edges of the cutting instrument are in contact with the wall of the hole being drilled or reamed. This feature allows the instrument 1210 to create large cutting envelopes while using a drill 1210 with a smaller cross-sectional areas. Those skilled in the art will appreciate that this property improves drill flexibility, reduces cyclic fatigue, mitigates binding or taper lock (the screwing effect), and mitigates transportation away from the intended cut axis, or the original configuration of the space in the case of reaming.

In some embodiments of the cutting instruments provided herein, the cutting instrument has at least one longitudinal irrigation passage which passes through a shank portion of the cutting instrument and transverses a core or web of the drill exiting laterally and distally. In some such embodiments, the passage is configured to allow flow of irrigation fluid to a lateral perimeter or tip of the cutting instrument.

In some embodiments of the cutting instruments provided herein, the flutes have differing degrees of diametrical taper when viewed in longitudinal cross-section. In some embodiments, the cutting instruments provided herein have at least two regions of differing diametric tapers when viewed in transverse cross-section. In some embodiments of the cutting instruments provided herein, have radial lands without margins. Alternately, some embodiments have radial lands with a margin, or more than one margin. In some embodiments, the drill and/or reamers provided herein are constructed of a material that is homogenous (e.g., made of one piece of tool material). Alternately, some embodiments of the cutting instruments provided herein are constructed of two or more materials 491, 492 (FIG. 4A). For example, in some embodiments the drill and/or reamer is tipped, i.e., has a body made of one type of material and a tip made of another type of material (e.g., a working body of steel of uniform hardness and a tip made of cemented carbide for added durability).

While the motion of cutting instruments described herein is generally referred to a rotary motion, it should be understood that the cutting instruments are not limited to being used in a purely rotary manner. For example, the cutting instruments provided herein can also be used in a reciprocating manner (back and forth rotations around the longitudinal axis of the instruments, or back and forth translation along the longitudinal axis of the instruments). In addition, the cutting instruments provided herein can be used in the context of a hammer drill motion (reciprocating in both axial rotations and longitudinal translation manners).

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A cutting instrument configured for industrial usage, the cutting instrument comprising:
    a shank configured to be releasably attachable to a motor to rotate the cutting instrument about an axis of rotation; and
    a drill body configured for industrial drilling extending from the shank, the drill body including a shank end where the drill body extends from the shank, a free end at an end of the drill body that is opposite of the shank end, and at least two flutes each extending continuously between the shank end and the free end, each flute of the at least two flutes defined at a respective location around a circumference of the shank end such that the at least two flutes are equispaced around the circumference with respect to each other, the drill body including a cutting portion between the shank end and the free end, the drill body comprising a plurality of transverse cross-sections, each transverse cross-section of the drill body having a center of mass, the drill body having a center of mass path that is defined by the centers of mass of all transverse cross-sections of the body, wherein a center of mass of a transverse cross-section at the shank end is offset from the axis of rotation, and a center of mass of a transverse cross-section at the free end is closer to the axis of rotation than the center of mass of the transverse cross-section at the shank end.

2. The cutting instrument of claim 1, wherein a distance of the center of mass from the axis of rotation decreases linearly from the shank end to the free end.

3. The cutting instrument of claim 1, wherein the center of mass of the transverse cross-section at the free end lies on the axis of rotation.

4. The cutting instrument of claim 1, wherein the center of mass path comprises a three dimensional spiral around the axis of rotation.

5. The cutting instrument of claim 1, wherein the drill body has a substantially constant diameter from the shank end to the free end.

6. The cutting instrument of claim 1, wherein the drill body is tapered from the shank end to the free end such that the shank end has a larger cutting diameter than the free end.

7. The cutting instrument of claim 1, wherein the drill body is tapered from the free end to the shank end such that the free end has a larger cutting diameter than the shank end.

8. The cutting instrument of claim 1, wherein the drill body is tapered from the free end to the shank end, and wherein the tapered body cuts along a dual axis, the dual axis comprising a first axis corresponding the central axis of rotation and a second axis corresponding to an offset mass path which rotates around the central axis.

9. The cutting instrument of claim 1, wherein the drill body includes a transverse cross-section that is asymmetrical, bisymmetrical, symmetrical, triangular, biangular, or quadrilateral.

10. The cutting instrument of claim 1, wherein the drill body includes a first transverse cross-section and a second transverse cross-section, wherein the first transverse cross-section has a first geometry, and wherein the second transverse cross-section has a second geometry different from the first geometry.

11. The cutting instrument of claim 1, comprising a chisel tip at the free end of the drill body.

12. The cutting instrument of claim 11, wherein the chisel tip forms an angle of greater than 40 degrees.

13. The cutting instrument of claim 11, wherein an end of the chisel tip is on the axis of rotation.

14. The cutting instrument of claim 1, wherein a portion of the drill body near the free end has blunted cutting edges.

15. The cutting instrument of claim 1, wherein the cutting instrument is comprised of a nickel-titanium alloy.

16. The cutting instrument of claim 1, wherein the center of mass of the transverse cross-section at the free end is offset from the axis of rotation.

17. The cutting instrument of claim 1, wherein the cutting instrument has a first portion extending along the drill body, wherein the first portion has a diametrical taper at a first taper rate, wherein the cutting instrument has a second portion extending along the drill body, and wherein the second portion has a diametrical taper at a second taper rate that is different than the first taper rate.

18. The cutting instrument of claim 1, wherein the cutting portion is coated with one of the group consisting of diamond, amorphous diamond, diamond compact bits, and diamond-like carbon.

19. The cutting instrument of claim 1, wherein the cutting portion includes radial lands without margins.

20. The cutting instrument of claim 1, wherein the cutting portion is coated with one of the group consisting of titanium nitride, titanium aluminum nitride, titanium carbon nitride, zirconium nitride, and black oxide.

21. The cutting instrument of claim 1, wherein the cutting instrument consists of one type of material.

22. The cutting instrument of claim 1, wherein a portion of the cutting body at the free end comprises a first type of material and other portions of the cutting body comprise a second type of material that is different than the first type of material.

23. The cutting instrument of claim 1, wherein a distance of the center of mass from the axis of rotation decreases monotonically from the shank end to the free end.

24. The cutting instrument of claim 1, wherein the cutting instrument is comprised of steel.

25. The cutting instrument of claim 1, wherein the cutting instrument comprises cemented carbide.

26. The cutting instrument of claim 22, wherein the first type of material comprises cemented carbide.

27. The cutting instrument of claim 22, wherein second type of material comprises steel.

28. A method of cutting a space in a material, the method comprising:
    driving, using a motor, the cutting instrument of claim 1;
    contacting, while driving the cutting instrument, the free end of the cutting instrument against the material; and
    extending, while driving the cutting instrument, at least a portion of the cutting instrument into the material to remove portions of the material to thereby create the space in the material.

29. The method of claim 28, wherein the extending the cutting instrument comprises precessional motion of the cutting instrument.

30. The method of claim 28, wherein rotating the cutting instrument includes causing the cutting instrument to form sinusoidal waves within the space.

31. The method of claim 28, wherein rotating the cutting instrument includes causing the cutting instrument to form helical waves within the space.

32. The method of claim 28, wherein the cutting instrument is comprised of a super-elastic material.

33. The method of claim 28, wherein the driving the cutting instrument comprises reciprocating the cutting instrument rotationally about the axis of rotation in a back and forth motion.

34. The method of claim 28, wherein the driving the cutting instrument comprises reciprocating the cutting instrument longitudinally along the axis of rotation in a back and forth motion.

35. The method of claim 28, wherein the driving the cutting instrument comprises reciprocating the cutting instrument rotationally about the axis of rotation and longitudinally along the axis of rotation in a back and forth motion.

* * * * *